(12) United States Patent
Theodoropoulos

(10) Patent No.: US 9,422,587 B2
(45) Date of Patent: Aug. 23, 2016

(54) SELECTION OF IMPROVED MICROBIAL STRAINS FOR PRODUCTION OF SUCCINIC ACID FROM GLYCEROL

(75) Inventor: Konstantinos Theodoropoulos, Manchester (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 14/112,759

(22) PCT Filed: Apr. 20, 2012

(86) PCT No.: PCT/GB2012/050887
§ 371 (c)(1),
(2), (4) Date: Oct. 18, 2013

(87) PCT Pub. No.: WO2012/143736
PCT Pub. Date: Oct. 26, 2012

(65) Prior Publication Data
US 2014/0038229 A1 Feb. 6, 2014

(30) Foreign Application Priority Data

Apr. 20, 2011 (GB) .................... 1106686.7

(51) Int. Cl.
*C12Q 1/04* (2006.01)
*C12P 7/46* (2006.01)
*C12R 1/01* (2006.01)
*C12N 1/20* (2006.01)
*C12N 1/36* (2006.01)
*C12M 1/00* (2006.01)

(52) U.S. Cl.
CPC ............. *C12Q 1/04* (2013.01); *C12M 21/00* (2013.01); *C12N 1/20* (2013.01); *C12N 1/36* (2013.01); *C12P 7/46* (2013.01); *C12R 1/01* (2013.01)

(58) Field of Classification Search
None
See application file for complete search history.

(56) References Cited

FOREIGN PATENT DOCUMENTS

| WO | 2007115228 A2 | 10/2007 |
|---|---|---|
| WO | 2009024294 A1 | 2/2009 |
| WO | 2009048202 A1 | 4/2009 |
| WO | 2009082050 A1 | 7/2009 |
| WO | 2010092155 A1 | 8/2010 |
| WO | 2012143736 A1 | 10/2012 |

OTHER PUBLICATIONS

Yuzbashev, T.V., Yuzbashev, E.Y., Sobolevskaya, T.I., Laptev, I.A., Vybornaya, T.V., Larina, A.S., Matsui, K., Fukui, K., and Sineoky, S.P. "Production of Succinic Acid at Low pH by a Recombinant Strain of the Aerobic Yeast Yarrowia lipolytica", Biotechnology and Bioengineering 2010, vol. 107, pp. 673-682.*
Scholten, E., Renz, T., and Thomas, J. "Continuous cultivation approach for fermentative succinic acid production from crude glycerol by Basfia succiniciproducens DD1", Biotechnology Letters 2009, vol. 31, pp. 1947-1951.*
Lee, P.C., Lee, W.G., Lee, S.Y., and Chang, H.N. "Succinic Acid Production with Reduced By-Product Formation in the Fermentation of Anaerobiospirillum succiniciproducens Using Glycerol as a Carbon Source", Biotechnology and Bioengineering 2001, vol. 72, pp. 41-48.*
McKinlay et al., "A genomic perspective on the potential of Actinobacillus succinogenes for industrial succinate production", BMC Genomics 2010, vol. 11, Article 680, pp. 1-16.*
PCT/GB2012/050887 International Search Report dated Jun. 19, 2012; 4 pages.
PCT/GB2012/050887 Written Opinion dated Jun. 19, 2012; 6 pages.
PCT/GB2012/050887 International Preliminary Report on Patentability dated Oct. 22, 2013; 6 pages.
Scholten et al. Succinic acid production by a newly isolated bacterium. Biotechnology Letters (2008). 30 (12):2143-2146.
Yazdani et al. Anaerobic fermentation of glycerol: a path to economic viability for the biofuels industry. Current Opinion in Biotechnology (2007). 18(3):213-219.
Zhang et al. Fermentation of glycerol to succinate by metabolically engineered strains of *Escherichia coli*. Applied and Environmental Microbiology (2010). 76(8): 2397-2401.

* cited by examiner

*Primary Examiner* — Renee Claytor
*Assistant Examiner* — Michelle F Paguio Frising
(74) *Attorney, Agent, or Firm* — Linda B. Huber; Nixon Peabody LLP

(57) ABSTRACT

Provided are methods for generating a microorganism with improved ability to convert glycerol to succinic acid. These methods comprise combining a microorganism with ability to convert glycerol to succinic acid and a medium containing glycerol to produce a fermentation mixture; allowing fermentation to occur such that succinic acid is produced; and assaying for an indication of glycerol metabolism. These latter two steps may be repeated as necessary. Also provided are microorganisms generated in this manner, particularly bacteria deposited at the NCIMB on 13 Apr. 2011 with the Accession Number NCIMB 41825. A method of producing succinic acid from glycerol is also provided, this method comprising: mixing a microorganism according to claim of the invention with a medium comprising glycerol to produce a fermentation mixture; and incubating the fermentation mixture, under conditions that promote fermentation to produce succinic acid, until succinic acid is produced. Succinic acid produced by such methods is also provided.

19 Claims, 23 Drawing Sheets

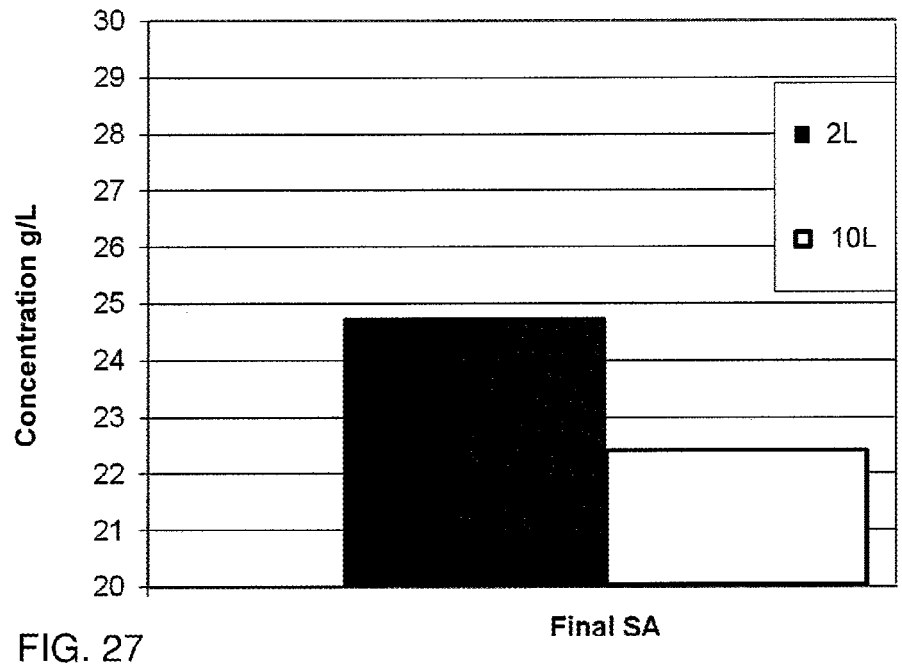

FIG. 27

Figure 1:
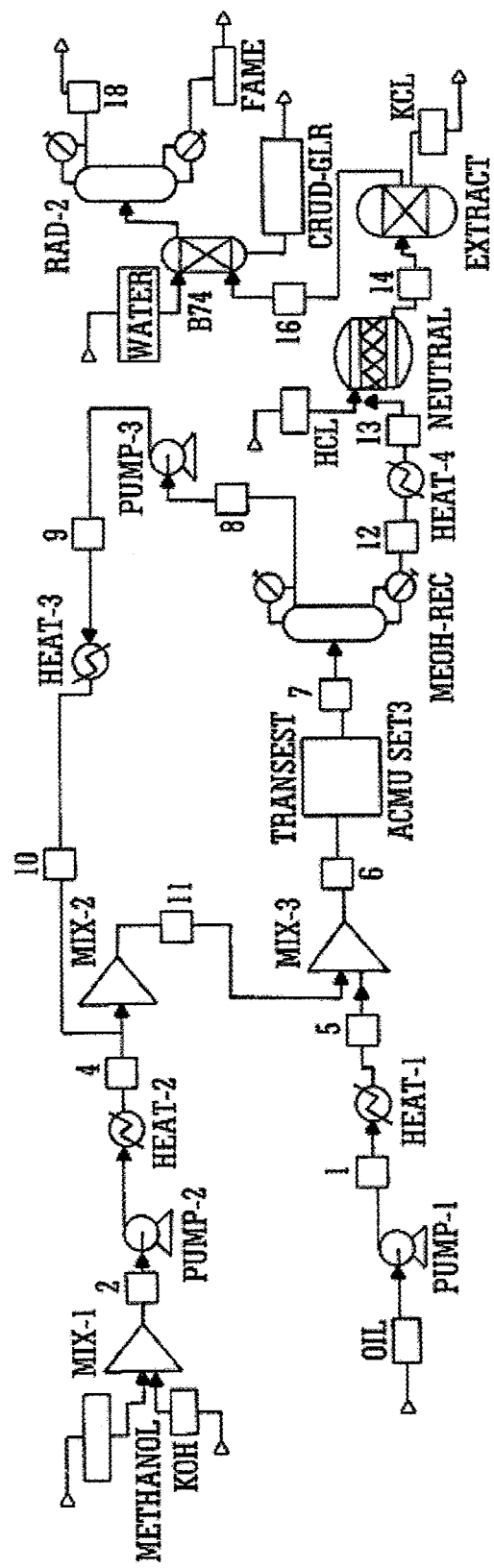

| | | Capital Cost (Million €) | | | |
| --- | --- | --- | --- | --- | --- |
| | | Scenario 0 | Scenario 1 | Scenario 2 | Scenario 3 |
| BMC | | 1.9353 | 2.0083 | 2.0198 | 3.9254 |
| Installation (1) | 0.20 * BMC | 0.3871 | 0.4017 | 0.404 | 0.7851 |
| Piping (2) | 0.30 * BMC | 0.5806 | 0.6025 | 0.6059 | 1.1776 |
| Instrumentation (3) | 0.20 * BMC | 0.3871 | 0.4017 | 0.404 | 0.7851 |
| Insulation (4) | 0.03 * BMC | 0.0581 | 0.0602 | 0.0606 | 0.1178 |
| Electrical (5) | 0.10 * BMC | 0.1935 | 0.2008 | 0.202 | 0.3925 |
| Buildings (6) | 0.30 * BMC | 0.5806 | 0.6025 | 0.6059 | 1.1776 |
| Yard improvements (7) | 0.10 * BMC | 0.1935 | 0.2008 | 0.202 | 0.3925 |
| Auxiliary facilities (8) | 0.25 * BMC | 0.4838 | 0.5021 | 0.505 | 0.9813 |
| TPDC[a] = BMC + (1)+(2)+...+(8) | | 4.7994 | 4.9806 | 5.0091 | 9.7349 |
| Contructor's fee (9) | 0.03 * TPDC | 0.144 | 0.1494 | 0.1503 | 0.292 |
| Contigency (10) | 0.07 * TPDC | 0.336 | 0.3486 | 0.3506 | 0.6814 |
| FCI = TPDC + (9) + (10) | | 5.2794 | 5.4786 | 5.51 | 10.7084 |
| Working Capital, Land Use, Salvage | | 0 | 0 | 0 | 0 |

TABLE 1

FIG. 28A    Capital cost analysis for scenarios 0-3
a: Total Plant Direct Cost

| Annual Production Cost (Million €) | | | | | |
|---|---|---|---|---|---|
| | Price (€/ton) | Scen. 0 | Scen. 1 | Scen. 2 | Scen 3 |
| Methanol [a] (1) | 202.00 | 0.2654 | 0.2654 | 0.2654 | 0.2654 |
| Rapeseed [b] (2) | 335.00 | 6.4950 | 6.4950 | 6.4950 | 6.4950 |
| KOH [a] (3) | 219.90 | 0.0261 | 0.0261 | 0.0261 | 0.0261 |
| HCl [a] (4) | 85.43 | 0.0135 | 0.0135 | 0.0135 | 0.0135 |
| ($C_{RM}$) Raw materials (5) = (1)+(2)+(3)+(4) | | 6.8001 | 6.8001 | 6.8001 | 6.8001 |
| | Energy Cost (€/kWh) | | | | |
| Electricity [e] (6) | 0.0772 | 0.0236 | 0.0236 | 0.0236 | 0.0402 |
| Process steam [d] (7) | 0.0180 | 0.2795 | 0.2829 | 0.2854 | 0.6143 |
| Cooling Water [c] (8) | 0.0009 | 0.0028 | 0.0030 | 0.0031 | 0.0175 |
| ($C_U$) Total Utilities (9) = (6)+(7)+(8) | | 0.3059 | 0.3096 | 0.3122 | 0.6721 |
| Labour Costs (10) | 28,000 (€/operator) | 0.2240 | 0.2240 | 0.2240 | 0.2800 |
| Maintenance, Repair (11) | 0.03 * FCI | 0.1584 | 0.1644 | 0.1653 | 0.3213 |
| Laboratory (12) | 0.1 * (10) | 0.0224 | 0.0224 | 0.0224 | 0.0280 |
| Supervision (13) | 0.25 * (10) | 0.0560 | 0.0560 | 0.0560 | 0.0700 |
| Insurance, local taxes and royalties (14) | 0.04 * FCI | 0.2112 | 0.2191 | 0.2204 | 0.4283 |
| Plant Overhead costs (15) | 0.5 * ((10)+(11)+(13)) | 0.2192 | 0.2222 | 0.2227 | 0.3356 |
| ($C_E$) Extra Cost (16) = (10)+(11)+...+(15) | | 0.8912 | 0.9081 | 0.9108 | 1.4632 |
| ($C_{WD}$) Wastecost [c] (17) | 0.0257 (€/kg) | 0.0442 | 0.0268 | 0.0295 | 0.0970 |
| ($C_{APC}$) Ann. Production Cost = (5)+(9)+(16)+(17) | | 8.0414 | 8.0445 | 8.0526 | 9.0325 |
| Unit Production Cost (€/L) | | 0.8976 | 0.9029 | 0.9038 | 1.0137 |

Table 2 Annual production cost of Scenarios 0-3
a: found in [45]
b: found in [46]
c: found in [39]
d: found in [42]
e: found in [43]

FIG. 28B

| Annual Revenues (Million €) | | | | | |
|---|---|---|---|---|---|
| | Price (€/ton) | Scenario 0 | Scenario 1 | Scenario 2 | Scenario 3 |
| Biodiesel [a] (1) | 908.00 | 7.1196 | 7.1196 | 7.1196 | 7.1196 |
| Succinic Acid [b] (2) | 4311.00 | 0.0000 | 0.0000 | 0.0000 | 1.8556 |
| Rapeseed Meal [c] (3) | 175.00 | 2.0069 | 2.0069 | 2.0069 | 2.0069 |
| Glycerol (95%) [d] (3) | 350.00 | 0.0000 | 0.0000 | 0.2002 | 0.0000 |
| Glycerol (80%) [a] (3) | 68.80 | 0.0000 | 0.0467 | 0.0000 | 0.0000 |
| Annual Revenues (4) = (3)+(2)+(1) | | 9.1265 | 9.1732 | 9.3267 | 10.9821 |
| Taxes | | 0.0 | 0.0 | 0.0 | 0.0 |
| Total Production Cost (5) | | 8.0414 | 8.0445 | 8.0526 | 9.0325 |
| Annual Profits = (4)-(5) | | 1.0851 | 1.1287 | 1.2741 | 1.9496 |

Table 3 Annual revenues and profits for Scenarios 0-3
a: found in [16]
b: found in [47]
c: found in [48]
d: found in [42]

FIG. 28C

|  | Scenario 3 | Scenario 2 | Scenario 1 | Scenario 0 |
|---|---|---|---|---|
| NPV (M.€) | 9.945 | 7.988 | 6.479 | 6.216 |
| IRR | 17.48% | 22.74% | 20.07% | 20.02% |
| PBP (yr) | 5.5 | 4.3 | 4.9 | 4.9 |
| ROI | 18.21% | 23.12% | 20.60% | 20.55% |
| DPBP (yr) | 7.200 | 5.400 | 6.100 | 5.6 |
| Gross Margin | 17.75% | 13.66% | 12.30% | 11.89% |

Table 4 Profitability indicators of the four scenarios

FIG 28D

| Material | Sensitivity Slopes |
|---|---|
| Rapeseed | -6.88E+07 |
| Biodiesel | 7.54E+07 |
| Succinic acid | 1.97E+07 |
| GLR 95% | 2.12E+06 |
| GLR 80% | 4.95E+05 |

FIG. 28E

Table 5 Sensitivity analysis results

| Country | Production (million litres) |
|---|---|
| Germany | 2499 |
| United States | 852 |
| France | 625 |
| Italy | 568 |
| Czech Republic | 153 |
| Spain | 142 |
| Malaysia | 136 |
| Poland | 114 |
| United Kingdom | 114 |
| Australia | 91 |
| Austria | 85 |
| Denmark | 80 |
| Philippines | 68 |
| Brazil | 68 |
| China | 68 |
| Others | 490 |
| Europe total | 4504 |
| Americas total | 1113 |
| World total | 6153 |

FIG. 28F

Table 6. Global Production of Biodiesel in 2006 [7

| So (g-GLR/L) | Yield (g-SA/g-GLR) | Productivity (g-SA/L/h) | Final [SA] (g-SA/L) | Carbon Recovery% | Residual Glycerol | FA/SA* | AA/SA* |
|---|---|---|---|---|---|---|---|
| 3.7 | 1.04 | 0.13 | 3.9 | 1.20 | 0.0 | 0.04 | 0.12 |
| 5.1 | 1.12 | 0.17 | 5.7 | 1.28 | 0.0 | 0.03 | 0.11 |
| 7.2 | 0.87 | 0.18 | 6.3 | 0.99 | 0.0 | 0.05 | 0.09 |
| 9.5 | 1.23 | 0.18 | 11.7 | 1.34 | 0.0 | 0.04 | 0.05 |
| 10.0 | 0.92 | 0.19 | 9.2 | 1.03 | 0.0 | 0.04 | 0.09 |
| 15.0 | 0.92 | 0.20 | 13.7 | 1.00 | 0.0 | 0.04 | 0.04 |
| 19.8 | 1.23 | 0.18 | 22.4 | 1.27 | 1.6 | 0.05 | 0.07 |
| 21.5 | 0.85 | 0.24 | 18.0 | 0.91 | 0.3 | 0.03 | 0.06 |
| 31.0 | 0.96 | 0.23 | 26.7 | 0.97 | 3.1 | 0.05 | 0.07 |
| 36.4 | 0.78 | 0.26 | 28.3 | 0.89 | 0.1 | 0.06 | 0.08 |
| 36.9 | 0.80 | 0.27 | 29.3 | 0.93 | 0.1 | 0.07 | 0.10 |
| 66.0 | 0.93 | 0.08 | 11.2 | 0.19 | 54.0 | 0.06 | 0.07 |

Table 7. Experimental Results for different initial conditions
* FA/SA & AA/SA ratios are in g-FA/g-SA & g-AA/g-SA respectively

FIG. 28G

| | Yield (g-SA/g-GLR) | Productivity (g-SA/L/h) | Final [S.A.] (g-SA/L) | $GLR_0$ (g/L) | Residual Glycerol (g/L) | Strain |
|---|---|---|---|---|---|---|
| This study * | 0.96 | 0.23 | 26.7 | 31.0 | 3.1 | *Actinobacillus succinogenes* |
| [15] | 1.33 | 0.16 | 4.9 | 6.5 | 2.8 | *Anaerobiospirillum succiniciproducens* |
| [25] | 1.2 | 0.7 | 6.4 | 9.3 | 4.3 | DD1 strain** |

Table 8. Comparison of experimental results from different studies for the GLR-S.A. system
* These are some typical results from this study
** DD1 strain belongs to the family *Pasteurellaceae* with similarity to the genus *Manheimia*

FIG. 28H

| Chemical | Yield (mol/mol) | Productivity (g/L/h) | Final [Product] (g/L) | Microorganism | Reference |
|---|---|---|---|---|---|
| 1,3-Propanediol | 0.53 | 1.7 | 61.0 | *Klebsiella pneumoniae* | [14] |
| | 0.62 | 1.93 | 56.0 | *Clostridium butyricum* | [39] |
| Succinic acid | 0.78 | 0.26 | 28.3 | *Actinobacillus succinogenes* | This study |
| Ethanol | 0.65 | 0.033 | 4.0 | *Escherichia coli* | [16] |
| Propionic acid | 0.79 | 0.42 | 12.0 | *Propionibacterium acidipropionici* | [17] |

Table 9. Comparison of different batch bio-systems for glycerol valorisation

FIG. 28I

| Parameters | Units | Values | Description | Bounds |
|---|---|---|---|---|
| $\mu_{max}$ | $h^{-1}$ | 0.12 | Maximum specific growth rate | 0.06-0.25 |
| $K_S$ | g/l | 2.896 | Substrate saturation constant | 0.5-8 |
| $K_I$ | g/l | 15.36 | Substrate inhibition constant | 10-80 |
| $n_{SA}$ | - | 1.074 | Linearity of the SA inhibition | 0.3-1.4 |
| $a_{SA}$ | g- $P_{SA}$/g-DCW | 9.864 | Growth association constant for SA | 1.2-10.4 |
| $b_{SA}$ | g- $P_{SA}$/g-DCW h | 0.001 | Non-growth association growth for SA | 0.001-1.2 |
| $a_{FA}$ | g- $P_{FA}$/g-DCW | 0.428 | Growth association constant for FA | 0.1-2.4 |
| $b_{FA}$ | g- $P_{FA}$/g-DCW h | 0.002 | Non-growth association growth for FA | 0.001-1.2 |
| $a_{AA}$ | g- $P_{AA}$/g-DCW | 0.753 | Growth association constant for AA | 0.1-2.4 |
| $b_{AA}$ | g- $P_{AA}$/g-DCW h | 0.001 | Non-growth association growth for AA | 0.001-1.2 |
| $Y_X$ | g-DCW/g-S | 0.130 | Stoichiometric Yield of Cells to GLR | 0.01-0.8 |
| $Y_{SA}$ | g-$P_{SA}$/g-S | 2.790 | Stoichiometric Yield of SA to GLR | 0.1-4.5 |
| $m_s$ | g-S/g-DCW h | 0.001 | Specific maintenance coefficient | 0.001-0.1 |
| $P_{SA}^*$ | g- $P_{SA}$/L | 45.6 | Critical succinic acid concentration | [35] |

Table 10. Computed parameter values for the unstructured model.

FIG. 28J

| Runs | $\mu_{max}$ | $K_S$ | $K_I$ | $n_{S,A}$ | $Y_X$ | $m_s$ | $a_{S,A}$ | $b_{S,A}$ | $Y_{S,A}$ | $a_{P,A}$ | $b_{P,A}$ | $a_{A,A}$ | $b_{A,A}$ |
|---|---|---|---|---|---|---|---|---|---|---|---|---|---|
| 1 | 0.099 | 1.656 | 19.783 | 0.856 | 0.609 | 1.0E-03 | 10.556 | 1.00E-03 | 1.146 | 0.382 | 0.003 | 0.642 | 0.002 |
| 2 | 0.099 | 1.656 | 19.783 | 0.856 | 0.609 | 1.0E-03 | 10.556 | 1.00E-03 | 1.146 | 0.382 | 0.003 | 0.642 | 0.002 |
| 3 | 0.113 | 2.677 | 17.805 | 1.276 | 0.093 | 1.0E-03 | 10.097 | 1.00E-03 | 6.29 | 0.481 | 0.001 | 0.763 | 1.10E-03 |
| 4 | 0.113 | 2.677 | 17.805 | 1.276 | 0.093 | 1.0E-03 | 10.097 | 1.00E-03 | 6.29 | 0.481 | 0.001 | 0.763 | 1.10E-03 |
| 5 | 0.113 | 2.677 | 17.805 | 1.276 | 0.093 | 1.0E-03 | 10.097 | 1.00E-03 | 6.29 | 0.481 | 0.001 | 0.763 | 1.10E-03 |
| 6 | 0.113 | 2.677 | 17.805 | 1.276 | 0.093 | 1.0E-03 | 10.097 | 1.00E-03 | 6.29 | 0.481 | 0.001 | 0.763 | 1.10E-03 |
| 7 | 0.113 | 2.677 | 17.805 | 1.276 | 0.093 | 1.0E-03 | 10.097 | 1.00E-03 | 6.29 | 0.481 | 0.001 | 0.763 | 1.10E-03 |
| 8 | 0.113 | 2.677 | 17.805 | 1.276 | 0.093 | 1.0E-03 | 10.097 | 1.00E-03 | 6.29 | 0.481 | 0.001 | 0.763 | 1.10E-03 |
| 9 | 0.113 | 2.677 | 17.805 | 1.276 | 0.093 | 1.0E-03 | 10.097 | 1.00E-03 | 6.29 | 0.481 | 0.001 | 0.763 | 1.10E-03 |
| 10 | 0.113 | 2.677 | 17.805 | 1.276 | 0.093 | 1.0E-03 | 10.097 | 1.00E-03 | 6.29 | 0.481 | 0.001 | 0.763 | 1.10E-03 |
| 11 | 0.113 | 2.677 | 17.805 | 1.276 | 0.093 | 1.0E-03 | 10.097 | 1.00E-03 | 6.29 | 0.481 | 0.001 | 0.763 | 1.10E-03 |
| 12 | 0.116 | 2.415 | 16.497 | 0.981 | 8.987 | 1.0E-03 | 9.242 | 1.00E-03 | 0.908 | 0.381 | 0.003 | 0.662 | 0.001 |
| 13 | 0.116 | 2.415 | 16.497 | 0.981 | 8.987 | 1.0E-03 | 9.242 | 1.00E-03 | 0.908 | 0.381 | 0.002 | 0.662 | 0.001 |
| 14 | 0.116 | 2.415 | 16.497 | 0.981 | 8.987 | 1.0E-03 | 9.242 | 1.00E-03 | 0.908 | 0.381 | 0.002 | 0.662 | 0.001 |
| 15 | 0.116 | 2.415 | 16.497 | 0.981 | 8.987 | 1.0E-03 | 9.242 | 1.00E-03 | 0.908 | 0.381 | 0.002 | 0.662 | 0.001 |
| Average | 0.112 | 2.471 | 17.72 | 1.142 | 0.187 | 1.0E-03 | 9.93 | 1.00E-03 | 4.172 | 0.44 | 0.002 | 0.72 | 0.001 |
| S.D. | 0.005 | 0.350 | 1.019 | 0.175 | 0.209 | 0 | 0.457 | 0 | 2.692 | 0.051 | 0.001 | 0.055 | 0.001 |

Table 11. Parameter values as estimated from multiple runs

FIG. 28K

SELECTION OF IMPROVED MICROBIAL STRAINS FOR PRODUCTION OF SUCCINIC ACID FROM GLYCEROL

CROSS-REFERENCE TO RELATED APPLICATIONS

This application is the National Phase of International Application PCT/GB2012/050887, filed Apr. 20, 2012, which designated the United States and that International Application was published under PCT Article 21(2) in English. This application also includes a claim of priority under 35 U.S.C. §119(a) and §365(b) to British patent application No. 1106686.7 filed Apr. 20, 2011.

The present invention relates to methods for generating microorganisms with improved ability to convert glycerol to succinic acid. The invention also relates to microorganisms produced by such methods. The invention relates to bacteria having the properties of those deposited at the NCIMB under the Budapest Treaty on 13 Apr. 2011, and given the Accession No. NCIMB 41825. The invention further relates to a method of producing succinic acid using microorganisms as referred to above, and to succinic acid produced by this method.

Succinic acid is a compound that can be used to generate a number of commodity and specialty chemicals. Succinic acid is a C-4 linear saturated dicarboxylic acid and according to US Department of Energy it is considered to be one of the top value-added chemicals produced from biomass as it has the potential to be a key building block for the production of various chemicals. Currently, it is mainly produced form petrochemical precursors (butane) through reduction of maleic anhydride in low yields. However, it can also be produced by microbial fermentation from glucose and/or other sugars.

Recently, there have been significant increases in the production and use of bio-fuels, including biodiesel. Biodiesel production has increased worldwide from 1,000 million litres in 2000 to 6,000 million litres in 2006. According to current trends, biodiesel production will continue to increase in the following years.

The utilisation of biodiesel has environmental benefits such as lower emissions of unburned hydrocarbons, carbon monoxide and particulate matter. The most important, however, is that unlike conventional diesel it does not contain any sulphur or aromatics. Therefore, mixtures of diesel and biodiesel (up to 20%) can decrease the emissions of certain pollutants, thus, reaching the required strict specifications for transport fuels.

Biodiesel is typically produced (see Scheme 1) through the catalysed alcoholic trans-esterification of vegetable oils and/or animal fats (containing triglyceride fatty acid esters), to yield glycerol as the major by-product (typically 10% w/w). The process can be catalysed by acids, bases, or enzymes.

Scheme 1

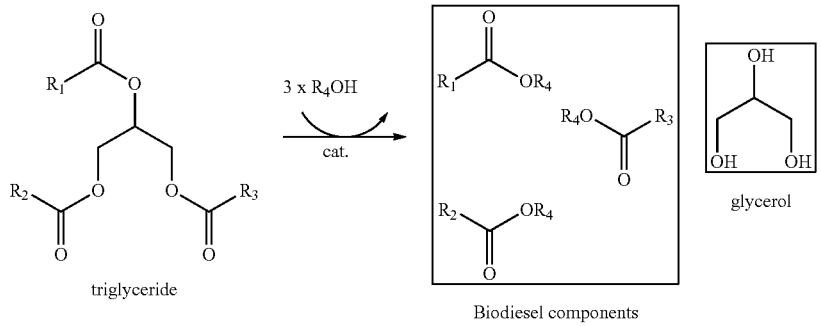

The resulting biodiesel and glycerol mixture settles on standing into two distinct liquid layers, the lower of which is termed "crude glycerol". The crude glycerol layer is readily separated from the biodiesel, for example being drawn off from the bottom of a settled mixture, or by absorption with water.

Crude glycerol contains a number of impurities, including alcohols (typically excess methanol used in the trans-esterification reaction itself), water, excess base catalyst, and soaps of non-esterified fatty acids. Crude glycerol is typically 65-80% w/w pure, but may be of lower purity depending on the biodiesel production protocols and the raw materials used therein.

The increase in production of biodiesel will result in a large glycerol surplus that current glycerol markets cannot absorb. However, the use of glycerol as a starting point for the production of succinic acid may represent a desirable use of this material (or, indeed, glycerol from other sources).

A number of studies have reported on the bioconversion of glycerol to succinic acid, but interest in this field has been restricted, since, to date, only relatively poor performances (low final product concentrations and low productivities) have been achieved. Examples of the techniques used for succinic acid production from glycerol include those employing *Anaerobiospirillum succiniciproducens* and a novel strain DD1, which belongs to the family *Pasteurellaceae*.

Although some of these techniques utilising glycerol are able to obtain yields of succinic acid that are around 1 ("yield" here being taken to refer to the amount of succinic acid produced per unit of the substrate being converted), and thus superior to the yields from glucose and/or other sugars due to the higher reduced state of glycerol, these tend to be associated with very low final product concentration (which may not exceed 19 g/L). Other techniques from the prior art are able to produce relatively high final concentrations of succinic acid (up to around 45 g/L), but only low yields (around 0.36).

It is an aim of some embodiments of the invention to generate microorganisms able to produce an increased yield of succinic acid converted from glycerol. It is an aim of some embodiments of the invention to generate microorganisms able to produce an increased final concentration of succinic acid. It is an aim of some embodiments of the invention to generate microorganisms with increased productivity in terms of the production of succinic acid. It is an aim of certain embodiments of the invention to generate microorganisms able to produce increased final concentrations and/or yields and/or productivity of glycerol. It is an aim of certain embodiments of the present invention to provide alternative processes for the bioconversion of glycerol into succinic acid. It is an aim of certain embodiments of the present invention to provide an improved process for the bioconversion of glycerol into succinic acid. It is an aim of certain embodiments of the present invention to provide improved plants for the production of succinic acid. It is an aim of certain embodiments of the present invention to provide an improved process for the downstream processing and purification of succinic acid to a crystalline form.

Training Methods

In a first aspect the invention provides a method of generating a microorganism with improved ability to convert glycerol to succinic acid, the method comprising:
a) combining a microorganism with ability to convert glycerol to succinic acid and a medium containing glycerol to produce a fermentation mixture;
b) allowing fermentation to occur such that succinic acid is produced; and
c) assaying for an indication of glycerol metabolism.

The inventors have found that the methods of the invention are able to significantly improve the abilities of microorganisms to convert glycerol to succinic acid. Merely by way of example, and as discussed in more detail below, the methods of the invention are able to markedly improve the ability of microorganisms to convert glycerol to succinic acid. The methods are able to generate microorganisms the glycerol-converting ability of which is doubled, or more, compared to their innate ability. Indeed, the methods of the invention are capable of generating microorganisms in which the ability to convert glycerol to succinic acid is more than doubled and have been used to generate microorganisms in which such activity is increased by up to 120%, and the inventors believe that even greater improvements (e.g. 150% or above) may be achieved using the methods of the invention.

Without wishing to be bound by any hypothesis, the inventors believe that fermentation in the presence of glycerol serves to "train" the microorganisms, and improves the innate ability of the microorganisms to convert glycerol to succinic acid. One "round" of training can be considered to correspond to the combination of steps "a)" and "b)" of the first aspect of the invention (thus combining the microorganism and medium to form a fermentation mixture, and then allowing fermentation to occur). Except for where the context requires otherwise, a round of training may, if desired, comprise other optional steps, as considered elsewhere in the specification. Additional rounds of training may be provided in the methods of the invention by collecting microorganisms at the end of fermentation, and repeating steps "a)" and "b)" (and any other optional steps that it is wished to employ) using the collected microorganisms until a desired number of rounds of training have been completed. In such embodiments assaying for an indication of glycerol metabolism may take place after each round of training, or after a number of rounds of training have been performed.

The "training" of the microorganisms provides a method of improving the performance of the microorganism for the particular substrate that results in microorganisms which are more stable, with harmonised internal metabolisms, than may be expected to be produced by approaches utilising genetic modification. Hence possible compatibility issues that may otherwise be expected to arise through genetic modification strategies can be avoided.

A method in accordance with this embodiment may make use of repeated incidences of training until no further improvement is noted. Alternatively, a method in accordance with this embodiment may make use of a predetermined number of rounds of selection. Such a number may, for example, be predetermined with reference to previously conducted experiments designed to identify preferred numbers of rounds of training.

Merely by way of example, a method in accordance with this first aspect of the invention may include between 4 and 19 repetitions of steps "a)" and "b)" (and optionally "c)") to provide between 5 and 20 rounds of training in total. Such a method may include between 5 and 14 repetitions of steps "a)" and "b)" (and optionally "c)") to provide between 6 and 15 rounds of training, or between 6 and 9 repetitions of steps "a)" and "b)" (and optionally "c)") to provide between 7 and 10 rounds of training.

In certain embodiments of the invention, separate fermentation mixtures may be established and allowed to ferment. The separate fermentation mixtures may be produced using microorganisms from discrete sources. Alternatively, the separate fermentations mixtures may be produced using microorganisms from a common source (such as microorganisms selected for favourable glycerol metabolism properties, in the manner discussed below).

In a suitable embodiment utilising separate fermentation mixtures, the separate fermentation mixtures are assayed for glycerol metabolism after fermentation. Microorganisms may then be selected from fermentation mixtures exhibiting favourable glycerol metabolism properties. These microorganisms can then be mixed with medium (to produce a new fermentation mixture) and fermented to provide a further round of training.

As suggested above, the embodiments described in the two preceding paragraphs may be combined, so that selected bacteria exhibiting favourable glycerol metabolism are selected and used to establish separate fermentation mixtures. These separate fermentation mixtures can then be assayed for an indication of glycerol metabolism, and microorganisms exhibiting favourable glycerol metabolism properties may be selected and used to establish separate fermentation mixtures for use in another round of training.

In certain embodiments of this aspect of the invention, each round of training may be followed by an incidence of selection. Alternatively, in other embodiments there may be multiple rounds of training between incidences of selection.

An appropriate period of fermentation may be selected with reference to the starting concentration of glycerol present in the fermentation mixture. Generally, the higher the starting concentration of glycerol employed, the longer the period of fermentation it will be appropriate to employ. For example, in an embodiment where the starting concentration of glycerol is around 10 g/L, an appropriate fermentation period may be around 30 hours. In an embodiment where the starting concentration of glycerol is around 20 g/L, an appropriate fermentation period may be around 50 hours, while in an embodiment where the starting concentration of glycerol is around 35 g/L, an appropriate fermentation period may be around 85 hours.

The period of fermentation may be substantially equal between incidences of training.

The concentration of glycerol present when establishing the fermentation mixture may be substantially equal between incidences of training.

Alternatively, the concentration of glycerol present when establishing the fermentation mixture may be increased between rounds of training. Suitable concentrations of glycerol for use in the methods of the invention are discussed in more detail below. However, and merely by way of example, the amount of glycerol may increase from about 5 g/L in a first round of training to 30 g/L in a subsequent round. The amount of any increase in glycerol in a fermentation mixture may increase by 5%, 10%, 20% or more between rounds of training.

A method in accordance with the present invention may be terminated when the level of glycerol metabolism does not significantly increase as compared to the preceding round of training.

Suitably, the assay for an indication of glycerol metabolism may be an assay for production of succinic acid. This provides a direct indication of glycerol metabolism, and specifically glycerol conversion to succinic acid, by the microorganisms.

In alternative embodiments of the invention, the assay for an indication of glycerol metabolism may be a cell growth assay. Since microorganisms for use in accordance with the invention have an ability to use glycerol as a source of metabolic carbon, they are able to use this source for replication, and so an increase in cell numbers provides an indirect indication of their glycerol metabolism. In a suitable embodiment, the growth of microorganisms can be assessed by measuring the optical density of a fermentation mixture. Alternatively, the growth of microorganisms can be assessed by measurements of the mass of dry cell weight in a known volume of a fermentation mixture (grams dry cell weight per litre: g-DCW/L), or and specific growth rates ($h^{-1}$).

The methods of the invention may optionally include a step of assaying for an indication of glycerol metabolism prior to training. This may provide a "base line" value for the untrained microorganism.

Fermentation mixtures for use in the methods of the invention (whether in accordance with the first or fourth aspect of the invention) may be produced using a relatively large inoculum of the relevant microorganism. Merely by way of example, a suitable fermentation mixture may be produced using an inoculum representing between 5 and 12% (v/v) of the total fermentation mixture. In a suitable embodiment the inoculums may represent around 10% (v/v) of the total fermentation mixture. Without wishing to be bound by any hypothesis, the inventors believe that the use of inoculums of this size is beneficial in that it decreases the lag time that would otherwise occur once a fermentation mixture has been produced.

The methods of the invention may employ any suitable form of microorganism that has an ability to convert glycerol to succinic acid. Microorganisms capable of metabolising carbon to produce succinic acid are known to those skilled in the art. Such microorganisms may be suitable for use in the methods of the invention in order to generate microorganisms with improved ability to convert glycerol to succinic acid.

Merely by way of example, such a microorganism may comprise a bacterium or yeast. A suitable example of a bacterium suitable for use in the methods of the invention is *Actinobacillus succinogenes*. The strain of *Actinobacillus Succinogenes* given the American Type Culture Collection (ATCC) Number 55618 is a succinic acid-generating microorganism isolated from bovine ruminal contents. *Actinobacillus succinogenes* having ATCC No. 55618 was previously deposited by a third party. IMI CC No. 505731 is the same *Actinobacillus succinogenes* strain as ATCC No. 55618. IMI CC No. 505731 was deposited on Jun. 28, 2016, by The University of Manchester, at IMI Culture Collection at the Centre for Agriculture and Biosciences International (CABI), being an International Depository authority recognized by Budapest Treaty. However, it has previously been thought that glycerol would not constitute a suitable source of metabolic carbon to be used in such methods, since it has previously been thought that glycerol inhibits the growth and viability of this strain of bacteria. The strain of *Anaetobiospirillum succiniciproducens* deposited under ATCC No. 55617 represents another example of a suitable bacterium for use in the methods of the invention. *Anaetobiospirillum succiniciproducens* having ATCC No. 55617 was also previously deposited by a third party. Suitable yeasts for use in accordance with the invention include *Saccharomyces cerevisiae*.

The inventors have found that the methods of the invention are able to generate microorganisms having improved ability to convert glycerol to succinic acid, as compared to the ability of the "untrained" microorganism (that is to say examples of the microorganism with an innate ability to convert glycerol to succinic acid that have not been trained with the methods of the invention, and so have not been subjected to improvements in this manner). This improved ability, acquired after training, may be assessed with reference to one or more of the following criteria:

Yield of succinic acid that the microorganism is able to produce;

Final concentration of succinic acid that the microorganism is able to produce; and Productivity of the microorganism.

For present purposes, "yield" may be determined with reference to the amount of succinic acid produced per unit of glycerol (e.g. grams of succinic acid per gram of glycerol: g-SA/g-Glycerol). The final concentration of succinic acid that microorganisms in accordance with the invention are able to produce may be quantified, for instance, as grams of succinic acid per litre (g-sa/L). "Productivity", for the purposes of this disclosure, may be determined with reference to the mass of succinic acid produced by a given volume of a fermentation mixture over a period of time (e.g. g-SA/L/h).

Merely by way of example, the inventors have found that the methods of the invention are able to generate microorganisms capable of producing yields increased by up to 50% as compared to the untrained microorganisms. The methods of the invention are able to generate microorganisms capable of producing a final concentration of succinic acid that is up to 60% greater than can be achieved using the untrained microorganisms. Furthermore, the methods of the invention can be used to generate microorganisms the productivity of which is improved by up to 120% as compared to the untrained microorganism.

The microorganisms generated in accordance with the invention (and the methods of the invention employing such microorganisms) are able to produce large quantities of succinic acid from the available glycerol. Merely by way of example, the methods of the invention are able to produce around 0.7 g of succinic acid per gram of glycerol, and indeed can be used to produce yields of up to 1.12 g of succinic acid per gram of glycerol.

Methods in accordance with this first aspect of the invention may make use of fermentation mixtures in which the glycerol is present at an initial concentration of between 5 g/L and 60 g/L. Merely by way of example, a suitable embodiment may make use of a starting concentration of between 10 g/L and 25 g/L glycerol.

Methods in accordance with this first aspect of the invention may be used to generate microorganisms that are able to produce concentrations of succinic acid that are up to three times higher than those that can be achieved using prior art methods in which glycerol is bio-converted into succinic acid. For example, microorganisms generated in accordance with this aspect of the invention may be able to produce fermentation products containing succinic acid at a final concentration of 20 g/L, 25 g/L, 28 g/L, 32 g/L or more.

It may be preferred that methods in accordance with the first aspect of the invention utilise glycerol from a source other than crude glycerol.

The effectiveness of the methods of the invention is surprising given that both glycerol (the substrate for conversion) and succinic acid (the product of fermentation) have been reported to act as inhibitors to microorganism growth. It might be expected that either the high levels of glycerol found at the beginning of fermentation in the methods of the invention, or the increasing concentration of succinic acid produced during the course of fermentation, would inhibit the biological activity of the microorganisms, and hence their ability to convert glycerol to succinic acid.

It is highly beneficial that the methods of the invention are able to avoid this problem. Furthermore, it is highly beneficial that the microorganisms generated by methods in accordance with this aspect of the invention are able to avoid this problem, since it facilitates their use in methods for producing succinic acid from glycerol.

Once sufficient training has been undertaken, and a required improvement in the ability to convert glycerol to succinic acid has been achieved, the improved microorganisms may then be collected. Further training can then be avoided as unnecessary. Indeed, the inventors believe that further training may be associated with a decrease in the ability of the glycerol-converting ability of microorganisms. The inclusion of step "c)" after a number of rounds of training (or, in certain embodiments, each round of training) allows the effectiveness of these training rounds to be assessed, and excess rounds (which may give rise to decreased glycerol-converting activity) to be avoided.

Microorganisms

In a second aspect the invention provides microorganism with improved ability to convert glycerol to succinic acid, produced by a method in accordance with the first aspect of the invention. Such a microorganism may be produced in accordance with any of the embodiments of this aspect of the invention.

In a third aspect the invention provides a bacterium deposited at the NCIMB under the Budapest Treaty on 13 Apr. 2011, and given the Accession No. NCIMB 41825. This bacterium has been produced by the inventors using the methods of the first aspect of the invention (as described in the accompanying experimental results) to train the strain of *Actinobacillus succinogenes* deposited under ATCC No. 55618. These bacteria deposited under the Accession No. NCIMB 41825 are well suited to use in methods for converting glycerol to succinic acid.

Microorganisms exhibiting improved ability to convert glycerol to succinic acid, such as those in accordance with the second or third aspects of the invention, may be used in methods for the production of succinic acid from glycerol. These microorganisms may be collected at the end of a method in accordance with the first aspect of the invention.

Microorganisms in accordance with the invention are able to produce final concentrations of succinic acid that are relatively high, while also achieving good yields. For example, microorganisms generated by methods in accordance with the first aspect of the invention, and used in methods in accordance with the fourth aspect of the invention, are able to produce final concentrations of up to 32 g/L (with higher values in the region of 60-70 g/L believed to be obtainable) with yields of around 1. In contrast, prior art techniques able to produce comparable yields have produce maximum concentrations of about 19 g/L, while prior art techniques able to achieve high final concentrations (up to around 45.5 g/L) have done so only at much lower yields (around 0.36). Thus it can be seen that the microorganisms in accordance with the present invention (which may be produce by methods of the first aspect of the invention) provide significant advantages over the prior art (for example in their use in methods of the fourth aspect of the invention).

Fermenting Methods

In a fourth aspect the invention provides a method of producing succinic acid from glycerol, the method comprising:

a) mixing a microorganism in accordance with the present invention, having the ability to convert glycerol to succinic acid, and a medium comprising glycerol to produce a fermentation mixture; and b) incubating the fermentation mixture, under conditions that promote fermentation to produce succinic acid, until succinic acid is produced.

In accordance with this aspect of the present invention, production of succinic acid is affected in a fermentation mixture comprising glycerol and an appropriate microorganism. The fermentation mixture may also comprise any nutrients necessary to feed the fermentation process. The process of fermentation within this mixture yields a fermentation product comprising succinic acid (and/or succinate salts thereof).

Methods in accordance with this fourth aspect of the invention may be used to produce fermentation products containing concentrations of succinic acid that are higher than those obtainable in prior art methods providing comparable yields. For example, the methods of the invention may be used to achieve concentrations that are up to twice, or preferably even up to three times, as high as those that can be achieved using prior art methods based on the bioconversion of glycerol. For example, methods in accordance with this aspect of the invention may produce fermentation products containing succinic acid at a final concentration of 20 g/L, 25 g/L, 28 g/L, 32 g/L or more.

The above final concentrations can be achieved at yields of up to 0.7, 1, 1.2 or more. Previously, such high final concentrations were only able to be achieved at much lower yields. Without wishing to be bound by any hypothesis, the inventors believe that the conversion of glycerol to succinic acid in the methods of the invention may proceed by the following scheme:

Scheme 2

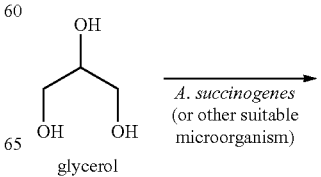

glycerol

-continued

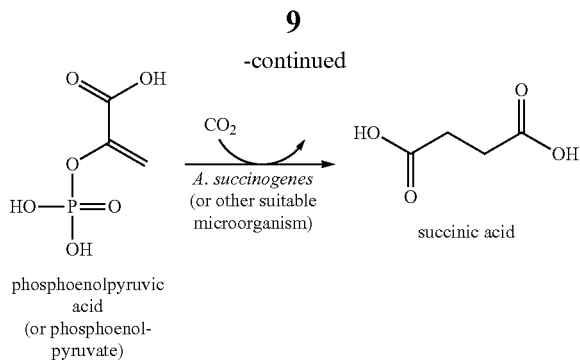

phosphoenolpyruvic acid
(or phosphoenol-pyruvate)

A number of by-products are also produced, and these may lead to impurities in the fermentation product that are characteristic of the way in which it has been produced (as discussed further below).

The glycerol to be used in the methods in accordance with this aspect of the invention may be in the form of "crude" glycerol, which may be obtained from a variety of different sources. Merely by way of example, suitable crude glycerol may be obtained as a by-product of the production of biodiesel. Such crude glycerol may be directly obtained from the biodiesel production process, and in certain embodiments may be used without further purification following any separation from biodiesel. Such crude glycerol will generally contain contaminants, which may be characteristic of the manner in which it has been produced.

By way of example, contaminants that may be found in crude glycerol include alcohols, such as methanol. Crude glycerol suitable for use in the methods of the invention may comprise crude glycerol containing methanol at a proportion of up to approximately 20% (w/w). The crude glycerol suitably comprises 0.1-20% w/w of an alcohol, suitably 1-15% w/w, suitably 5-12% w/w. The concentration of glycerol within crude glycerol may vary. Though typically in the region of 55-80% w/w, the crude glycerol may suitably comprise 40-95% w/w glycerol, suitably 70-90% w/w, suitably 80-88% w/w. It will be appreciated that the concentration of glycerol in crude glycerol is one of the factors that can influence the concentration of glycerol within a fermentation mixture.

In certain embodiments the medium comprising glycerol may comprise glycerol produced in the production of biodiesel.

In certain embodiments the medium comprising glycerol may further comprise one or more of the following impurities: methanol; fatty acid methyl esters; mono-glycerides; and di-glycerides. As shown in Experimental Results reported elsewhere in this specification, sources of glycerol that comprise impurities of this sort have proven to be particularly effective in promoting growth of microorganisms of the invention. Accordingly, media comprising glycerol in the presence of such impurities may represent preferred constituents for use in the generation of succinic acid using the microorganisms and/or methods of the invention.

Conditions that may be varied and/or controlled in methods of the invention in order to promote fermentation include:
  Buffering;
  $CO_2$ flow rate;
  Temperature;
  Agitation speed;
  Head space (within vessels containing a fermentation mixture); and
  Mixing baffles within vessels in which fermentation occurs As the fermentation mixture ferments, and acidic products form, the pH tends to decrease. If the reaction mixture reaches a sufficiently low pH this can detrimentally influence the activity of the microorganisms converting glycerol to succinic acid. As such, the pH of the fermentation mixture is suitably controlled throughout the fermentation process. The pH is suitably controlled to be between pH 6.4 and 7.2.

pH is suitably controlled via the presence in the fermentation mixture of a buffer system. Any suitable buffer system may be employed. However, carbonate buffers may represent preferred buffer systems. Suitable carbonate buffers include carbonates, hydrogen carbonates, or a combination thereof. Any suitable counterion may be employed within the buffer systems. Preferred counterions include alkali or alkaline earth metals. Suitably the counterion is magnesium, sodium or potassium.

Suitable fermentation mixtures may also comprise other components (such as phosphates) that may provide some buffering while also serving other functions (such as nutrition of the microorganisms). Examples of such components include phosphates, hydrogen phosphates, dihydrogen phosphates, or a combination thereof. Suitably the buffer system comprises a phosphate buffer comprising a mixture of sodium dihydrogen phosphate ($NaH_2PO_4$) and sodium hydrogen phosphate ($Na_2HPO_4$).

In suitable embodiments the buffer system may comprise a metal carbonate or hydrogen carbonate. In preferred embodiments, the buffers system may comprise an alkali or alkaline earth metal carbonate or hydrogen carbonate. The buffer system may suitably comprise a sodium, potassium, magnesium, or calcium, carbonate or hydrogen carbonate. In a particular embodiment, the buffer system may comprise magnesium carbonate ($MgCO_3$). The fermentation mixture suitably comprises 1-40 g/L of a buffer component such as magnesium carbonate, suitably 2-35 g/L, suitably 10-30 g/L.

The concentration of carbon dioxide in the fermentation mixture can impact upon the fermentation process. The inventors believe it is advantageous to ensure that fermentation is conducted in the presence of carbon dioxide. In such embodiments incubation conditions are used that serve to provide carbon dioxide in the fermentation mixture. These conditions may include conducting fermentation in conditions where the headspace (the difference between the volume of the vessel in which fermentation occurs and the volume of the fermentation mixture) favours mixing of the fermentation mixture with carbon dioxide. Merely by way of example, the inventors have found that the use of a fermentation mixture that has a volume approximately 70% of that of the fermentation vessel (so that the headspace is approximately 30%) may be used to promote adequate mixing of the fermentation mixture with carbon dioxide.

Appropriate addition of carbon dioxide may also be of benefit in establishing and maintaining pH levels that promote fermentation. Appropriate levels of carbon dioxide may also promote the production of succinate from the intermediate PEP (illustrated in Scheme 1).

Suitable flow rates of carbon dioxide that may be provided to fermentation mixtures in the methods of the invention may be in the region of 0.001 L/minute to 0.3 L/minute corresponding to 0.015-0.002 volume CO2 gas/volume fermentation broth/min. These ranges are suitable for use in reaction mixtures of between 0.1 L and 150 L volumes. In the case of larger reaction mixture, for example reaction mixtures in the order of 3000 L, flow rates of $CO_2$ should be scaled up accordingly.

Surprisingly, the inventors have found that the amount of $CO_2$ provided in methods of the invention does not proportionally scale-up as reactor vessels increase in size. Merely by way of example, $CO_2$ may be provided to a 2 L reaction vessel at a rate of approximately 10 ml $CO_2$ per minute, while $CO_2$ may be provided to a 10 L reaction vessel at a rate of less than 20 ml $CO_2$ per minute. The inventors believe that in suitable embodiments of the methods of the invention $CO_2$ may be provided to a 150 L reaction vessel at a rate of between approximately 20 and 300 ml $CO_2$ per minute.

Without wishing to be bound by any hypothesis, this may be linked to the inventors' surprising finding that accumulation of $CO_2$, which may otherwise be expected to act as a useful carbon source, significantly decreases the growth of microorganisms of the invention, and so reduces the efficiency of methods of the invention for the production of succinic acid. Accordingly, in certain embodiments of the invention it be preferred that restriction of provision of $CO_2$. Increased $CO_2$ flow rates can increase the pressure of the head space, thus increase the concentration of $CO_2$ in the mixture. This increase may result in a decrease of the growth of the microorganism. Hence, it may be preferred that $CO_2$ flow rates be controlled to relatively low levels (see above instances of appropriate $CO_2$ flow rates).

Such controlled rates of CO2 flow, able to promote growth of microorganisms of the invention within a reaction mixture, may constitute a part of the conditions that promote fermentation to produce succinic acid utilised in methods of the invention. Such embodiments provide a number of advantages. These include increasing the amount of succinic acid that may be produced (since such methods avoid inhibiting growth or activity of the succinic acid-producing microorganisms), reducing costs (since less $CO_2$ need be provided) and reducing waste or other harmful environmental impact of the methods.

Methods in accordance with the invention may maintain the fermentation mixtures at a temperature of approximately 37° C. Such temperatures are able to promote fermentation, since they may support the succinic acid-generating activity of microorganisms.

The time for which a fermentation mixture is incubated in the methods of the invention may be selected with reference to the initial concentration of glycerol present in a fermentation mixture. Merely by way of example, suitable periods for fermentation may be between approximately 24 hours and approximately 120 hours. More specifically, for fermentation mixtures comprising an initial glycerol concentration of approximately 10 g/L, an incubation time of approximately 30 hours may be employed. For fermentation mixtures comprising an initial glycerol concentration of approximately 20 g/L a suitable length of fermentation may be around 50 hours. In embodiments using a fermentation mixture with an initial concentration of 35 g/L a suitable length of fermentation may be in the region of 85 hours.

Methods in accordance with the present invention may preferably involve stirring of the fermentation mixture. This may be of benefit in avoiding local conditions that do not serve to promote fermentation. Merely by way of example, the fermentation mixture may be stirred at a rate of around 200 rpm to 400 rpm. The stirring may be practiced with multiple stirring devices, suitably proportioned to achieve the level of mixing required.

However, the inventors have found that excessive stirring may have deleterious effects on the production of succinic acid. Without wishing to be bound by any hypothesis, the inventors believe that excessive stirring may break down beneficial cell pairings between microorganisms of the invention. Accordingly, in certain embodiments of the methods of the invention stirring may be limited to a rate that does not break up cell pairings. It will be appreciated that suitable stirring rates for use in such embodiments may vary with reference to factors such as the size of the fermentation vessel, but that rates meeting this requirement may be determined experimentally by sampling fermentation mixtures stirred at different rates, and assessing whether or not cell pairings are retained among the microorganisms.

Methods in accordance with this aspect of the invention may make use of batch, semi-batch or continuous culture conditions under which fermentation may take place. The methods may be adapted with reference to the specific form of culture adopted. Merely by way of example, continuous culture conditions will tend to employ cultures in which microorganisms are immobilized. Initial concentrations of glycerol, carbon dioxide levels and fermentation times may all be adapted as required.

Medium

A medium suitable for use in the methods of the invention should provide sources of carbon (C), nitrogen (N) and phosphorous (P) that may be used by the microorganisms for metabolism within the fermentation mixture. Since the medium will generally be the major component (as compared to the inoculums) in establishing the fermentation mixture, it will generally be desirable that the medium be the major source of these components.

In a fifth aspect, the invention provides a medium for growth of glycerol-converting microorganisms in culture. The medium may contain sources of metabolic carbon, nitrogen and phosphorous provided in an amount such that when the medium is added to an inoculums to form a fermentation mixture, the respective concentrations of these components within a fermentation mixture may be in the region of:

C: 2-20 g/L
N: 2.5-5 g/L
P: 0.3-0.5 g/L

In a suitable embodiment, the ratio of C:N:P may be 35:15:1. P may be provided at a concentration of approximately 0.34 g/L.

The medium may comprise sources of metabolic carbon, nitrogen and phosphorous, for example along the lines discussed above. The inventors have found that the use of media in which C, N and P are provided in a proportion such that when a fermentation mixture is produced these components are provided within these limits provides a number of advantages. One major advantage that the inventors have identified in connection with the media of the present invention is the finding that these are able to employ much less nutrients than do media described in the prior art. Prior art media able to support glycerol-converting microorganisms have used both organic and inorganic metabolic nitrogen sources. The media of the invention are able to promote fermentation even if only organic sources of metabolic nitrogen are used. A further distinction is that prior art media have employed $K_2HPO_4$ while the media of the invention employ salts of sodium phosphate. Furthermore, prior art media have made use of additional nutrients, such as sodium fumarate, bactopeptone, and cornsteep liquor. None of these are required in the media of the invention, which are able to employ glycerol as the sole source of metabolic carbon, as set out below.

There are various ways in which suitable media comprising metabolic carbon, nitrogen and phosphorous in the requisite proportions can be produced. Examples of these are considered below.

The glycerol component of the medium represents a suitable source of metabolic carbon in the fermentation mixture. In certain embodiments glycerol may represent the major source of metabolic carbon in the fermentation mixture and the major source of carbon in the medium. Indeed, in preferred embodiments of the invention glycerol may comprise substantially the sole carbon source provided in the fermentation mixture and in the medium.

In other embodiments a fermentation mixture may include a number of sources of metabolic carbon. In such embodiments of the invention a suitable medium may comprise glycerol and one (or more) other carbon sources. Suitable examples of such further carbon sources may include sucrose, fructose and xylose.

Metabolic nitrogen may be provided in any suitable source known to those skilled in the art. As mentioned above, it is a surprising finding that the media and methods of the invention need only contain relatively small amounts of nutrients, including metabolic nitrogen. Examples of suitable sources of metabolic nitrogen include: inorganic nitrogen sources, such as ammonium sulphate (which may be used in "defined" media); and yeast extract (which may be used in "semi-defined" media).

It may be desired that the same metabolic nitrogen source be used in both the methods of the first and fourth aspects of the invention (i.e. a microorganism to be used in fermentation using a defined medium may be trained in a method employing a defined medium; while a microorganism to be used in fermentation using a semi-defined medium may be trained in a method employing a semi-defined medium). A suitable yeast extract may comprise approximately 50% nitrogen (w/w). Thus a fermentation mixture may comprise between 5 g/L and 10 g/L of such a yeast extract to provide between 2.5 g/L and 5 g/L metabolic nitrogen.

It will be appreciated that the relative amounts of a source of metabolic nitrogen (such as yeast extract) and a source of metabolic carbon (such as glycerol) may be varied in order to maintain a ratio along the lines set out above. For example, in a fermentation mixture or medium containing 30 g/L glycerol, a suitable amount of yeast extract may comprise 10 g/L.

While it may be preferred to limit the sources of metabolic nitrogen along the lines set out above, the invention may also encompass embodiments that make use of alternative or further sources of metabolic nitrogen, such as polypeptone (which may serve as a source of both metabolic nitrogen and metabolic carbon).

A suitable medium may also comprise various constituents other than metabolic carbon, nitrogen and phosphorous that are beneficial to the growth and glycerol-converting activity of the micro-organisms. A medium of the invention may contain $MgCO_3$ in a concentration such that when added to an inoculum to produce a fermentation mixture a concentration of between 2-30 g/L $MgCO_3$ is produced.

A fermentation mixture or medium suitable for use in the methods of the invention may comprise $CO_3$ at a concentration of between 2-30 g/L. Alternatively, a fermentation mixture or medium suitable for use in the methods of the invention may comprise $NaHCO3$ at a concentration of between 2-30 g/L.

The action of microorganisms within the fermentation mixture gives rise to a fermentation product comprising succinic acid. The fermentation product may also comprise a number of other compounds produced by bacteria during incubation.

By way of example, the fermentation product may suitably comprise, as a weight ratio, 1:1 to 40:1 succinic acid/acetic acid, suitably 2:1 to 30:1, suitably 5:1 to 20:1.

In certain embodiments of the invention, the fermentation product suitably comprises, as a weight ratio, 50:1 to 500:1 succinic acid/pyruvic acid, suitably 100:1 to 300:1, suitably 150:1 to 250:1.

In suitable embodiments of the invention the fermentation product may comprise, as a weight ratio, 1:1 to 40:1 succinic acid/formic acid, suitably 2:1 to 30:1, suitably 5:1 to 20:1.

The fermentation product suitably comprises, as a weight ratio, greater than 200:1 succinic acid/ethanol, suitably greater than 500:1, suitably greater than 1000:1. The fermentation product is suitably (substantially) free of ethanol.

The fermentation product suitably comprises, as a weight ratio, greater than 200:1 succinic acid/lactic acid, suitably greater than 500:1, suitably greater than 1000:1. The fermentation product is suitably (substantially) free of lactic acid.

The fermentation product suitably comprises, as a weight ratio, greater than 200:1 succinic acid/fumaric acid, suitably greater than 500:1, suitably greater than 1000:1. The fermentation product is suitably (substantially) free of fumaric acid.

The fermentation product suitably comprises, as a weight ratio, greater than 100:1 succinic acid/glycerol, suitably greater than 200:1, suitably greater than 300:1. This ratio of succinic acid to residual glycerol is related to the initial glycerol concentration present. For example, in cases where the initial glycerol concentration is between 5-35 g/L, the ratio of succinic acid to glycerol may be around 200:1 or higher. In embodiments employing higher initial glycerol concentrations, the level of residual glycerol may be higher, and so the ratio of succinic acid to residual glycerol may be smaller.

Product

The fermentation product contains succinic acid that may be used in a number of applications, including commercial and industrial uses. In a sixth aspect, the invention provides succinic acid produced by a method in accordance with the present invention. Succinic acid in accordance with this aspect of the invention may be provided in the form of a succinic acid solution. Succinic acid in accordance with this aspect of the invention may be provided in the form of a salt. Merely by way of example, such a succinic acid solution may comprise the fermentation product referred to above. In the case that succinic acid in accordance with the invention is released into a medium comprising a source of magnesium ions, such as magnesium carbonate, the succinic acid may be provided in the form of magnesium succinate.

For the avoidance of doubt, in the context of the present invention, release of succinic acid from a microorganism of the invention should be taken as encompassing both active and passive methods by which succinic acid may be released.

It will be appreciated that, prior to any subsequent purification steps that may be considered desirable, succinic acid in accordance with this aspect of the invention may be associated with certain other by-products that may help to identify the method by which the succinic acid has been produced. Thus succinic acid in accordance with this aspect of the invention may be identified and distinguished from succinic acid produced by a different method. Merely by way of example, succinic acid in accordance with this aspect of the invention may be provided in the form of a solution comprising one or more of the following constituents:

Acetic acid (at a concentration of less than 1%, or up to approximately 0.5-7 g/L)

Formic acid (at a concentration of less than 0.75%, or up to approximately 0.1-5 g/L)

Pyruvic acid (at a concentration of up to approximately 0.05 g/L)

These constituents may be found at the above concentrations in a solution that comprises up to approximately 45 g/L succinic acid produced in accordance with the invention.

Furthermore, succinic acid in accordance with this aspect of the invention may be identified by virtue of its lack of by-products described as being produced by other manufacturing methods known to those of skill in the art. The inventors have found that a solution comprising up to approximately 45 g/L succinic acid produced in accordance with the invention may be substantially free from one or more of the following by-products:

Ethanol
Lactic acid
Fumaric acid

The finding that fermentation products comprising succinic acid in accordance with the present invention may be substantially free of ethanol and/or lactic acid is quite surprising, and may be of particular use in distinguishing solutions comprising succinic acid in accordance with the present invention from succinic acid produced according to prior art means. That succinic acid in accordance with the present invention may be substantially free of such by-products may be advantageous in that it obviates the need to remove these substances from the succinic acid produced. Furthermore, the reduced levels of by-products is indicative of the improved specificity of the microorganisms and methods of the invention, and improved yields that may be produced, since less of the initial substrate is converted into these unwanted compounds.

A suitable succinic acid product may be produced by purification of the fermentation product. Suitable purification may, for example, be by means of reactive extraction techniques, vacuum distillation and crystallisation. The succinic acid product suitably comprises 80-100% w/w succinic acid, suitably 90-100% w/w, suitably 95-100% w/w. It will be appreciated that the purified succinic acid produce may contain one or more byproducts identified above.

In a sixth aspect, the invention provides a succinic acid producing plant, the plant comprising: a facility in which glycerol can be produced; and
a fermentation apparatus in which the glycerol produced by said facility can be fermented with microorganisms capable of converting glycerol to succinic acid, such that succinic acid is produced.

The facility in which glycerol can be produced may be a biorefinery, such as a biodiesel manufacturing facility. A plant in accordance with this aspect of the invention may utilise crude glycerol for conversion to succinic acid.

The microorganisms capable of converting glycerol to succinic acid may be microorganisms in accordance with the present invention. Such microorganisms may be provided within the fermentation apparatus of the plant.

The process by which glycerol is fermented with microorganisms to produce succinic acid may be a method in accordance with the fourth aspect of the invention. The fermentation apparatus may be provided with means by which conditions that promote fermentation may be supported, as considered above.

The benefits that may be provided by such succinic acid producing plants, as well as factors that may be relevant in the design and running of such plants, are considered further below.

DEFINITIONS

In the context of the present invention, the term "glycerol metabolism" should be taken as referring to a biological process in which a microorganism converts glycerol to succinic acid. Unless otherwise stated, any reference to an acid product derived from digested glycerol may also include any acid-salt thereof.

References to "methods of the invention" may be taken, except where the context requires otherwise, as encompassing both methods in accordance with the first aspect of the invention, and methods in accordance with the fourth aspect of the invention.

A. Commercial Advantages of Succinic Acid Producing Plants in Accordance with the Invention In the following paragraphs, the inventors explore the concept of integrated biorefineries, and examine alternative schemes for the co-production of biofuels (biodiesel) and chemicals (succinic acid). Four different biorefinery schemes considering the different uses of crude glycerol from the biodiesel process are simulated and compared: (i) the disposal of crude glycerol as a waste (ii) the purification (through distillation) of crude glycerol to 80%, (iii) the purification of glycerol to 95% and (iv) the production of succinic acid from glycerol through fermentation. For the latter, we consider the bioprocess that converts the glycerol to succinate, and a downstream separation process that purifies and crystallises our product to the final succinic acid crystals. To apply complex kinetics for the fermentation we have linked Aspen Plus (2006.5) with Matlab (R2007b), where we have used the experimentally-based unstructured model from Vlysidis, Binns, Webb, and Theodoropoulos, 2011. We first determine the operating parameters of the fermenter that have a significant effect on the economics of this scenario, i.e the cycle time of the batch fermentation and the water flowrate entering the bioreactor. Subsequently, we perform single- and multi-objective optimisation to maximise the profit and/or to minimise the environmental impact of the overall process. We then analyse and compare the economics of the four different biorefinery schemes by using well-known profitability and/or emission criteria. Furthermore, we carry out sensitivity analysis that takes into consideration price variations for the most important materials and we extract firm conclusions about the profitability of each scenario. It is found that succinic acid co-production can enhance the profit of the overall biorefinery by 60% for a 20 years plant lifetime. These results indicate the importance of glycerol when it is utilised as a key renewable building block for the production of commodity chemicals.

List of Abbreviations
BMC Bare Module Cost
CEPCI Chemical Engineering Plant Cost Index
DPBP Discounted Payback Period
FAME Fatty Acid Methyl Esters
FCI Fixed Capital Investment
IRR Internal Rate of Return
NPV Net Present Value
PBP Payback Period
ROI Return On Investment
USP glycerol Pure Glycerol according to the specifications of United States Pharmacopeia A1. Introduction Nowadays, the quest for alternative energy sources to meet the growing global energy demands is continuously rising, as the population and prosperity levels increase worldwide [1.1]. Although fossil fuels seem to be sufficient as an energy source for more than 50 years due to the discovery and exploitation of new oil and gas reserves, they are eventually due to be depleted [1.1]. Moreover, the extensive use of petroleum, coal, and natural gas has caused a number of environmental issues with global warming being the most crucial [1.2]. Therefore, in addition to finding ways to meet the increasing energy demand we also need to decrease the environmental impact that energy usage is associated with. Renewable resources such as the sun, wind, water and biomass can partially replace fossil fuel consumption to meet the global energy demand while simultaneously decreasing the environmental impact [1.2].

Similar issues exist in the transportation sector where the market is governed by petroleum derivatives such as gasoline, kerosene and diesel. In the last decades, there has been a large increase in energy consumption and demand worldwide as the number of cars, airplanes and freight transport have greatly increased [1.3]. Alternative renewable fuels are bioethanol and biodiesel which are produced from biomass. Although these biofuels constitute only a small fraction of the total fuel produced for transportation, recently, they have been receiving increasing interest worldwide [1.3]. Many governments in the EU have imposed directives and have instituted legislations promoting the production and use of biofuels [1.4], while in the US similar targets are in place [1.5]. The aim is to reduce the dependence on petroleum through the use of nationally/regionally/locally produced biofuels, while simultaneously reducing greenhouse gas emissions [1.4]. Although, global bioethanol production is much higher [1.6] than that of biodiesel, the latter is mainly supported in the EU and its production has increased from 0.8 Mt to 21.9 Mt [1.7] with the EU producing 65% of the world's biodiesel in 2009 [1.8]. Biodiesel is produced from triglycerides derived mainly from vegetable oils or animal fats. Recently, new oil production methods have been investigated such as oil produced from algae [1.9] and oleaginous yeasts [1.10] indicating new sources of biodiesel which, contrary to energy crops, do not conflict with the cultivation of land for food; therefore they can offer alternatives to the food vs. fuels land use [1.11]. Biodiesel has been thoroughly tested and can be used as an alternative fuel in both boilers and internal combustion engines either in a pure form or blended with petroleum-based diesel [1.12].

As the popularity of biodiesel increases a number of techno-economic studies on biodiesel plants have been carried out in order to examine their economic potential and profitability. Zhang and co-workers have designed and simulated in HYSYS® four different scenarios of biodiesel processes involving two different feedstocks (virgin vegetable oil and waste cooking oil) catalysed by two different catalysts (alkali and acid catalyst). They have technically and economically assessed and compared these schemes. Also, they have performed sensitivity analysis and they have indicated that the capacity and the prices of feedstock and products have a great impact on the plant's profitability [1.13, 1.14]. A similar study has been carried out by Marchetti, Miguel and Errazu, who have studied and compared the economic viability of three biodiesel scenarios that use different catalysts by using the process simulation software SuperPro Designer® [1.15]. Apostolakou, Kookos, Marazioti and Angelopoulos have examined the profitability of an alkali catalysed biodiesel plant simulated in HYSYS® for different capacities. They propose that plant capacities greater than 50 kt/year are more attractive to investors [1.16]. Singhabhandhu and Tezuka have carried out an extensive techno-economic study for biodiesel applied in a real industry in Japan. They have estimated the profitability of the plant by incorporating a glycerol purification process and have compared it with the original scenario. They have also considered different plant costings and governmental subsidies plans [1.17]. A. West, Posarac and Ellis [1.18] have investigated four different catalytic processes for biodiesel production through HYSYS simulations. They have concluded that the process using a heterogeneous acid catalyst is the only profitable one. Haas, McAloon, Yee and Foglia [1.19] have used ASPEN PLUS® to construct a model of a biodiesel plant and have performed economic analysis of the resulting production cost. They have seen that these costs are significantly affected by the glycerol market. Finally, Binns, Vlysidis, and Theodoropoulos apart from simulating a biodiesel plant, have performed optimisations studies in terms of economics to find optimum parameter values of the methanol recovery ratio and methanol flow rate for the transesterification unit [1.20].

Most of the above studies underline the high cost of the oil raw materials (except for the cooking oil) and thus illustrate the disadvantage of biorefineries against conventional petroleum refineries. Biodiesel production costs more than petroleum diesel and in order to be competitive it is subsidised by governments or it is exempt from excise taxes [1.3], [1.12], [1.17]. A feasible way to increase the economic sustainability of the biodiesel industry is to valorise its by-products. In addition to the biodiesel there are also significant quantities of glycerol, which is the main by-product, amounting to 10% w/w of the biodiesel produced. The produced glycerol is known as crude glycerol as it is extracted together with impurities including mainly methanol and soaps; hence it has purity of only 50-80% w/w [1.21]. Purification of this glycerol could be an acceptable solution however the increased global production of biodiesel will unavoidably lead to an oversupply and a subsequent price drop for glycerol [1.17] [1.22].

Many studies have, therefore, focused on novel technologies to valorise the main biodiesel by-product stream (see [1.22] [1.23] and references within). A number of options have been investigated using glycerol for the production of various chemicals using catalysts and biocatalysts like 1,3-propanediol [1.22]. Moreover, new bioroutes have been explored such as the routes to succinic acid [1.24] [1.25] and ethanol production [1.26] that use glycerol as a key renewable feedstock.

Succinic acid can be used as a building block for a number of commodity and specialty chemicals [1.27], which makes it a very interesting platform intermediate. Currently, succinic acid occupies a rather small market mainly for specialty chemicals as its formation through the reduction of maleic anhydride demonstrates low yields [1.27]. However, its production is expected to increase, since its bioconversion from sugars is a viable route, thus its market can be expanded to commodity application chemicals [1.27]. A succinic acid biorefinery strategy has been developed previously by Du., Lin, Koutinas, Wang, Dorado and Webb who have produced a generic feedstock that can support a bacterial succinate production by utilising the nutrients of wheat [1.28].

Apart from the various economic analyses of biodiesel production the most relevant (to this study) of which are reviewed above, there are works that have examined the environmental impact of the biodiesel process and have compared it with the one of conventional diesel [1.12], [1.29], [1.30]. Furthermore, Azapagic and Clift have studied under the scope of life cycle analysis how to environmentally improve integrated systems. The authors have developed a multi-objective optimisation approach that optimises the profits of a plant by simultaneously constraining the environmental factor to the desired levels [1.31].

In this paper, we explore how a biorefinery can benefit from the co-production of fuels and chemicals. We simulate and compare four typical biodiesel scenarios that (i) dispose of or purify the glycerol to (ii) 80% and (iii) 95% with (iv) an integrated case that produces biodiesel and succinic acid. We analyse and compare the four schemes using economic and environmental indicators and we use single and multi-objective optimisation to determine the best configurations for the production of succinic acid.

A2. Plant Investment, Specifications & Targets

We simulate a small biodiesel plant with a total capacity of processing 1 ton of oil per hour after the extraction procedure (see section A2.1 below), hence a total of 7.92 ktons/yr for a plant operating 24 hr/day for 330 days in a year. This results in an annual production of biodiesel of 7.84 ktons. The corresponding feedstock here is rapeseed (19.39 ktons/yr) and the by-products are the crude glycerol (1.29 ktons per year) and rapeseed meal (11.47 ktons per year). The life-time of the plant investment is set to be 20 years. The plant is modelled using Aspen Plus®.

A2.1. Process Description of Biodiesel

The biodiesel process simulated in this study is depicted in FIG. 1. Here, we have used a configuration similar to those suggested by Zhang, Dube, McLean and Kates [1.13]. However, here we have also included an oil extraction process and we have used complex kinetics for the biodiesel transesterification reaction obtained from the literature [1.32].

The first step in our integrated biorefinery is the extraction of oil from crop seeds, which in this case involves rapeseeds containing 43% oil, 9% moisture and 48% solids. The oil content is an average estimation of the different species of winter and spring oilseed rape varieties [1.33]. The oil extraction process is carried out using first a mechanical press that crushes the seeds followed by a solvent extraction process that strips out most of the remaining oil from the rapeseed meal. The obtained oil yield from a mechanical press is 80%, which is increased with the addition of a solvent extraction unit to a final yield of 95%. These values have been provided to us by CETIOM [1.34] and CREOL [1.35]. We have included the above in our model also considering the equipment cost and the utility values. Here we have used €0.9M and €23,300/yr, respectively, which have been adapted for our plant's capacity from values provided to us by [1.34], [1.35] and Desmet Ballestra [1.36] using a scaling law equation as in [1.37]. We assume that the organic solvent used here (e.g. hexane) is separated and recycled completely.

After the oil extraction, the triglycerides enter in the transesterification reactor and react with methanol to produce fatty acid methyl esters (biodiesel) and glycerol, which is the main by-product. We have assumed here that the oil is entirely composed of the triglyceride triolein which is the main component of rapeseed oil. The overall transesterification reaction is:

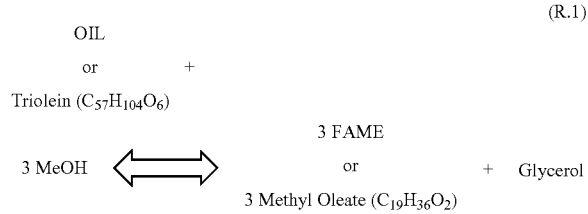

(R.1)

Reaction (R.1) is broken into three steps (R.2, R.3 and R.4) and can yield up to 99% mol-FAME/mol-Triolein. The rate expressions for these reactions were obtained from Komers, Skopal, Stloukal and Machek [1.32] using a potassium hydroxide catalyst and the transesterification unit has been simulated and optimised previously by Binns, Vlysidis and Theodoropoulos [1.20].

  (R.2)

  (R.3)

  (R.4)

As these reactions are reversible we provide a surplus of methanol and an alkaline catalyst, KOH (approximately 1%) to promote the FAME production.

The transesterification reaction is followed by a methanol recovery distillation column that recycles most of the remaining methanol back to the methanol stream for reuse. Methanol concentration in the reactor is a very crucial parameter that has a major effect on the reaction yield. Furthermore, methanol is an expensive chemical that can influence the economics of the entire plant; thus recycling becomes necessary. Here, we obtained the methanol feed rate that enters the reactor and the fraction of the methanol recovered from the optimisation work of Binns, Vlysidis and Theodoropoulos [1.20]. The values were set to 164.14 kg/hr for the MeOH feed rate and 84% for the methanol recovery.

Subsequently, we neutralise the catalyst by adding hydrochloric acid that reacts with the potassium hydroxide and forms potassium chloride and water. The solid KCl is removed afterwards by decantation. Finally, we refine the produced FAME by a water-washing unit that strips out the undesired impurities contained in the biodiesel stream and a subsequent distillation column for a final purity of over 99.9%.

A2.2. Options for Biorefinery Designs

In this study, we have explored three different options for the utilisation of crude glycerol starting from the obvious purification choices and including an advanced co-production design: 1) the distillation of the glycerol waste stream to 80% w/w, typical initial purification level 2) the purification of glycerol to 95% USP glycerol and 3) the bioconversion of glycerol to succinic acid. We consider also the worst-case scenario (scenario 0) which is the disposal of crude glycerol as a waste. In this case, the flow sheet remains the same as in FIG. 1 and the crude glycerol is treated as a non-toxic waste stream from the industry incurring a cost for its disposal. A feasible topology for each option has been implemented based on a typical biodiesel plant [1.13] with additional units, which are able to accomplish both the bioprocessing and/or the separation tasks involved in each of the scenarios 1-3. We then focus the optimisation studies presented here on the bioconversion process (scenario 3) since it represents the novel segment of the overall plant proposed. Obviously different configurations are plausible (e.g. different separation sequences), however the exploration of such design alternatives is outside the scope of this work. Several schemes are analysed in our book chapter [1.20] and a further comprehensive topological analysis will be the subject of a future publication.

A2.2.1. Distillation of glycerol to 80%

A straightforward way to add value to the crude glycerol is by refining it to levels that are attractive to the glycerol markets. Thus, we add a distillation column (FIG. 2) that concentrates the crude glycerol from (63.2% w/w) to (80.0% w/w) removing most of the water and methanol from the top of the column and extracting the crude glycerol from the bottom. This column has 7 stages, the feed enters at the 1st stage, the reflux ratio of the reboiler is 0.68, and the heat duty consumed is 35,890 BTU/hr. The 20% w/w of the resulting glycerol stream consists of impurities such as methanol, water, FAME traces that have not been separated and oil traces that have not reacted during the transesterification process.

A2.2.2. Purification of glycerol to 95%

The second scenario involves the same configuration as the first one (FIG. 2) and we only change the efficiency of the distillation column in order to purify the crude glycerol to 95%. The resulting column is the same as in scenario 1 but with a reflux ratio of 2.59 and heat duty consumed 92,284 BTU/hr. Although, the column's capital cost remains the same there is a difference in the energy consumption as we need more energy to recover the glycerol to such high levels.

A2.2.3. Production of Succinic Acid

Figure 3:
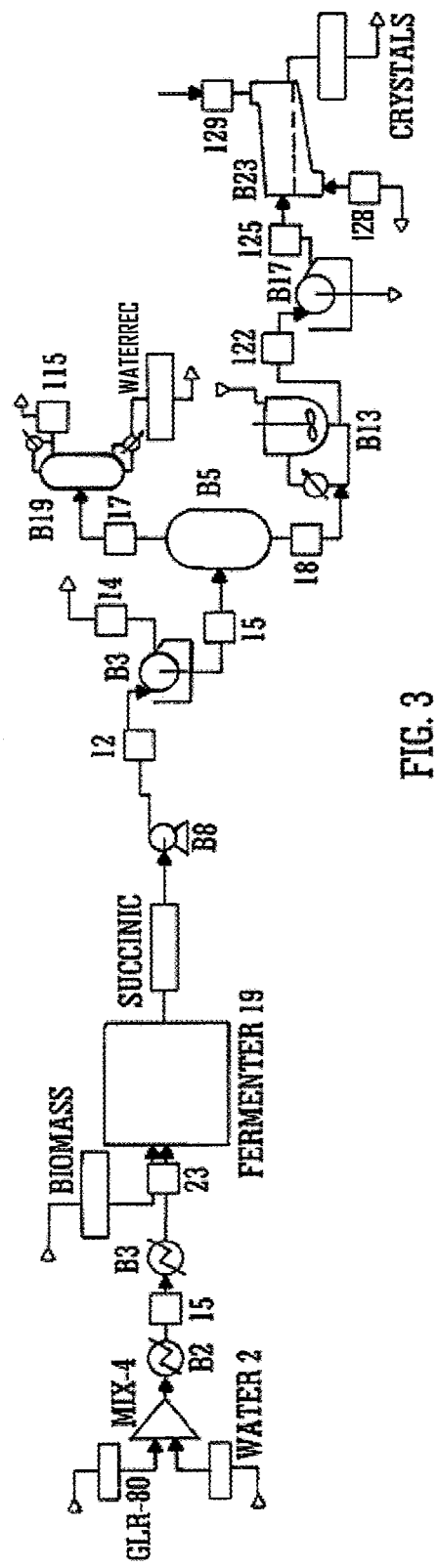

In the third scheme, we have used the crude glycerol stream as a carbon source for producing succinic acid via fermentation. In FIG. 3, the fermentation process that bioconverts the glycerol to succinate followed by a downstream process that purifies the final product to succinic acid crystals is shown. Initially, the glycerol stream is being diluted with water in order to get a glycerol concentration of 3.0-7.0 w/v (%) and then is heat sterilised (121° C.) before it enters into the batch bioreactor. Biomass is also introduced into the reactor through a separate stream. Although the biodiesel production and the downstream process are continuous processes the fermentation step is a batch process. To tackle this problem, we use four bioreactors that are arranged so that succinate is constantly produced, i.e. when two of them operate in parallel, the other two are emptied, cleaned, sterilised and filled with new feed. In this work, we have not considered any other nutrient (e.g. nitrogen or phosphorus source) that participates in the fermentation process apart from glycerol. The remaining methanol in the crude glycerol stream has a concentration of less than 1% w/w and thus, this methanol content is not expected to affect the fermentation process (unpublished results). Succinic acid bio-production from glycerol is an innovative bioprocess that has been examined previously in [1.24]. Where an unstructured kinetic model, taking into consideration substrate and product inhibition and predicting the concentrations of the important metabolic compounds (glycerol, succinate, formate, acetate and biomass) in a wide range of glycerol conditions has been developed. Here we use the kinetic model obtained in [1.24] to simulate the fermentation process in MatLab and in Aspen Plus®.

The fermenter outlet stream contains succinate, water, the remaining glycerol, biomass, by-products (acetate and formate), inert methanol and traces of impurities that we need to separate to get the desired product. Thus, after the fermentation unit a downstream process is added (FIG. 3) to purify the succinate produced to its final succinic acid form. Downstream process is facilitated by the fact that our fermentation model predicts very low byproducts-to-succinate ratios for all the initial glycerol concentrations.

The downstream process firstly contains a 8 m$^2$ drum vacuum filter at 70 kPa that separates the solid biomass from the broth followed by an evaporator that vaporises most of the water and concentrates our product stream. The 2.75 m$^3$ evaporator operates at 101° C. and 1 atm and apart from the water it also removes most of the impurities. Acetate, formate and methanol have lower boiling points than succinate and thus they will vaporise along with most of the water. At the bottom of the evaporator we get a concentrated succinate stream with a very low amount of impurities. Due to the large quantities of water used for the fermentation we recycle the water back to the fermenter instead of disposing it as a waste. Thus, the purpose of the distillation column B19 in FIG. 3 is to remove the methanol to obtain a water purity of 99.63%.

After the evaporator, the product stream (18—FIG. 3) enters into a 2 m$^3$ crystallizer that operates at 4° C. in order to transform the succinate into succinic acid crystals [1.38]. The crystals are then separated by a second 1 m$^2$ drum vacuum filter operating at 0.69 atm before they enter to a 10 m$^2$ dryer operating at 70° C. which removes all of their moisture to form the final product.

It is assumed that both drum vacuum filters remove successfully all the solid particles from the liquid and produce solid streams with specified moisture contents of 20% and 15% respectively. The small amounts of acetic and formic acid impurities that enter the crystallisation unit are considered water-miscible, therefore in comparison with succinic acid they do not crystallise resulting to a pure succinic acid product [1.38]. For improved performance, we should lower the pH of the liquid in the crystalliser to more acidic conditions (pH~2) as the solubility of succinic acid in the specified temperature and pH drops to values equal to 30 g/L [1.38].

A2.3. Economic Analysis

In this study, we have also carried out an economic analysis of the four different schemes. In the following section the costing of entire plants is discussed including both capital and operating costs.

A2.3.1. Capital Costs Estimation

The capital cost for a new plant consists mainly of the Fixed Capital Investment (FCI), the land cost and the working capital cost. The last two terms have not been considered since for roughly similar design options, as the ones considered here, they are expected to be comparable. The FCI includes the equipment purchase cost; which we will refer to as the Bare Module Cost (BMC), and all the required additional costs necessary to build the plant (e.g. installation of the equipment). These additional costs are related to the BMC through certain factors taken from the literature [1.37].

The BMC of each unit was calculated based on correlations found in the literature [1.39] which relate the specifications of each unit (size, pressure, materials) to cost. Moreover, we have used the Chemical Engineering Plant Cost Index (CEPCI) [1.40] to update the equipment cost to 2008 prices. For some pieces of equipment such as the drum vacuum filters and the fermenters, we have used scaling law equations relating the cost to size from similar examples found in the literature [1.37].

A2.3.2 Annual Production Cost

To estimate the annual production cost ($C_{APC}$) we take into account the cost of raw materials ($C_{RM}$), the utility costs ($C_U$), the waste disposal costs ($C_{WD}$) and some extra costs ($C_E$) that are essential to plant operation on an annual basis (eq.1).

$$C_{APC} = C_{RM} + C_{WD} + C_U + C_E \quad (eq.\ 1)$$

The $C_{RM}$ is determined by the specified feed rates of the raw materials per year multiplied by their price. The $C_{WD}$ is calculated from the annual tons of waste produced, multiplied by the penalty the industry needs to pay for every ton it disposes. Here, we have considered that the industry produces only non-toxic wastes.

To calculate $C_U$ the annual energy consumption is used. This includes process steam for heating, process water for cooling and electricity. In a plant there are many units such as heat exchangers and column reboilers that use process steam while certain equipment such as pumps and the seed press unit consume electricity for energy. In this study the coolers and condensers are using only process water to remove heat. The process steam is generated using a gas boiler, which is a cheaper form of energy than electricity. The Heating, cooling and electricity requirements for each unit are calculated from the energy balances inside Aspen Plus and utilities are calculated according to the type and the price of energy for each unit. Here, we have assumed that electricity, process steam and process water have prices of 0.0772 [1.43], 0.0179 [1.42] and 0.0009 €/kWh [1.39], respectively.

Furthermore, we have included some extra costs, which are vital in order to operate the plant. The most important of these are the labour, maintenance and repair of the equipment and the plant overhead costs. The plant requires 8 operators for biodiesel production and 2 extra for the succinic acid and downstream process. The average salary of an operator is 28,000 €/y [1.16]. By summarising all the above cost terms, we have calculated the annual production cost for all four cases.

A2.4 Economic Evaluation & Profitability Criteria

All the above scenarios have been economically evaluated and compared using general profitability criteria [1.39]. The most significant is the Net Present Value (NPV), which gives the profit of the plant for a certain period by considering the time value of money. Other criteria such as return on investment (ROI), discounted payback period (DPBP), payback period (PBP), internal rate of return (IRR) and gross margin are also calculated. To evaluate the profitability of the different schemes we have set the lifetime of the plant to 20 years. We have assumed that the construction of the plant finishes at the end of the first year and it starts to operate at its maximum capacity straight ahead. Working capital and land value are not included as well as any salvage value of the plant at the end of the lifetime. The rate of interest (i) used in this study set to be 7% and no taxes are charged against the plant's profits assuming a tax support system for biofuels.

A2.5 Optimisation Studies

A2.5.1. Single-Objective Optimisation

In complex schemes such as those shown in FIGS. 1 and 3 consisting of numerous different units with many different possible configurations there are numerous operating conditions which can significantly affect the biodiesel production cost and the NPV of the plant. Here we have used the optimal parametric values found in a previous study [1.20] for the basic biodiesel scheme, and we have performed further optimisation studies on the succinic acid production and purification processes to maximise the NPV of the succinic acid scenario.

Initially, we identified the parameters having the biggest effect on the plant's profitability. The most important parameters were found, through sensitivity analysis, to be those related to the fermentation process mainly due to the high capital cost of the fermenter, which is dependent on its volume. The cycle time of each batch ($kk_1$) and the feed rate of the water stream ($kk_2$) that enters the reactor (FIG. 3) can considerably affect its volume and thus the total FCI of the plant as well as the annual revenues of the plant because they also affect the succinate production. Moreover, processing more water can significantly increase the utility costs especially for the heat sterilisation and the purification of succinic acid. The optimisation objective used here was to maximise the NPV [39] with respect to the two operational parameters: the water flow rate and the cycle time.

$$\max NPV(kk_1, kk_2) = -FCI(kk_1, kk_2) + P\left(\frac{((1+i)^{LT}-1)}{(i(1+i)^{LT})}\right)$$

Where: P is the annual net profit (Annual Revenues-$C_{APC}$)
i is the interest rate
LT is the lifetime of the plant
FCI is the fixed capital investment To solve this optimisation problem, we have used simulated annealing, a stochastic optimisation algorithm written in Matlab and directly linked with the Aspen Plus simulator to facilitate the automation of the multiple function evaluations required. This stochastic optimisation technique has been shown to probabilistically be able to avoid (with a proper multiple initialisation policy) possible local minima present due to the non-convexities of the underlying non-linear system and to eventually converge in the neighborhood of the global optimum [1.41]. The lower and upper bounds that we set for the two parameters are [20:120] hours for $kk_1$ and [50:120] kmol/hr of water for $kk_2$.

A2.5.2. Multi-Objective Optimisation

Nowadays, a significant driver exists towards the modification of industrial process to more sustainable routes and hence towards processes of lower environmental impact down to certain levels dictated by legislation. Obviously a trade-off to maintain the profitability of processes at acceptable levels exists. Hence, the aim of this multi-objective optimisation study was to compute a set of NPV maxima for a chosen range of $CO_2$ emissions upper bounds, i.e. obtaining our set of results in the form of the corresponding Pareto curves. Initially, we estimated the environmental impact of the biorefinery. For this purpose, we calculated the $CO_2$ emissions as a result of the energy requirements of the plant. Here we used emission factors for steam produced by a gas boiler (0.201 kg-$CO_2$/kWh [1.42]) and for electricity a much higher value (0.537 kg-$CO_2$/kWh [1.43]). Parametric analysis with respect to the two optimisation parameters kk1 and kk2 indicated that 5.6 ktons of $CO_2$ emissions/yr is a reasonable lower bound for the configurations studied and 8.5 ktons/yr $CO_2$ is a feasible upper bound, respectively.

We then implemented a series of optimisation runs for different $CO_2$ emissions/yr between the lower and upper bounds to compute the optimum NPV at different $CO_2$ emission levels. Furthermore, we have also performed single objective optimisation with the objective to maximise NPV by incorporating in the $C_{APC}$ the environmental impact of the plant through the introduction of a penalty price per ton of $CO_2$ produced. The price is set to be 14 €/ton of $CO_2$ [1.44]. Liquid and solid wastes have been included in the operational costs using a cost of disposal [1.45].

A2.6 Sensitivity Analysis

The economic performance of all the above schemes is very sensitive to the prices of raw materials and products, which usually change with time. Although our estimations of material prices are based on the literature (see table 2 and 3) we also studied how profits are affected by fluctuations in the prices of the most important raw materials and products (rapeseed, biodiesel, succinic acid and crude glycerol), hence sensitivity analysis was performed taking into account such fluctuations.

A3. Results and Discussion

In this section our technical and economic evaluation of scenarios 0-3 is presented and comparisons using profitability criteria and environmental impact factors are obtained.

A3.1. Capital Analysis

Figure 4:
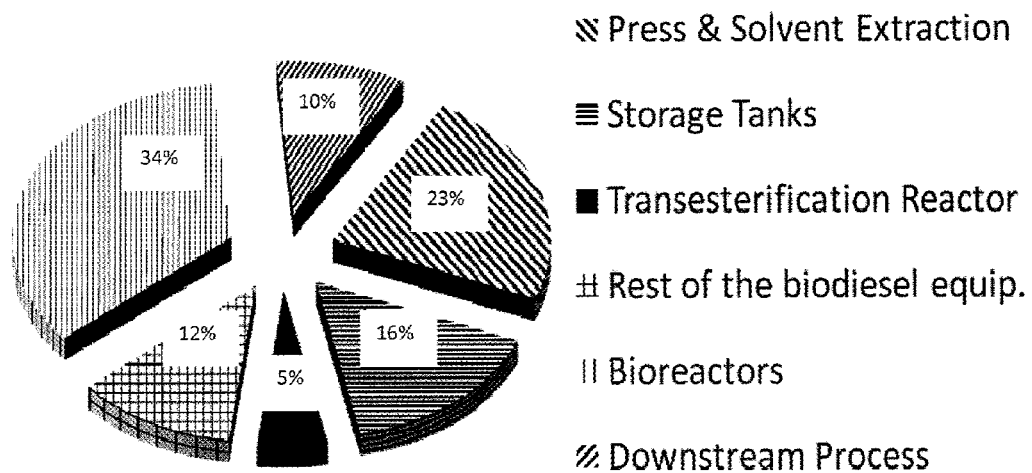

The FCI values and detailed calculations are presented in table 1 for all four scenarios. As expected, there is a significant increase in the FCI for scenario 3 as the BMC is almost double compared to the rest of the schemes. FIG. 4 illustrates the distribution of the BMC for the various parts of the plant for scenario 3. The major capital expense comes from the fermenters and comprises 34% of the total BMC.

The additional 10% BMC for the downstream process results in a significant increase on the overall BMC that has an even greater effect on the FCI as can be seen in table 1.

Also, the storage tank cost which depends on the volume of the vessels is higher for Scenario 3 as we have included an additional tank for the recycled water. The storage capacity of the tanks depends on the input/output flowrates of feedstocks/products and has been designed so as to provide storage for four weeks. For scenarios 0, 1 and 2 storage tank cost is almost 20% less than scenario 3, since no recycled water is used. The remaining 40% of the BMC is the same for all scenarios, apart from scenario 0 where it is slightly less as the glycerol purification column ("Rest of the biodiesel equip." in FIG. 4) has been excluded.

A3.2. Annual Production Cost

In table 2, the annual production costs of the four biorefinery schemes are shown, including all the costs comprising $C_E$. We also present the prices of the raw materials. It is illustrated that most of the production cost (>80%) is based on the cost of rapeseed. This value highlights the main constraint on biorefineries which, contrary to petroleum refineries, is the cost of raw materials. The main difference of scenario 3 from the rest of the schemes is that it requires more energy for the succinic acid production and purification.

Figure 5:
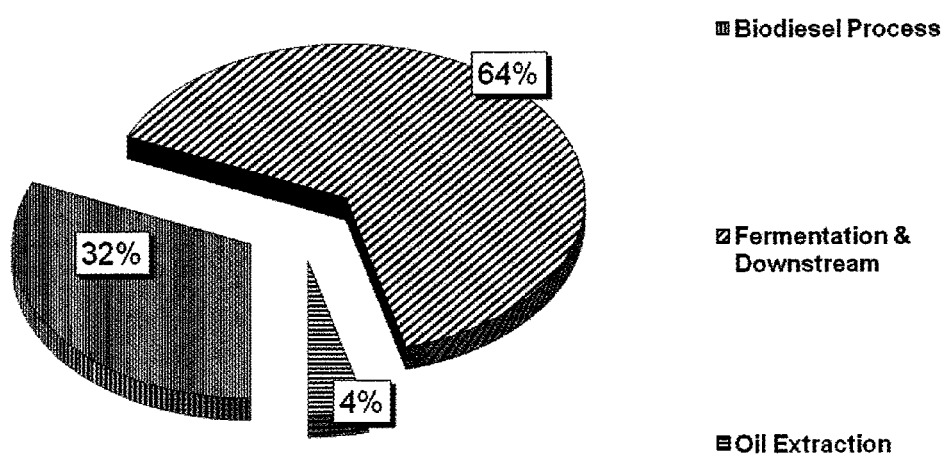

FIG. 5 demonstrates how energy consumption (in kWh) is distributed within the different parts of the biorefinery for scenario 3. The fermentation and the downstream process account for 64% of the total energy consumed which is reflected on the annual utilities cost that is equal to €0.672 M/yr (see table 2). The sterilisation unit (B2 and B3 in FIG. 3) and most of the downstream units (e.g. the evaporator (B5) and the water purification—B19) require a great deal of power to operate at the present broth flowrates. It is concluded that the flowrate of the water entering the bioreactor can have a great effect on the total required energy.

We have also calculated the total production cost per litre of biodiesel produced (Unit Production Cost—see table 2) which is increased for more complex configurations. From table 2 it is shown that this rises from 0.898 €/L (scenario 0) to 1.014 €/L (scenario 3). Although these values are higher from the current selling price of biodiesel (0.799 €/L) and from values published in the literature such as [1.14] and [1.15] they are in good agreement with recent results shown by A. Apostolakou, I. Kookos, C. Marazioti and K. Angelopoulos, [1.16]. The authors in [1.16] have estimated a unit production cost of approximately 0.88 €/L for low capacities (less than 10 ktons of biodiesel per year) which is similar with the value of scenario 0. We can therefore conclude that a low capacity biorefinery plant cannot be profitable without additional revenues from side products.

In Table 3, we present the annual revenues as well as the annual profits for the four scenarios. All scenarios as well as biodiesel they also produce a side product, the rapeseed meal, that is formed from the oil extraction process and can be a very critical revenue for the plant's profitability when no additional revenues exist (scenario 0). Furthermore, there is a noteworthy difference between the annual revenues of scenario 3 and those of the rest of the schemes which is also depicted in the annual profits. Scenario 3 is more profitable than any other case due to the succinic acid production that contributes €1.86 M of extra annual revenues. The corresponding annual succinic acid production is 430.43 tons per year. Moreover, it is shown that scenario 1 has insignificant higher annual profits than scenario 0.

A3.3. Optimisation Results

Figure 6:
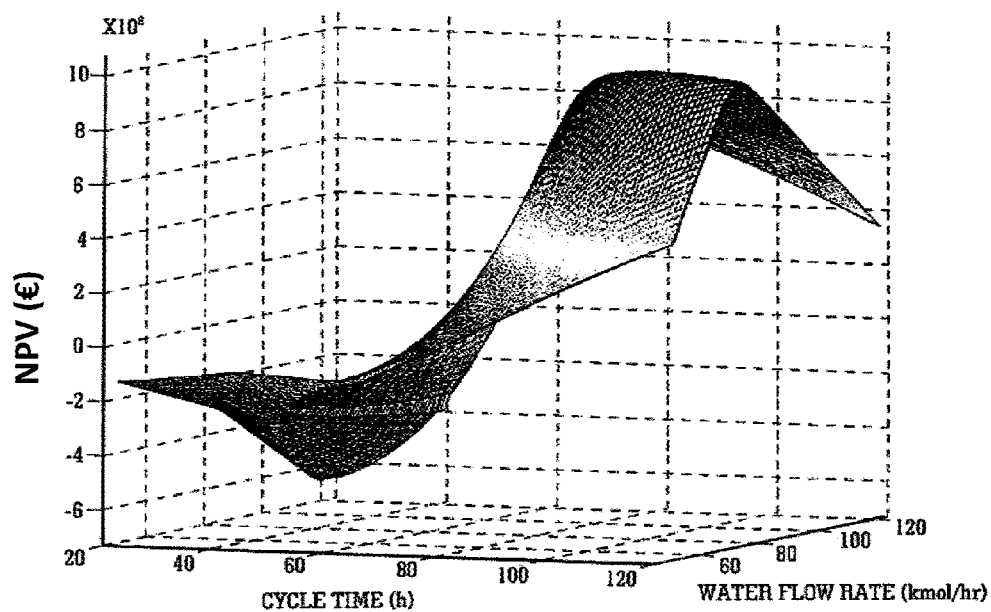

As we mentioned previously, for Scenario 3 we performed single and multi-objective optimisation to simultaneously optimise profits and emissions by changing two critical parameters related to the fermentation process: the cycle time ($kk_1$) and the water flowrate ($kk_2$). In FIG. 6, the results obtained from a two-parameter systematic search are depicted. As it can be seen there is a family of optimal solutions which correspond to high NPV values (around €9 M). It was also found that low cycle times (<60 hours) give a negative NPV value as the bacteria do not have the appropriate time to consume the glycerol and thus lower quantities of succinic acid are produced. On the other hand we can get relatively high NPV values for almost all the range of flowrates (50-120 kmol/hr) for proper cycle times. Very low flowrates (<30 kmol/hr) can decrease significantly the FCI of the plant but also give very concentrated solutions that microbes cannot process fast due to substrate inhibition [1.24] in high glycerol concentrations.

Results from the stochastic optimisation runs with a range of starting points revealed a global optimum solution of 104 hours cycle time and 79.7 kmol/hr water flow rate, which give an optimum NPV of €9.95 M for 20 years lifetime with a 7% rate of interest. It should be mentioned here that these are the $kk_1$ and $kk_2$ values that have been used to compute the results presented in sections 3.1 and 3.2.

A3.4. Profitability Criteria

In order to compare the above four schemes we used several profitability criteria. Among them, the most important considered here are the NPV and the IRR. However, the optimisation studies performed target the maximisation only of the first one.

Figure 7:
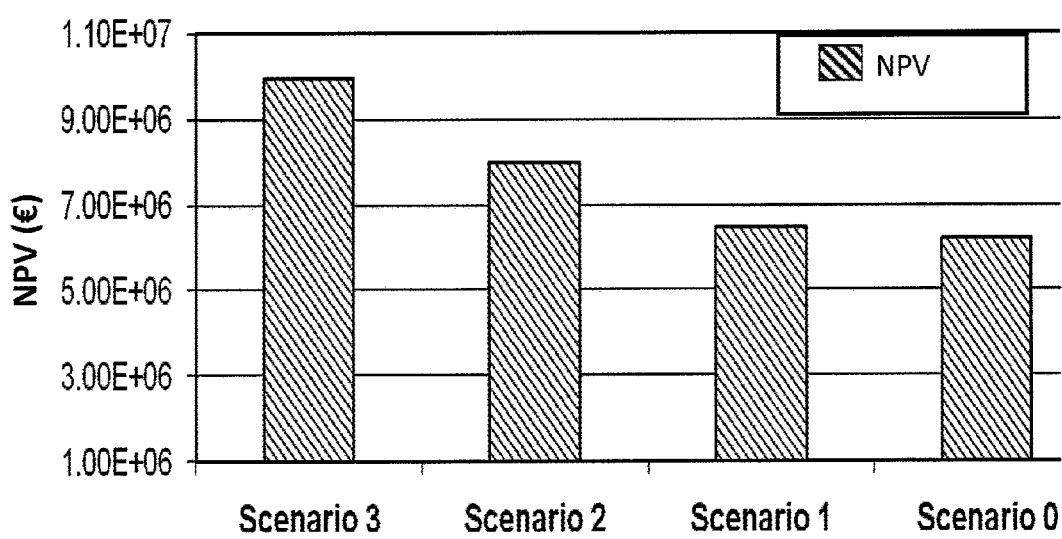

In FIG. 7 and in table 4 we present the NPV of the four scenarios. Scenario 3 is found to be more profitable in the measured lifetime (20 years) and interest (i=7%).

Figure 8:
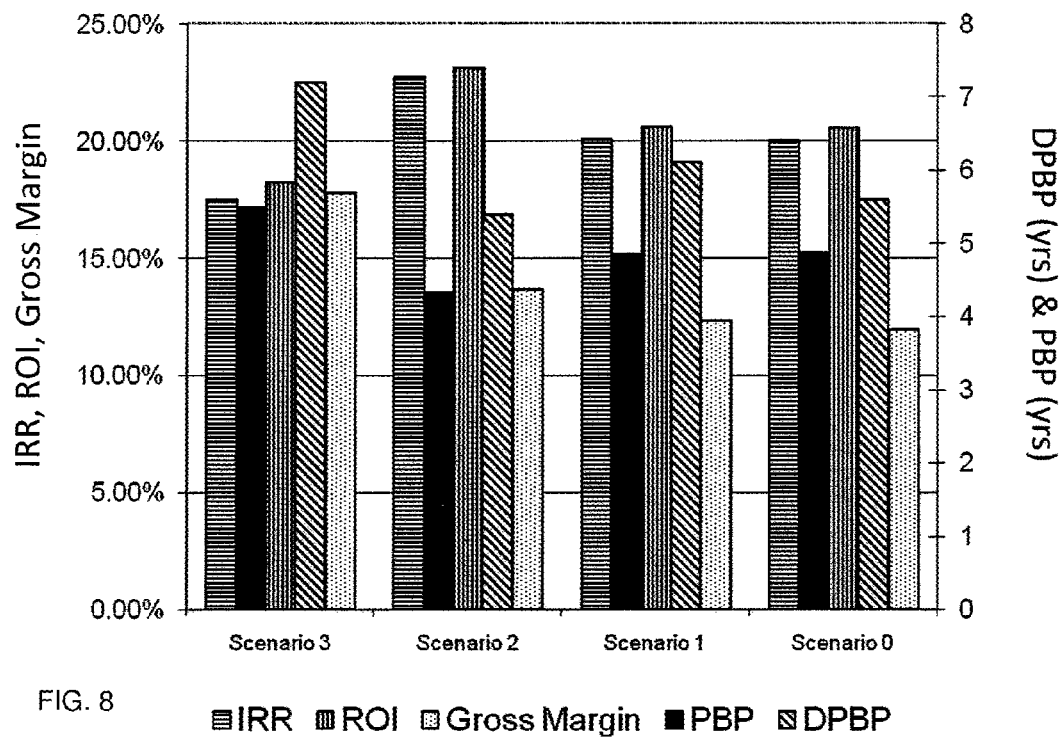
Figure 9:
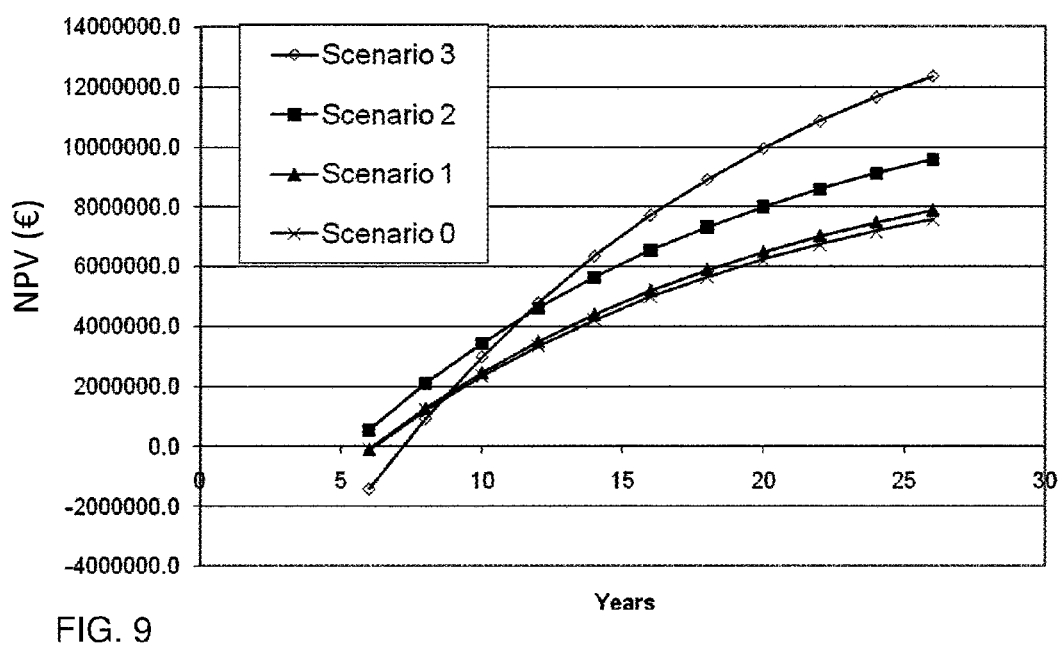
Figure 10:
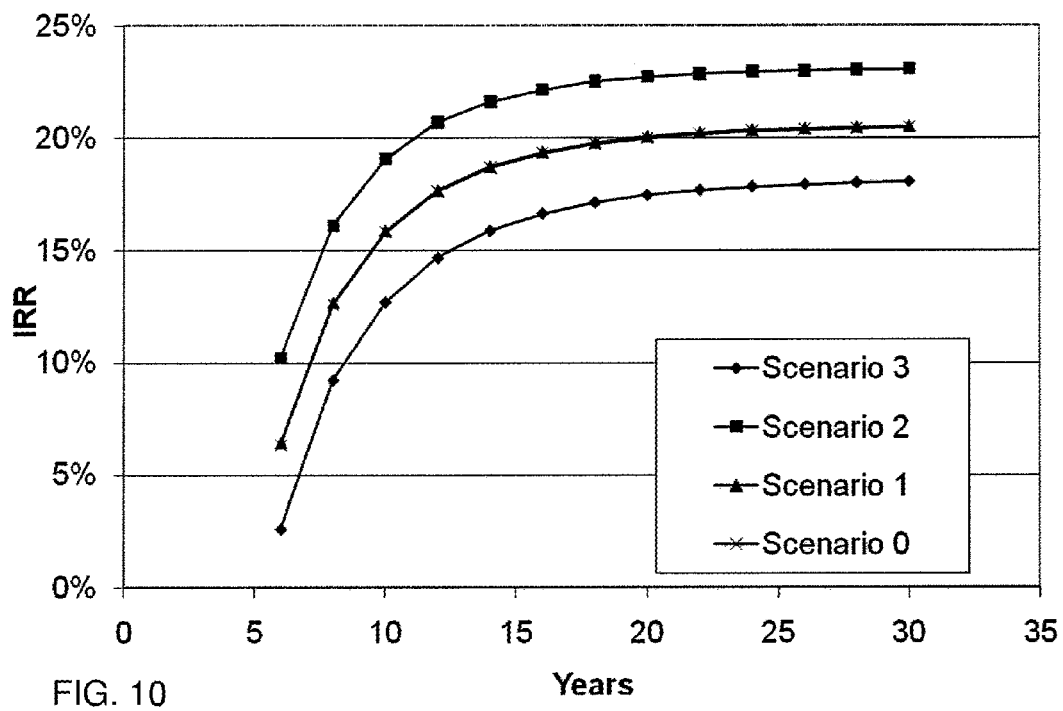

Apart from the NPV, we also calculate the DPBP and the IRR. The first one is the discounted payback period to recover the FCI while the IRR is the interest (or discount rate) for which the NPV is equal to zero. The IRR indicates the efficiency of our investment. The higher the IRR, the more attractive is the project we invest our money in. Moreover, we have calculated several non-discounted (time value of money is not taken into account) profitability criteria. These are the PBP, the ROI and the gross margin. The PBP is the time required to receive back the FCI and the ROI is the percentage of that money we recover annually from the plant's profit (ROI%=Profit/FCI). The gross margin is the ratio of the annual profits divided by the annual revenues. All the above values are shown in table 4 and illustrated in FIG. 8, which show that scenario 3 is less attractive in terms of IRR and ROI than the other scenarios. However, the obtained values, 17.5% and 18.2% respectively, are much higher than our base case interest rate (7%) showing a rather low investment risk. Furthermore, scenario 3 demonstrates a high value of gross margin (17.8%) as it exhibits the highest cash flow in and a high DPBP, which is 1.8 years more than scenario 2. It is noteworthy that its NPV becomes lower than the one of scenario 2 for interest rates greater than 12%. Moreover, it seems that the purification of glycerol—scenario 2 can contribute to some extent to the plant's profit (highest IRR and ROI) without investing much more money, which is similar to the conclusions extracted in [1.17]. FIGS. 9 and 10 show how the NPV and IRR drop for shorter plant lifetimes. Scenario 3 gets the highest NPV from all the other cases (FIG. 9) and an IRR value greater than 15% (FIG. 10) after the end of the 12$^{th}$ year.

A3.5. Sensitivity Analysis

Figure 11:
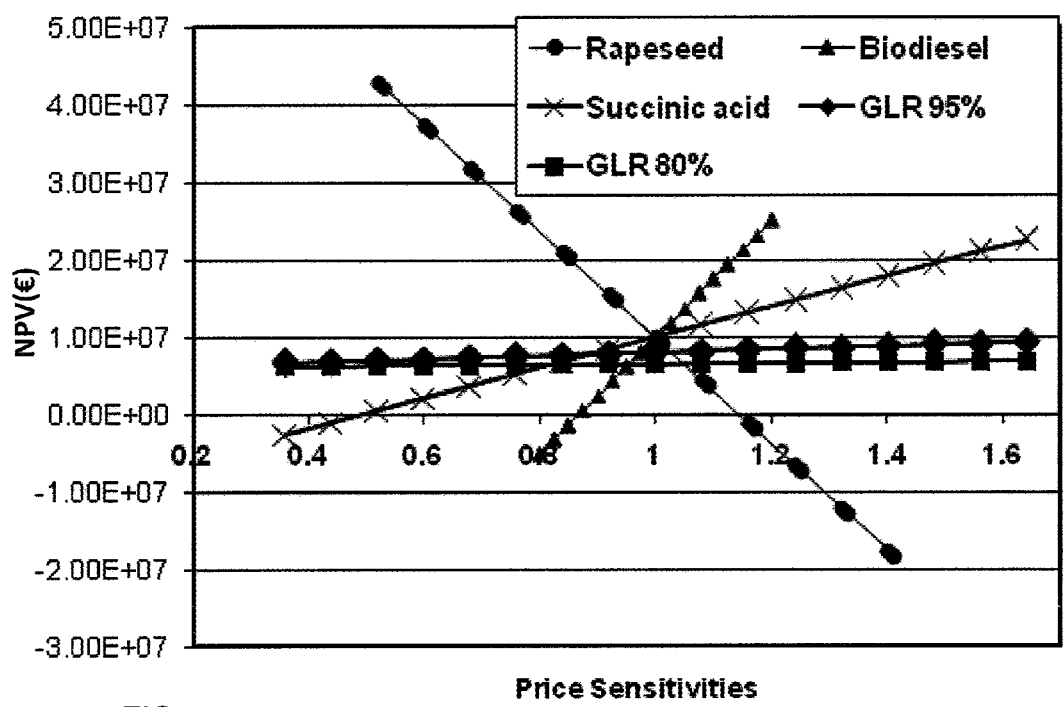

Results from the sensitivity analysis are illustrated in FIG. 11 and table 5, where variations in the prices (sensitivities) of the most important materials are considered. The reference case (prices) we have used for the economic analysis (tables 2 and 3) corresponds to price sensitivity equal to 1. Sensitivities less/more than one correspond to decrease/increase in prices e.g. for sensitivity 1.2 we have a price increase of 20% from the reference value.

As it can be seen in FIG. 11 the effect of price sensitivities on the NPV for the four scenarios is linear. From the slopes of the lines in FIG. 11 it is obvious that the price variations that have the highest effect on the NPV, for all scenarios, are those of biodiesel and rapeseed. In addition, succinic acid price variations have a much greater influence for scenario 3 than the purified glycerol (95%) and the distilled glycerol (80%) have for scenarios 2 and 1, respectively, which is rather negligible. The corresponding values of these slopes are shown in table 5. Note that rapeseed is the only raw material in the list; hence its slope is negative since increase/decrease in its price will lead to decrease/increase in NPV.

A3.6. LCA and Multi-Objective Optimisation Results

The emitted $CO_2$ is related to the type and amount of energy consumed. For the single-objective optimum of scenario 3, it is 7.0 ktons/yr $CO_2$ while for Scenario 2, 1 and 0 is 3.36, 3.33 and 3.29 ktons/yr, respectively. Scenario 3 emits much more $CO_2$ than the rest of the schemes due to the large amounts of energy required for the fermentation and downstream process. We have also included the $CO_2$ that is being consumed during the fermentation by the bacteria as the succinate production works better under carbon dioxide fixation [1.24].

Figure 12:
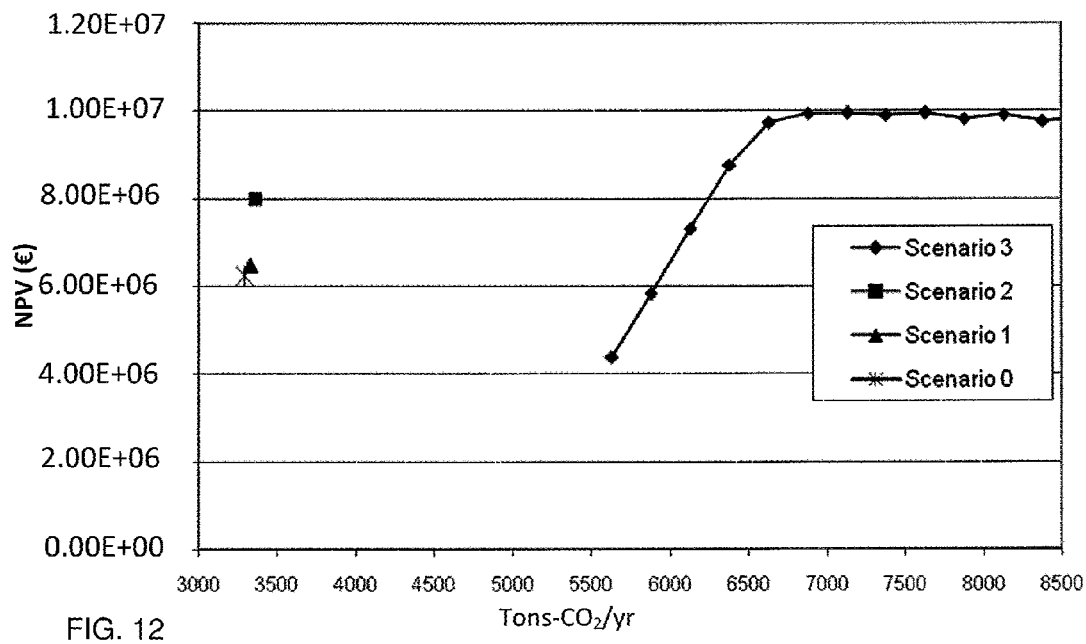

Results from the multi-objective optimisation are presented in the Pareto curve in FIG. 12. It is illustrated that we can lower the $CO_2$ emissions by 5.7% (0.4 ktons-$CO_2$/year) with only sacrificing a small amount (2.2%) of plant's NPV (9.73 M€ instead of 9.95 M€). The new operational parameters are now 120 hours of cycle time and 71.80 kmols/hour of water flowrate. Thus, to lower the $CO_2$ emissions we should process more concentrated solutions (less amount of water) and we should also allow more time to the microbes to bio-convert the glycerol to succinate due to high initial substrate concentrations.

Another way to include environmental impact considerations into the optimum plant design is to incorporate emissions into the objective function e.g. the NPV. To do so, we have included in the annual production cost of the plant a $CO_2$ penalty price equal to 14 €/ton-$CO_2$. Optimisation results with the new objective function yielded a new optimum point corresponding to cycle time and water flowrate equal to 120.0 hours and 73.51 kmol/h, respectively as well as and a new NPV of €8.82 M. For this new optimum point the obtained $CO_2$ emissions are 6.7 ktons-$CO_2$/yr, which is close to the lowest emissions obtained with the multi-objective optimisation.

A4. Conclusions

This is the first time, to the best of our knowledge; an entire biodiesel plant is simulated and designed to produce biofuels (biodiesel) and chemicals (succinic acid). Optimisation studies indicate that sensitive parametric conditions play a vital role on the plant's sustainability. Scenario 3 is the scheme with the greatest positive NPV and the highest gross margin. Although the IRR for this case lower than for the other scenarios it is still much higher than our base interest rate (i=7%) which makes scenario 3 an attractive investment.

Small capacity biodiesel plants (<10 ktons/yr) require additional revenues apart from biodiesel-derived profits, as they cannot economically survive due to the high cost of the raw materials (the seeds and/or the oil). Although, we have used a small-scale plant (7.8 ktons/yr) in this study, we have showed that it is still profitable due to the income from the side-products. Sales of rapeseed meal and succinic acid can give an extra economical boost to plant's profitability. Sensitivity analysis on price variations indicates that the NPV is very sensitive on rapeseed and biodiesel price fluctuations while GLR 95% and GLR 80% price change has a rather insignificant effect. Succinic acid price can play a critical role towards plant's profitability. A 10% decrease in succinic acid price makes it less profitable than scenario 2 while a 60% decrease results in negative profits. Although succinic acid price is currently high, since it is being absorbed by a rather small specialty market, the target is to decrease it to lower levels.

Currently "succinic acid is only a niche product". Its global annual production reaches 30,000 tones a year and its corresponding market worth is around $225M. A significant expansion (up to six times) is expected by 2015 mainly due to the commercialisation of bio-production processes [1.49]. These novel (bio)technologies can be exploited in order to substitute petrochemical alternatives such as maleic anhydride with succinic acid and to create a succinate market that consists of commodity chemicals. To do that succinic acid price should decrease below 2.5 €/kg. Finally, we have shown how environmental impact can be reduced by exploiting multi-objective optimisation methods. We have demonstrated that the annual $CO_2$ emissions can be decreased by 5.7% without significantly affecting profit. The same methodology can be implemented to similar environmental studies for decreasing other important pollutants.

Current results can be further improved by a number of ways. Larger capacity plants should be able to cope with a considerable price decrease as they will exhibit higher NPV and IRR values [1.16]. Furthermore, improving the operating performance of the bioreactors by using fed-batch or continuous configurations can significantly improve the succinic acid productivity and thus the profitability of the overall biodiesel plants. Apart from the process modifications, alteration and/or manipulation of bacterial performance can enhance industrial applications on bio-processing. Better biocatalysts can be created, by applying genetic engineering methods, which can consume faster higher concentrations of crude glycerol. These microbes will then require less diluted substrate concentrations resulting in smaller quantities of processing water and hence smaller bioreactors. We believe that the combination of overall plant simulation and economic/environmental analysis in conjunction with process innovations can lead to efficient integrated biorefineries capable of producing a range of sustainable fuels and chemicals.

B Experimental Results

The invention will now be further described with reference to the following examples, models, figures and tables.

The methods of the invention provide an effective method for the valorisation of the main by-product of biodiesel production, i.e. glycerol is proposed in this work. It involves the biological conversion of glycerol to succinic acid, a top added-value material, which can be used as a building block for the production of various commodity and specialty chemicals. Our aim is to give new insights into this bioprocess, which has so far received little attention and is open for further investigation, through a combination of experimental and computational studies. High yields with high final succinate concentrations were produced in batch bioreactors using *Actinobacillus succinogenes* as the microorganism and glycerol as the only carbon source. Furthermore, an unstructured model of the batch experiments was developed by considering both substrate and product inhibition. Kinetic parameters of the model were estimated by minimising the difference between experimental and predicted values. The corresponding optimisation problem was solved by using a combination of stochastic and deterministic methodologies, with the goal to probabilistically compute global minima and the resulting parameter values. The model developed can be utilised to successfully predict the concentration profiles of the five most important state variables (biomass—glycerol—succinic acid—formic acid—acetic acid) with different initial glycerol concentrations. Scaled-up experiments in larger-scale bioreactors were used for further validation purposes. Our model can be further used to compute optimal operating/parametric conditions, which maximise yield, productivity and/or the final succinic acid concentration.

Nomenclature

| | | |
|---|---|---|
| $K_S$ | g/l | Substrate saturation constant |
| $K_I$ | g/l | Substrate inhibition constant |
| $n_{SA}$ | — | Linearity of the SA inhibition |
| $Y_X$ | g-X/g-S | Stoichiometric Yield of Cells to Glycerol |
| $Y_{SA}$ | g-$P_{SA}$/g-S | Stoichiometric Yield of SA to Glycerol |
| $m_s$ | g-S/g-X h | Specific maintenance coefficient |
| $P_{SA}^*$ | g-$P_{SA}$/L | Critical succinic acid concentration |
| X | g-DCW/L | Biomass concentration |
| S | g-GLR/L | Substrate concentration (glycerol) |
| $P_i$ | g-$P_i$/L | Product concentration ($P_{SA}$, $P_{FA}$, $P_{AA}$) |
| $q_s$ | g-GLR/g-DCW h | Specific uptake rate |
| $q_p$ | g-$P_i$/g-DCW h | Specific production rate |
| | | Greek letters |
| μ | $h^{-1}$ | Specific growth rate |
| $μ_{max}$ | $h^{-1}$ | Maximum specific growth rate |
| $a_{SA}$ | g-$P_{SA}$/g-X | Growth association constant for SA |
| $β_{SA}$ | g-$P_{SA}$/g-X h | Non-growth association growth for SA |
| $a_{FA}$ | g-$P_{FA}$/g-X | Growth association constant for FA |
| $β_{FA}$ | g-$P_{FA}$/g-X h | Non-growth association growth for FA |
| $a_{AA}$ | g-$P_{AA}$/g-X | Growth association constant for AA |
| $β_{AA}$ | g-$P_{AA}$/g-X h | Non-growth association growth for AA |

List of Abbreviations

USP Glycerol Pure Glycerol according to the specifications of United States Pharmacopeia
PHB Polyhydroxybutyrate, a polymer belonging to polyesters class
US DOE United States Department of Energy
SARs Small Anaerobic Reactors
ATCC American Type Culture Collection
Vvm Volume gas/volume liquid/minute
UV Ultra Violet
RI Refractive Index
$OD_{660}$ Optical density at 660 nm
GLR Glycerol
DCW Dry Cell Weight
TSB Trypticase Soy Broth
ODEs Ordinary Differential Equations
SQP Successive Quadratic Programming (deterministic optimisation method)
SA Succinic acid
FA Formic acid
AA Acetic acid
PEP Phosphoenolpyruvate (Branch intermediate in the glycerol metabolism to succinate)
HPLC High Performance (Pressure) Liquid Chromatography
Abs Absorbance B1. Introduction Methods and microorganisms in accordance with the present invention were investigated using the following materials and methods. The results of these investigations, and conclusions that can be drawn from these results, are considered herein.

B2. Materials and Methods 2.1) Inoculum Preparation

*Actinobacillus succinogenes* (ATCC 55618) was obtained from the American type culture collection (ATCC, Manassasa, Va., USA). Initially, the cells grown in a glycerol-rich environment were preserved in cryopreservation vials (15% v/v glycerol solution) at −30° C. Preculture of the strain was performed in an incubation room at 30° C. using 100 ml Duran bottles containing 50 ml of trypticase soy broth (TSB), 30 g/L which were placed on a rotary shaker at 200 rpm for 1-2 days. The medium was heat sterilized at 121° C. for 20 min. Inoculation started by adding the content of a preservation vial to the TSB medium.

2.2) Study in Small Anaerobic Reactors

Experiments were carried out in SARs with working volumes of 70 ml each. A modified semi-defined medium [2.26] was used with glycerol as the only carbon source. This semi-defined medium contained per litre: glycerol, 0-120 g; yeast extract, 5-10 g; $NaH_2PO_4.H_2O$, 1.16 g; $Na_2HPO_4$, 0.31 g; NaCl, 1.0 g; $MgCl_2.6H_2O$, 0.2 g; $CaCl_2.2H_2O$, 0.2 g; B12, 1 μg; biotin, 20 μg; folic acid, 20 μg; thiamine, 50 μg; riboflavin, 50 μg; niacin, 50 μg; pantothenate, 50 μg; p-aminobenzoate, 50 μg; lipoic acid, 50 μg; B6, 100 μg; $MgCO_3$, 10-30 g; silicone antifoam 0.3 g (Struktol, J647). A series of experiments were conducted using different initial substrate concentrations ranging from 0 to 120 g/L. The Duran bottles were sealed with butyl rubber stoppers and were autoclaved at 121° C. for 20 minutes. The glycerol solution was autoclaved separately and was added aseptically to the medium right after sterilisation. The SARs with the mixed medium were placed on a rotary shaker at 120 rpm and incubation took place at 37° C. The inoculum was 10% (v/v) and during the experiment, $CO_2$ gas (BOC-gases) was sparged into the fermentation broth. Samples were taken every 6-8 hours and fermentation was stopped when cell growth was in the late decline period where no further glycerol consumption was detected.

2.3) Study in a Bench-Top Reactor

Batch fermentations were also carried out in a 1.8-L bench-top bioreactor (Electrolab 351, Tewkesbury, UK) with a working volume of 0.7 L. The medium composition was similar to the ones used in SARs. The only difference is that the pH was controlled at a lower level of 6.4 by adding 10M of NaOH solution when that was necessary. The inoculum size was 10% (v/v) and the fermentation broth was sparged with 0.2 vvm $CO_2$ and agitated at 200 rpm. All chemicals used throughout this study were obtained from Sigma-Aldrich, UK or Fisher Scientific, UK, unless stated otherwise.

2.4) Analytical Methods

Cell growth, indicative of glycerol metabolism, was determined by measuring the absorbance at 660 nm ($OD_{660}$) using a spectrophotometer (UVmini 1240, Shimadzu, Europa, Germany). Sample dilution took place by adding 7% (v/v) hydrochloric acid (HCl) instead of water in order to remove the undissolved $MgCO_3$. The linear relationship between $OD_{660}$ and dry cell weight (DCW) per litre was found previously [2.35] to be g-DCW/L=Abs·0.626.

Glycerol substrate and fermentation end-products such as succinic acid, acetic acid, formic acid, pyruvic acid, propionic acid and fumaric acid were also measured directly using a High Performance Liquid Chromatographer (HPLC—Star Varian Chromatography Workstation) with a UV (Prostar 330 PDA) and an RI detector (ERC-7515A) in series and a Hi-Plex H 8 μm 300×7.7 mm (Polymer Laboratories) column.

2.5) Model Studies

A modified Monod kinetic expression was used to describe the growth kinetics considering both substrate and product inhibition. From preliminary experiments, it became clear that high substrate concentrations significantly reduce the specific growth rate. Therefore, since glycerol seems to act as an inhibitor in elevated concentrations, the Haldane equation [2.27, 2.28] (Eq.3) was preferred for explaining the cell behaviour instead of the simple Monod equation.

$$\mu = \mu_{max} \cdot \left( \frac{S}{S + K_S + (S^2/K_I)} \right) \quad (3)$$

Here: μ is the specific growth rate ($h^{-1}$), $\mu_{max}$ is the maximum specific growth rate ($h^{-1}$), $K_S$ is the substrate saturation constant (g-GLR/L), $K_I$ is the substrate inhibition constant (g-GLR/L) and S is the limiting substrate concentration (g-GLR/L) which in this case is glycerol.

In addition to substrate inhibition, accumulation of products during the fermentation such as weak acids and their undissociated level can act as inhibition factors and decrease the cell growth considerably [2.29, 2.30]. Thus, an additional term, PI, that considers product inhibition was also introduced as shown in Eq.2 [2.29].

$$PI = \prod_{i=1}^{m} \left(1 - \frac{P_i}{P_i^*}\right)^{n_i}, \quad (4)$$
$$i = 1, \ldots, m$$

Where: $P_i^*$ is the critical product concentration above which cells do not grow (g-$P_i$/L), $P_i$ is the product concentration (g-$P_i$/L), and m specifies the number of products. For this system three end-products are considered: succinic acid which is the main product and formic and acetic acid that are the by-products. The exponents $n_i$ (dimensionless) are the inhibition powers that indicate the relationship between the observed specific growth rate and the product concentrations.

By combining Eq.1 and Eq.2, a final extended Monod model expression is shown (Eq.5) taking into account both substrate and product inhibition.

$$\mu = \mu_{max} \cdot \left(\frac{S}{S + K_S + (S^2/K_I)}\right) \prod_{i=1}^{m} \left(1 - \frac{P_i}{P_i^*}\right)^{n_i}, \quad (5)$$
$$i = 1, \ldots, m$$

Bacterial growth is usually [2.29] described by Eq.6.

$$\frac{dX}{dt} = \mu \cdot X \quad (6)$$

Where: X is the dry cell weight concentration (g-DCW/L).

The product formation rates ($dP_i/dt$) can be described by the Luedking-Piret model [2.31] (Eq.7) where both growth ($\alpha_i$) (g-$P_i$/g-X) and non-growth associated ($\beta_i$) (g-$P_i$/g-X h) terms were considered for all three end-products.

$$\frac{dP_i}{dt} = \alpha_i \frac{dX}{dt} + \beta_i X, \quad (7)$$
$$i = 1, \ldots, m$$

Finally, the substrate consumption rate (dS/dt) can be calculated by a simple overall carbon-mass balance as given in Eq.8 [2.32] which considers glycerol consumption for cell growth, cell maintenance, and products formation.

$$\frac{dS}{dt} = -\frac{1}{Y_X}\frac{dX}{dt} - m_s X - \sum_{i=1}^{m} \frac{1}{Y_{P_i}} \frac{dP_i}{dt} \quad (8)$$

Here: $Y_x$ is the stoichiometric yield of biomass (g-X/g-GLR), $m_S$ is the maintenance coefficient (g-GLR/g-X h), $Y_{P_i}$ are the stoichiometric yields of the products (g-$P_i$/g-GLR) while m is the number of products.

2.6) Parameter Estimation

The above mathematical model describes the dynamic behaviour of this system as a system of ODEs which have the following form (Eq.9):

$$\frac{dZ(t)}{dt} = f(Z(t), kk) \quad (9)$$

where Z is a vector containing the state variables and kk is a vector containing the independent variables (parameters) to be determined.

For this system, there are five state variables.

$$Z = \{X, S, P_{SA}, P_{FA}, P_{AA}\}^T \quad (10)$$

There are also 20 parameters.

$$kk = \{\mu_{max}, K_S, K_I, P^*_i, n_i, \alpha_i, \beta_i, Y_X, m_S, Y_{P_i}\}^T \quad (11)$$

For parameter estimation, a non-linear weighted least square method was used involving the minimisation of an objective function including the sum of squared errors (differences) between the predicted and experimental values of the five state variables (Eq.12).

$$\min G(kk) = \sqrt{\sum_{h=1}^{nh} \sum_{i=1}^{ni} \sum_{k=1}^{nk} \left(w_{hik}\left(Z_{hik}^{pred} - Z_{hik}^{exp}\right)\right)^2} \quad (12)$$

subject to Eq. 4-6

Where: nh: number of experiments ni: number of variables nk: number of points in time kk: the vector of parameters $w_{hik}$: the weights for each variable used to indicate their significance and are equal to $$\left(w_{hik} = \frac{1}{Z_{hik}^{exp}}\right)$$

The corresponding optimisation problem was solved by first using simulated annealing, a stochastic optimisation algorithm implemented in MatLab®, which can avoid local minima and probabilistically compute a family of solutions around the global minimum [2.33, 2.34]. Deterministic optimisation was subsequently implemented using the Successive Quadratic Programming (SQP) method to calculate precisely the final optimum and the corresponding parameter values. The dynamic constraints (Eq 4-6) were computed by using the MatLab® routine ode23. In order to avoid potential unrealistic optima all parameters were constrained within limits found either from experiments or from the literature for similar systems. The initial values of the ODEs were calculated according to the initial conditions of each experiment.

2.7) Values and Bounds of the Independent Parameters

The final number of parameters was reduced from 20 to 14 (see table 10) as the by-products, acetic and formic acid, were not considered to affect either the specific growth rate (eq.5) or the substrate mass balance (eq.8). This is, mainly, due to two reasons: (1) the very low by-products formation with respect to the succinic acid and (2) the discharge of this phenomenological unstructured model and its simplification to a simpler form.

From the 14 remaining parameters, only $P^*_j$ was kept constant as it has been determined previously [2.35]. The 13 model parameters were computed from the optimisation method described above (section 2.6). This is, in our knowledge, the first time where such a model has been developed for the glycerol-succinic acid system including prediction of by-product concentrations. Information about the kinetic parameter values from other studies, for comparison, is very sparse and elusive.

In the next section experimental results in both SARs and bench top reactors, computed parameter values and model validation results are discussed.

B3) Results and Discussion 3.1) Experimental Results

The bioconversion of glycerol to succinic acid is a relatively new route, which has not been thoroughly investigated. This conversion route targets the valorisation of glycerol to enhance the sustainability of biodiesel. As more (bio)-conversion routes of this crude material are explored, the biodiesel industry will become more flexible by adjusting its processing in response to supply and demand.

Figure 17:
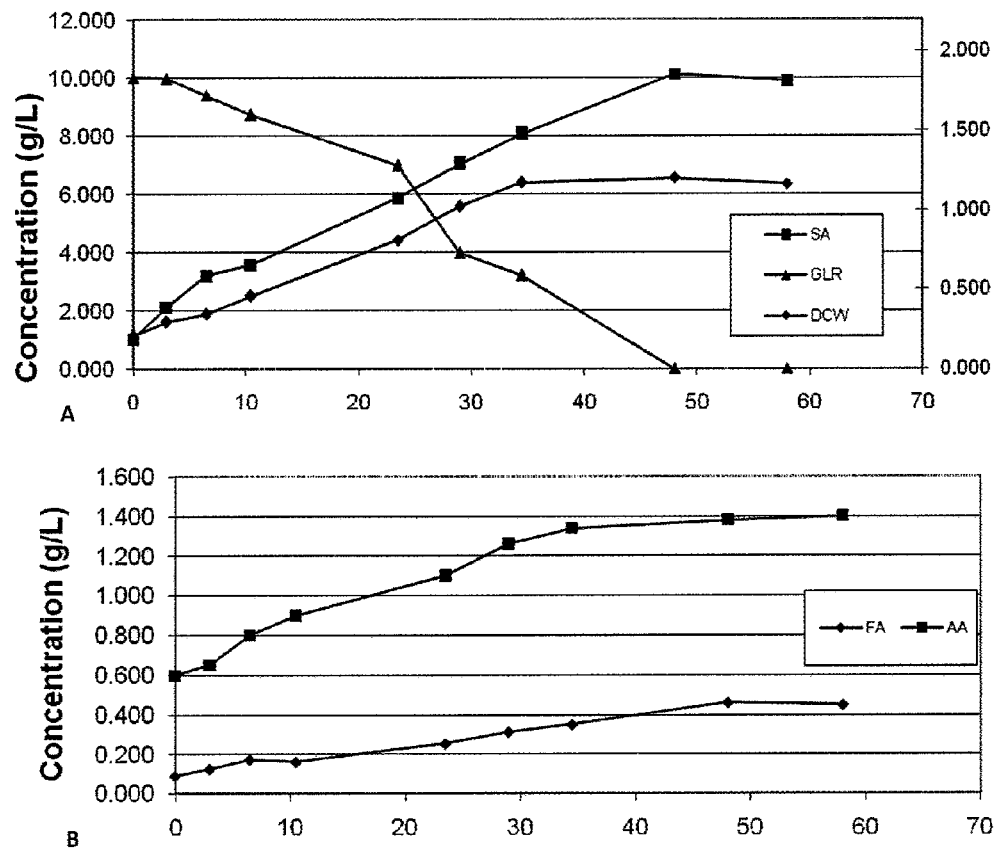
Figure 18:
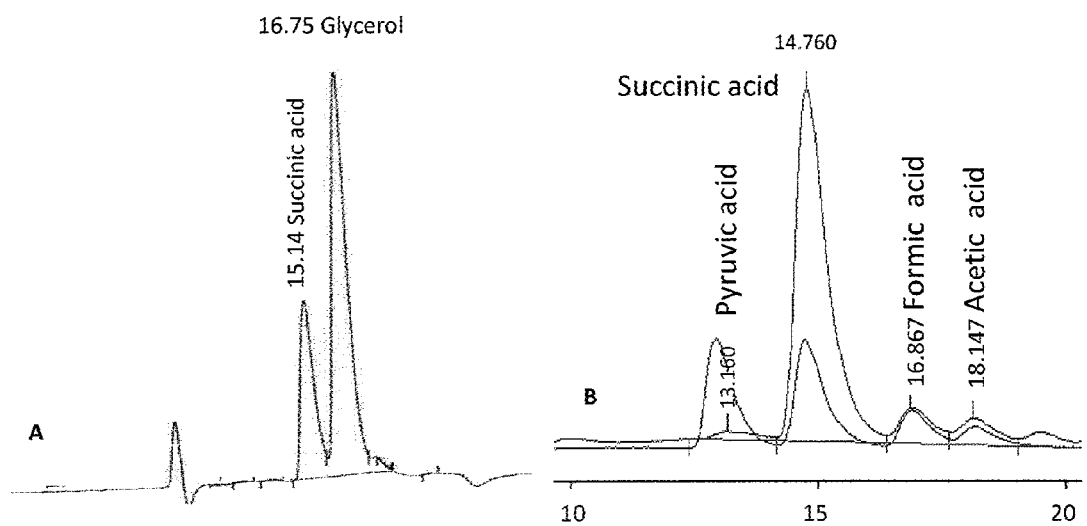

In FIG. 17, a typical fermentation profile is illustrated. The main product formed is succinic acid (FIG. 17A) while the two major by-products are acetic and formic acid (FIG. 17B) which are produced in lower quantities. Yields, productivities and by-products to succinate ratios for different initial substrate concentrations are shown in table 7. One of the strong advantages of this process is that it results in yields that stay at high levels (>0.78 g-SA/g-GLR) for any initial glycerol concentration. This is connected to the high reduced state of this substrate [2.16]. Higher yields were found at low initial glycerol concentrations (3.7, 5.1, 10.0 and 15.0) with a maximum value of 1.12 g-SA/g-GLR. Productivity increases as the initial glycerol increases and exhibits maximum levels (>0.20 g-SA/L/h) in the range of (21-37 g-GLR$_0$/L). The maximum final concentration of succinic acid obtained was 28.3 g/L by using 36.4 g/L of glycerol. We should also point out that this is the first time such high final succinic acid concentrations have been found for this system (see table 8). However, at higher glycerol concentrations (>50 g/L), the substrate is not completely consumed and productivity decreases. An explanation for this behaviour is that the substrate acts as an inhibitor to cell growth. Excessive quantities of substrate in addition to considerable amounts of acids produced during the fermentation as end-products can prevent cells to grow. Nonetheless, yields are kept in the same high levels even at high substrate concentrations.

3.1.1) Comparison of Glycerol-SA Experimental Results with Those of Similar Systems Previous studies investigating the same system have shown poor performance with low productivities and/or low final succinic acid concentrations [2.15, 2.25]. Table 8 shows a comparison of the so far achieved experimental findings from different studies for the glycerol-succinic acid system. The main step forward in this study compared with previous studies [2.15, 2.25] is that here a different microorganism has been exploited (Actinobacillus succinogenes which is an excellent succinic acid producer that can show great tolerance to elevated succinic acid concentrations (>100 g/l) [2.21, 2.26]) and the glycerol-converting activity of this microorganism has been enhanced by training using the methods of the invention. Furthermore, different environmental conditions have been employed (the main one being the addition of high amounts of MgCO$_3$ [2.23, 2.38])

As shown in table 8, product yields are high in all three experiments shown and this is mainly due to the high reduced state of the substrate. The maximum theoretical yield of glycerol to succinic acid (neither biomass nor by-products formation) should be 1.28 g-SA/g-GLR as 1 mol of glycerol reacts with 1 mol of CO$_2$ and produces 1 mol of succinic acid and 1 mol of water as shown in scheme 3.

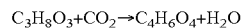

$$C_3H_8O_3 + CO_2 \rightarrow C_4H_6O_4 + H_2O \qquad \text{Scheme 3}$$

Figure 19:
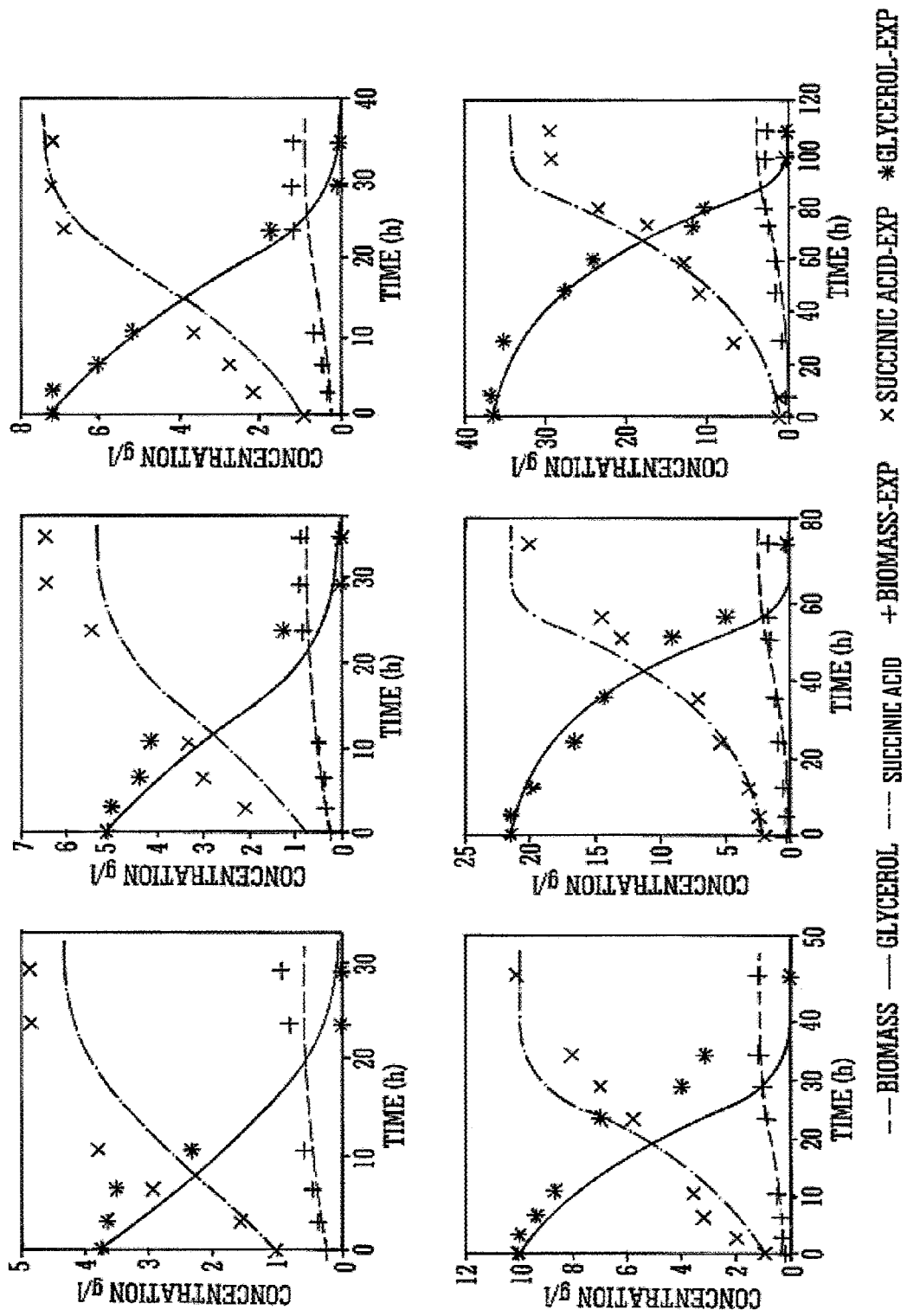

Preliminary experiments clearly indicated that glycerol is not a desirable substrate for bacterial growth compared to glucose or other sugars. The prolonged lag phase in addition to the low cell growth and uptake rates demonstrated in the fermentation profiles of A. succinogenes confirm this assertion. Further evidence is provided by Guettler et al. [2.21] who have tested that glycerol is a poor substrate for this bacterium. Thus, to improve the bio-process a series of experiments were performed for the bio-training (adaptation) of the cells to a glycerol-rich medium. The best cells from each experiment were kept and used for the next batch in gradually increased substrate concentrations. Cells from the last (adaptation) experiment with adequate performance were stored for use in the fermentation experiments. Also, a larger inoculum concentration (10% v/v) was preferred for reducing the lag phase. Furthermore, an organic nitrogen source in the form of yeast extract was used instead of inorganic sources. Yeast extract is a very common complex organic nitrogen source which provides nitrogen in the form of amino acids and can help microorganisms to grow faster. However, we also observed that when yeast extract was used in the absence of glycerol no succinic acid was detected. High Performance Liquid Chromatograms for the UV and the RI detector are shown in FIG. 19 for a typical fermentation sample at the end of batch process. In some of the experiments, small amounts of pyruvic acid were produced as a third by-product during the exponential phase and were mainly consumed by the cells in the stationary phase.

Moreover, in some experiments at the very end of the decline period small amounts of fumaric acid were detected by the UV detector. Finally, no ethanol or lactic acid formation was detected in any of our samples.

Table 9 presents a comparison of experimental results up-to-date for the most important bioconversion routes of glycerol to biomaterials. As we can see, the succinic acid produced in this work has resulted in high yields, higher than the reported yields for 1,3-Propanediol and ethanol, which underpins the great potential of the succinic acid route compared to other biological conversion routes for glycerol valorisation. Nevertheless the reported productivity for SA (0.26 g/L/h) as well as its final concentration (28.3 g/L) suggest there is room for improvement, both from a process and from a biochemistry point of view.

3.1.2) Experimental Conditions that Affect the Bioprocess (pH-$CO_2$—$MgCO_3$)

The most important environmental conditions for our batch process seem to be the $CO_2$ availability [2.36, 2.37, 2.40], the pH levels [2.37, 2.38] as well as the concentration of $MgCO_3$ inside the broth [2.23, 2.26, 2.38]. The pH plays a significant role for all bioprocesses and each microorganism has its optimum pH level. Most bacteria work better at pH around 7.0. A. succinogenes is a bacterium that does not necessitate severe pH control as it can tolerate small pH changes [2.26, 2.38]. The best pH range for this bacterium is 6.2-7.4 [2.26]. Moreover, pH affects the solubility of important gases like $CO_2$.

During the fermentation, the pH of the medium decreases due to the formation of weak acids like succinic, formic and acetic acid. In order to neutralise the acids and to maintain the pH at values which allow optimal cell growth, $MgCO_3$ is added. In addition to preserving the pH at the right growth levels $MgCO_3$ also complements the mineral sources by generating $Mg^{2+}$ and $CO_3^{2-}$ when it reacts with the organic acids [2.23, 2.26]. Succinic acid production seems to be related to the $MgCO_3$ availability and can be increased by adding more amounts of $MgCO_3$ as it helps its dissociation and maintains the pH to viable levels for cell growth. However, excessive addition of $MgCO_3$ (>50 g/L) was found to have a negative effect on cell growth.

Another important environmental parameter is the $CO_2$ supply to the broth which can be provided directly by adding $CO_2$ gas or indirectly through the addition of $MgCO_3$. The succinic acid production requires $CO_2$ supply to be fixed as the main branch intermediate (PEP) of the metabolic network reacts with it and drives the carbon flow to the reductive C4 pathway instead of the C3 pathway [2.36, 2.40]. Therefore, gaseous $CO_2$ should be supplied and diluted in the fermentation broth during the methods of the invention.

Before the inoculation, and after autoclaving, the pH in the fermentation mixture is higher than 8 (due to the presence of $MgCO_3$). By supplying, gaseous $CO_2$ the pH drops from around 8.4 to 7.2 e.g. to levels that the cells can grow. Within this pH level, fermentation starts.

3.2) Modelling of the Batch Processes

To aid experimental design, an unstructured model of the batch experiments was developed which can predict the concentration profiles of the main compounds. To compute the appropriate values for the model parameters discussed in section 2.5, so that experimental results could be effectively predicted, we used the procedure described in sections 2.6 and 2.7.

Figure 20:
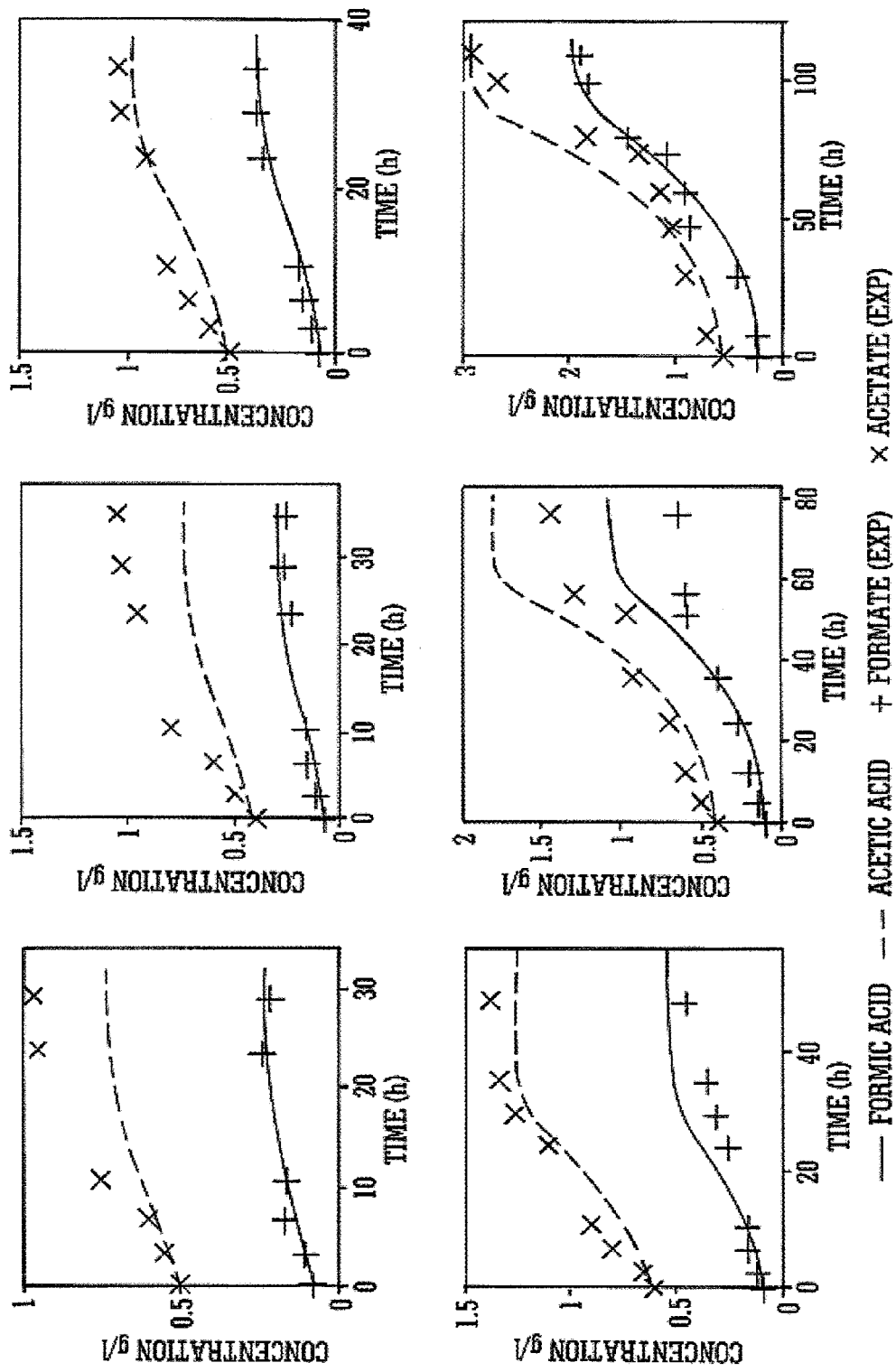

FIGS. 19 and 20 depict the experimental and simulation results for SARs with different initial substrate concentrations (3.7, 5.1, 7.2, 10.0, 21.5, 36.4 g-$GLR_0$/L). Our model takes into account substrate and product inhibition and can adequately predict the experimental data on a wide range of initial conditions. As we can see, it can successfully predict the cell growth, glucose consumption and products formation starting from different initial conditions.

Figure 21:
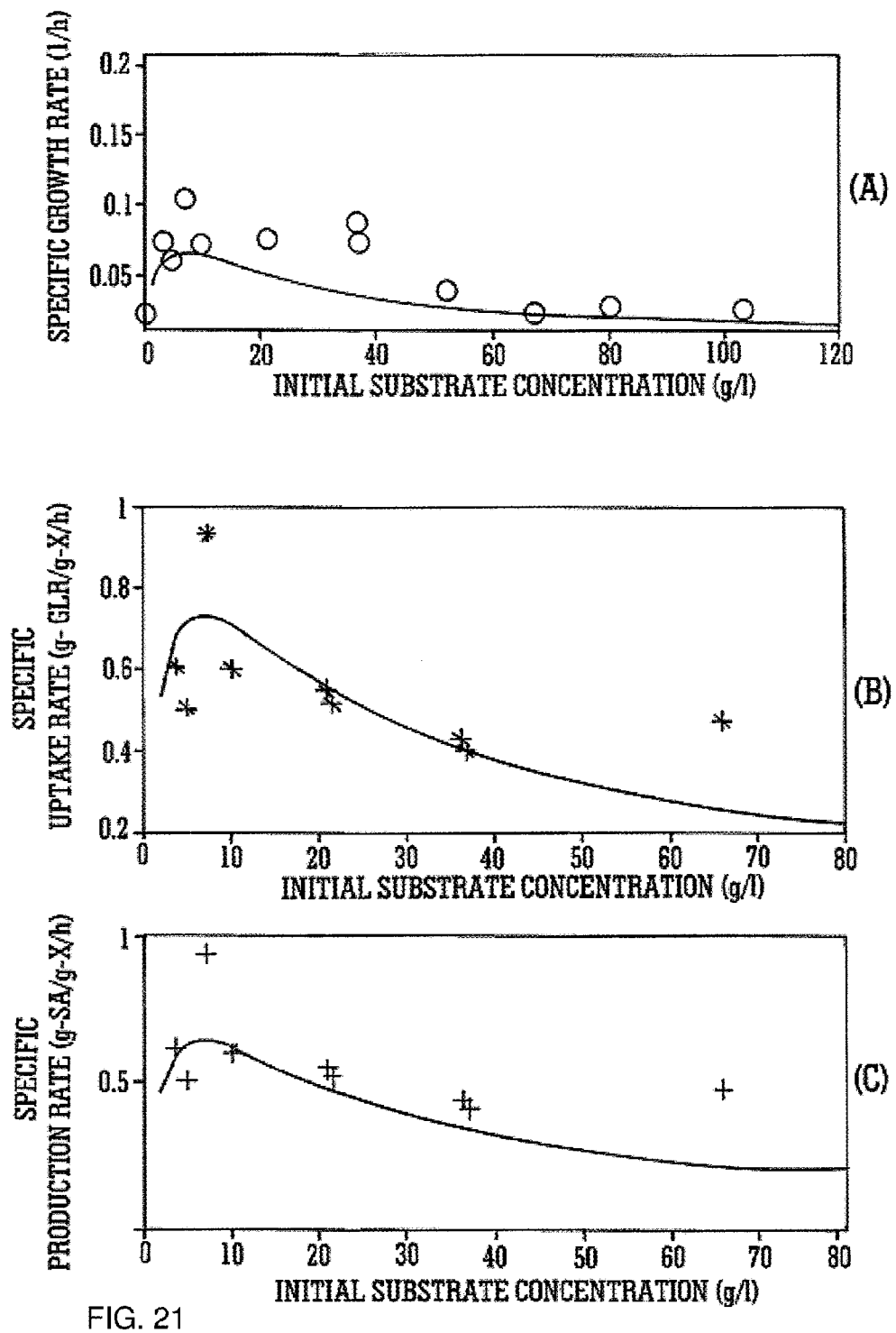

The parameter values of the unstructured model and the constraints used are presented in table 10. As mentioned in section 2.7, only the succinic acid concentration ($P_{SA}$, m=1) was considered in Eq.5 and Eq.86 as the only product inhibitor and the only product formed from substrate consumption respectively 3.2.1) Cell Growth FIG. 21A shows experimental and predicted values of the specific growth rate for different initial glycerol concentrations. Predicted values were calculated from the model while experimental values were assessed by plotting the logarithm of the cell growth, X, ln(X) versus time for each experiment and measuring the maximum gradient of this curve (results not shown). As it can be seen in FIGS. 19 and 21A Actinobacillus succinogenes can grow well in a wide range of initial glycerol concentrations and cell growth was even detected with initial concentrations above 100 g-$GLR_0$/L. The critical concentration of glycerol ($C^*_{GLR}$) where cells cease to grow was found to be around 140-160 g/L. The maximum specific growth rate, $\mu_{max}$, was 0.12 $h^{-1}$ and values of $K_S$ and $K_I$ were estimated to be 2.896 and 15.360 g-GLR/L respectively.

Cell growth was also affected by the organic acid concentrations produced during the batch process. Weak acids like acetic, formic and succinic acid can cause inhibition effect mainly due to their undissociated form [2.29, 2.30]. In this study, due to the low by-product formation in the methods of the invention, only the inhibition effect of succinic acid was considered. The critical value of this acid, above which cells do not grow, was taken from [2.35] and it was equal with 45.6 g/L. This high critical value indicates the great tolerance this microorganism shows to succinic acid and suggests it will be a capable candidate for industrial use.

FIG. 21A also shows specific growth rate $\mu$ ($h^{-1}$) is clearly affected by the initial glycerol concentration. In particular, it exhibits a maximum around 6-8 g-$GLR_0$/L while it decreases in high $S_o$ concentrations. Similar behaviour is revealed in FIGS. 21B and 21C for specific substrate uptake rate, $q_s$ (g-GLR/g-DCW h), and the specific production rate, $q_p$ (g-SA/g-DCW h). In both cases, a peak in p values is found at low $S_o$ concentrations, while $\mu$ decreases at higher $S_o$ concentrations. An important outcome is that $\mu$ is one order of magnitude lower than $q_s$ and $q_p$ indicating that, unlike glucose fermentation, cells prefer to consume glycerol for the production of succinic acid rather than for cell growth.

3.2.2) Substrate Consumption

Glycerol concentration was predicted based on a basic carbon mass balance where glycerol, the only carbon source, is converted to biomass, succinic acid and by-products. Also, we assume some small amount, $m_S$, is used for maintenance ($m_S$ was estimated to be 0.001 g-GLR/g-DCW h which is reasonable considering that A. succinogenes is a facultative anaerobe and thus the energy accounting for maintenance can be essentially ignored. The stoichiometric yields for biomass and succinic acid are equal to 0.130 g-DCW/g-GLR and 2.790 g-SA/g-GLR respectively. However, glycerol is not the only substrate in the medium as there is also $CO_2$ gas supplied during the fermentation. The current model, however, does not take into consideration $CO_2$ concentration or $CO_2$ flow rate since they cannot be measured on-line with conventional $CO_2$ analysers.

3.2.3.) Product Formation

The production of acids is modelled by the Luedeking-Piret model (Eq.7) [2.31] indicating that there are two kinetic parameters for each product, one growth associated term (product formation occurs at the same time as cell growth) and one non-growth associated term (product generation still occurs when growth has stopped i.e. in the stationary phase) that affect the profiles of the acids production. Both growth and non-growth associated parameters are reported in table 10.

In FIG. 19, the predicted and experimental values of the by-products are depicted. As mentioned earlier, the main two by-products formed are formic and acetic acid. Comparing the production of succinic acid with the other end products, it can be concluded that this bioprocess gives relatively small amounts of by-products for all the initial conditions. This is indicated by the averages of the values in table 7 showing the low mass ratios of formate to succinate and acetate to succinate which are 0.05 g-FA/g-SA and 0.08 g-AA/g-SA respectively.

3.3) Model Validation

Figure 22A:
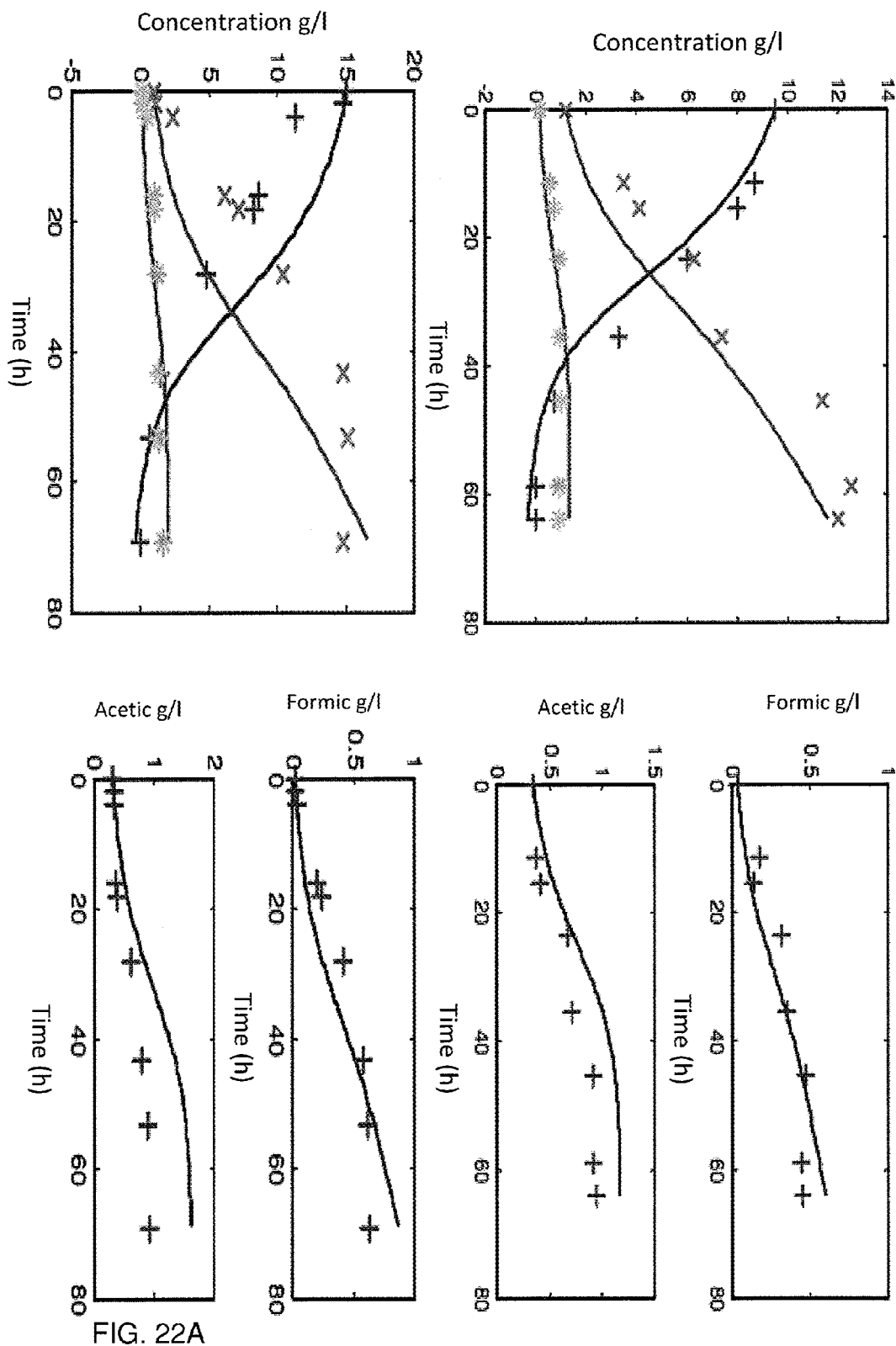
Figure 22B:
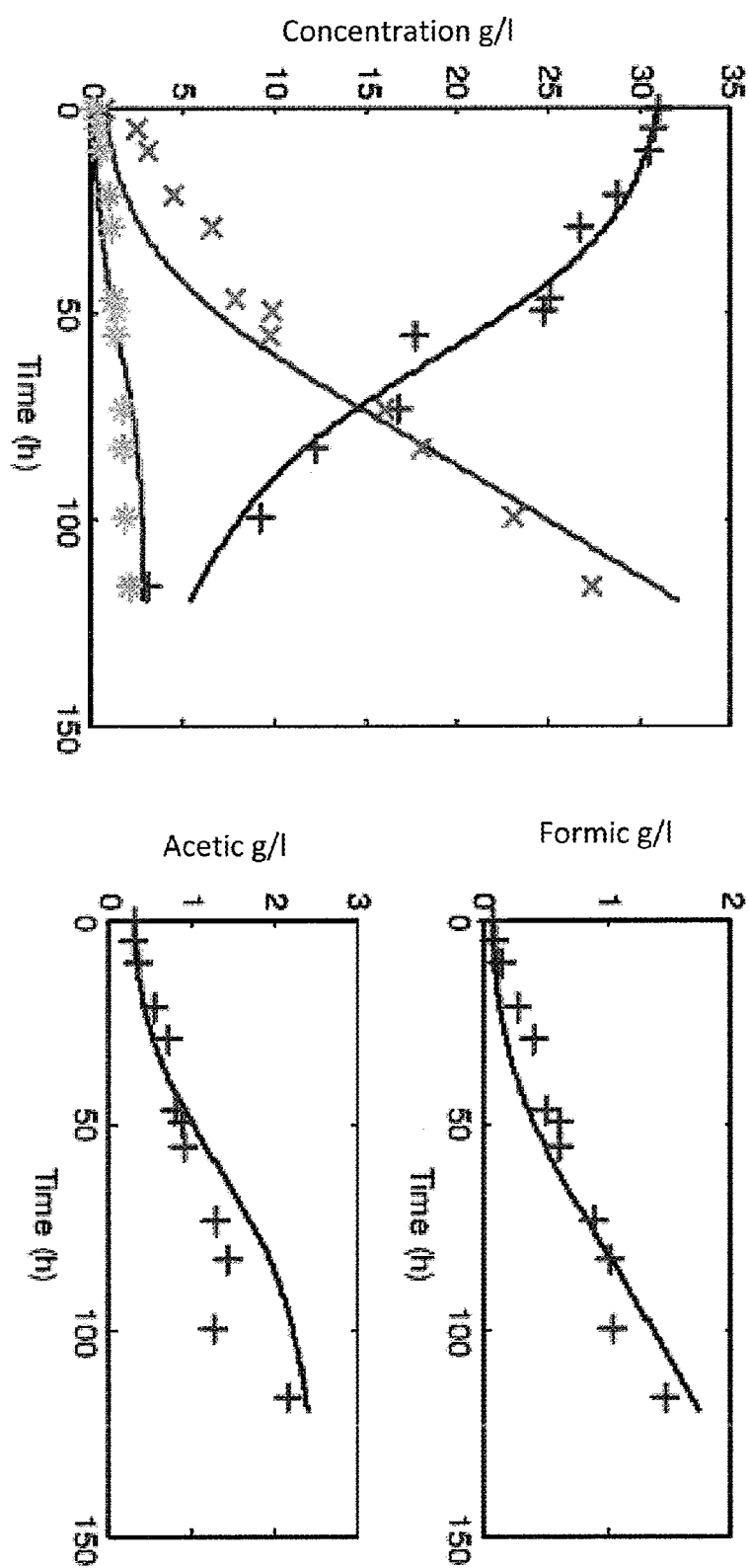

The final aim of this study was to validate the above unstructured model by testing its predictive capabilities for a scaled-up system. Thus, bench top rectors (1.8 L) were used in batch experiments for model validation. FIG. 22 shows the experimental results from the bench top reactors as well as the predicted values calculated from our model by using the kinetics obtained by fitting parameters to the SARs experiments. As it can be seen, our model can predict the bench-top batch experiments very well without any additional fitting for a wide range of initial conditions. Therefore, the model can be safely used to predict the dynamic behaviour of GLR-SA batch experiments.

Figure 23:
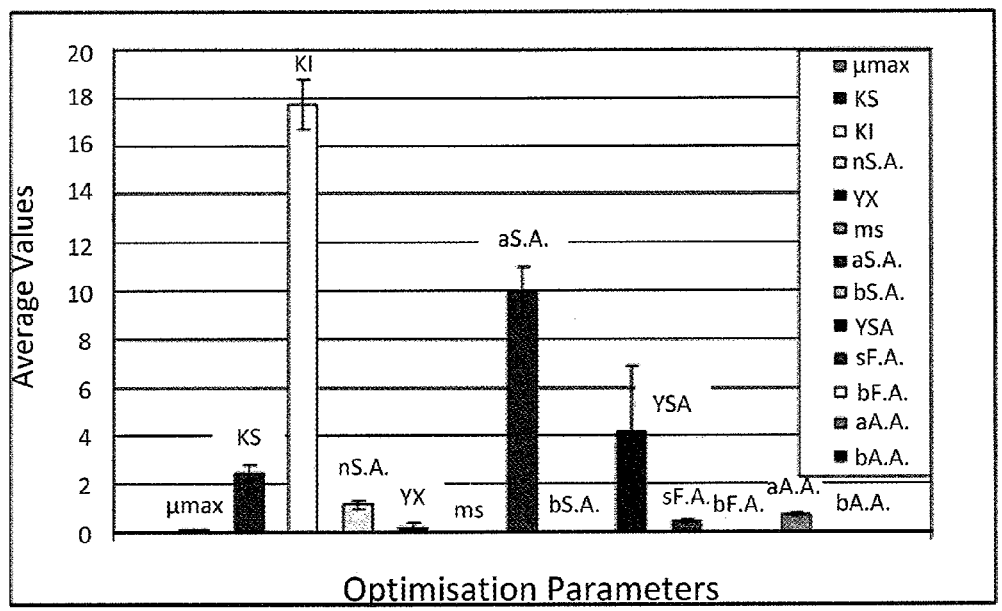

It should be noted here that multiple stochastic optimisation runs have been used in order to ensure that local optima were avoided. These runs produce families of solutions around the global optimum. These families of solutions are reported in table 11 for 15 runs. FIG. 23 depicts graphically the average values of the 13 parameters from these 15 runs as well as their standard deviation.

B4) Conclusions

The most significant feature of this work is that a method to produce high succinic acid concentrations from glycerol was successfully developed. In this study, an unstructured model was developed for the prediction of the batch succinic acid production from glycerol with different initial conditions where inhibitory effects of the substrate and products were taken into consideration. The estimated kinetic model fits well the experimental data in small anaerobic reactors for different initial conditions. Furthermore, the model can also be used with confidence in similar systems at larger scales as we demonstrated that the model can predict well experimental results for larger bench-top reactors. The proposed model can therefore be used for design and optimisation of batch and fed-batch processes.

The path to industrialisation for a (bio)-process is very demanding, as it should demonstrate high yields, productivities and high final product concentrations with low by-products formation to reduce the cost of recovering the products. The high yields and final succinic acid concentrations presented in this study illustrate the great potential of the Glycerol-Succinate system and can lay the foundations for an extensive research on this promising bioprocess. Optimising the succinic acid production from glycerol can result in high productivities and can play an important role in the sustainability of the biodiesel industry.

C Further Experimental Results

The following studies were undertaken to supplement and further investigate the information provided in the studies reported in Section B, above. These further studies investigated the impact of substrates on the ability of microorganism of the invention to convert glycerol to succinic acid, and also investigated the production of succinic acid in reaction vessels of different sizes.

C.1 Comparison of Conversion to Succinic Acid of Pure or Crude Forms of Glycerol The following study allowed investigation of the impact that the form of glycerol provided in a medium has on:
the ability of microorganism of the invention to convert glycerol to succinic acid; and
effectiveness of methods of the invention in producing succinic acid using such microorganisms.

Four Small Anaerobic Reactors (SARs) with a total volume of 250 mL and a working volume of 160 mL were set up as follows. Each contained either glycerol at an initial glycerol concentration of 20 g/L. Two of the SARs (designated "PURE1" and "PURE2") contained "pure" glycerol (commercially available laboratory reagent grade), while the other two SARs (designated "CRUDE1" and "CRUDE2") contained "crude" glycerol—a waste product derived from the manufacture of biodiesel. The main constituents of the crude glycerol used were: 69-73% glycerol, 14.5% water, 3.6% methanol, and traces of fatty acid methyl esters (FAMEs), mono-glycerides, and di-glycerides.

Microorganisms of the invention (specifically the bacteria deposited under the Budapest Treaty as described elsewhere in the specification) were introduced into the SARs as an inoculum of 10% v/v. The nutrients provided were the same (both in terms of constituents and amounts) as in the previous pure glycerol experiments described above.

$CO_2$ was provided to each of the SARs, at flow rates of 2.3 mL/minute (CRUDE1), 2.5 mL/minute (CRUDE2), 7.8 mL/minute (PURE1) and 4.4 mL/minute (PURE2). Cultures in the SARs were maintained for up to 55.5 hours, and samples taken for analysis at 0 hours, 24 hours, 48 hours, and at the end of the culture period.

Figure 24:
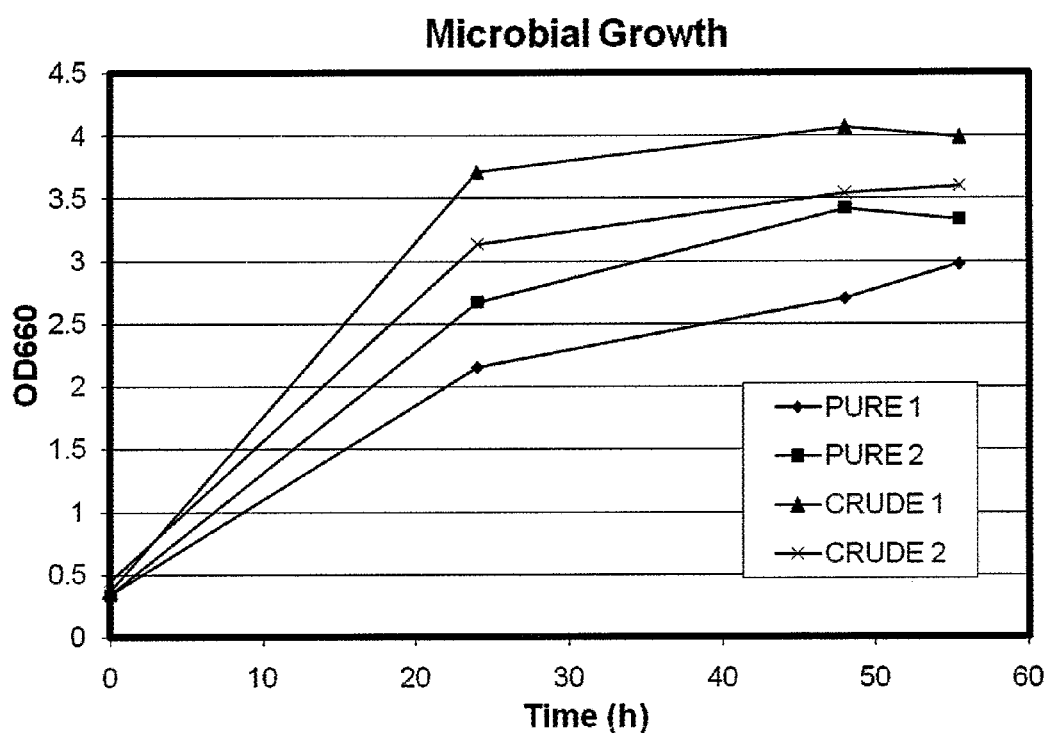

The results of this analysis are shown in FIG. 24, in which the X axis indicates time in culture, and the Y axis indicates optical density (OD) at 660 nm. Increasing optical density is indicative of increasing numbers of microorganisms present in the SARs. Since the microorganisms all utilise glycerol as a substrate for metabolism, such an increase in microorganism numbers is taken to be representative of increasing succinic acid generation.

As can be seen from FIG. 24, the microorganisms of the invention not only successfully grew in media containing the "crude" glycerol, but actually exhibited better growth in such media than in those containing "pure" glycerol. This clearly illustrates that even impure forms of glycerol provide substrates that are highly suitable for conversion to produce succinic acid by the microorganisms of the invention (for example in the methods of the invention). This finding may be viewed as surprising, since the microorganisms of the invention were "trained" using media comprising pure glycerol, and since it may otherwise have been expected that some of the impurities in the crude glycerol (such as methanol) would exert a deleterious effect on proliferation and activity of the microorganisms. Without wishing to be bound by any hypothesis, the inventors believe that certain compounds present in the crude glycerol (such as the FAMEs, mono-glycerides, or di-glycerides) may function as nutrients promoting the proliferation and function of the microorganisms, and overcoming the anticipated disadvantages. Alternatively or additionally, microorganism may be promoted by the provision of $CO_2$ to the SARs at lower flow rates as discussed for the case of experiments with pure glycerol, confirming that relatively low $CO_2$ flow rates are more desirable for higher cell growth.

Irrespective of the reason for the improved growth of the microorganisms of the invention on such crude glycerol substrates, the skilled person will readily appreciate that these results indicate a surprisingly effective utility of the microorganisms and/or methods of the invention in the production of succinic acid from glycerol found in "waste" or "by" products of other industrial processes such as bio-diesel production.

C.2 Comparison of Conversion to Succinic Acid of Pure and Crude Forms of Glycerol in Different Size Fermenters.

That the results reported in section C.1, above, in connection with SARs are also applicable to larger reactors and reaction mixtures was illustrated by a further study, in which bacteria (produced by the training methods of the invention specifically those deposited under the Accession No. NCIMB 41825) were incubated with either:

"pure" glycerol in a SAR; or
"crude" glycerol in a 2 L reactor.

The same concentration of glycerol (20 g/L) was used as for the preceding studies. $CO_2$ was provided at a flow rate of 8 ml/min for the SARs and 12 ml/min for the 2 L reactor.

Figure 25:
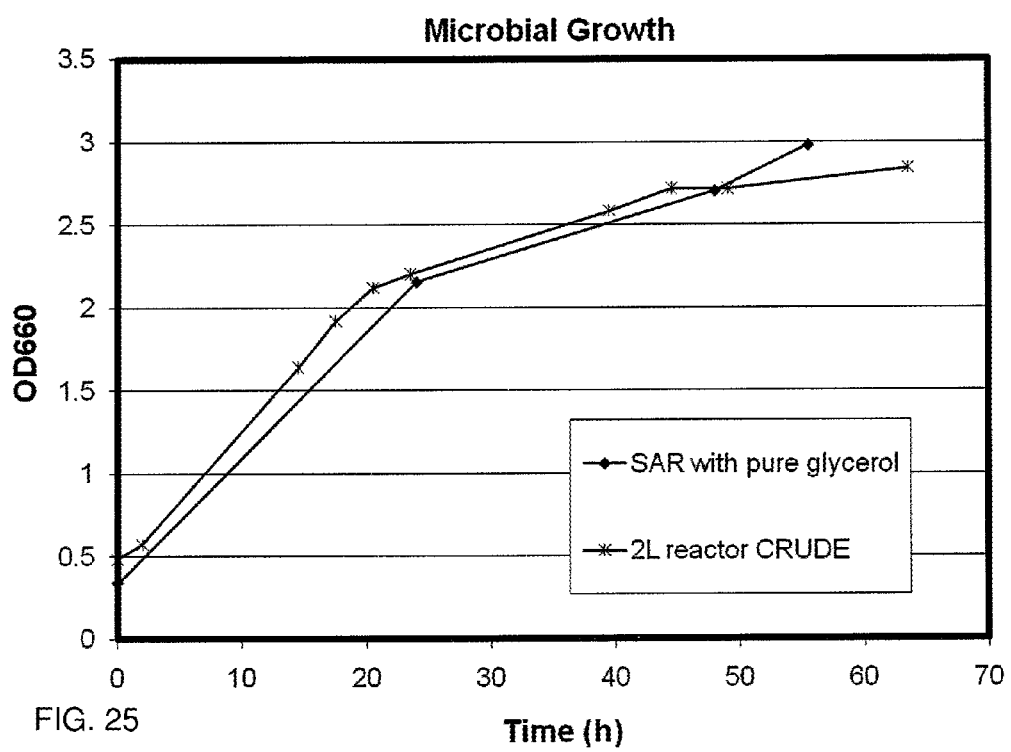

The results of this study are shown in FIG. 25, which compares growth of microorganisms of the invention when provided with these different glycerol-containing substrates in different sizes of reaction vessels. As before, Optical Density (OD) at 660 nm is shown on the Y axis, and time in culture is shown on the X axis.

FIG. 25 illustrates that the results achieved in the SAR study are also applicable to larger reactors. The two growth curves shown in this Figure follow a similar pattern, and similar "final" OD values are achieved in both cases. These results provide further confidence that "crudeness" of the glycerol source does not adversely impact upon succinic acid generation, and also indicate that data generated in smaller reactors can be validly extrapolated to larger systems.

C.3 Scale Up of Conversion to Succinic Acid of Pure Glycerol

Further "scale up" experiments using the microorganisms and methods of the invention were conducted to compare results achieved using 2 L and 10 L bioreactors.

Microorganisms of the invention (specifically those deposited under the Accession No. NCIMB 41825) were incubated in either 2 L or 10 L bioreactors containing "pure" glycerol at an initial concentration of 20 g/L. Incubation time for the 2 L reactor was 72 hrs and for the 10 L reactor was 142 hrs.

At the end of incubation the yield of succinic acid (measured in grams succinic acid generated per gram of glycerol) and final concentration of succinic acid achieved were both assessed. The results of these assessments are shown in FIGS. 26 and 27 respectively.

Figure 26:
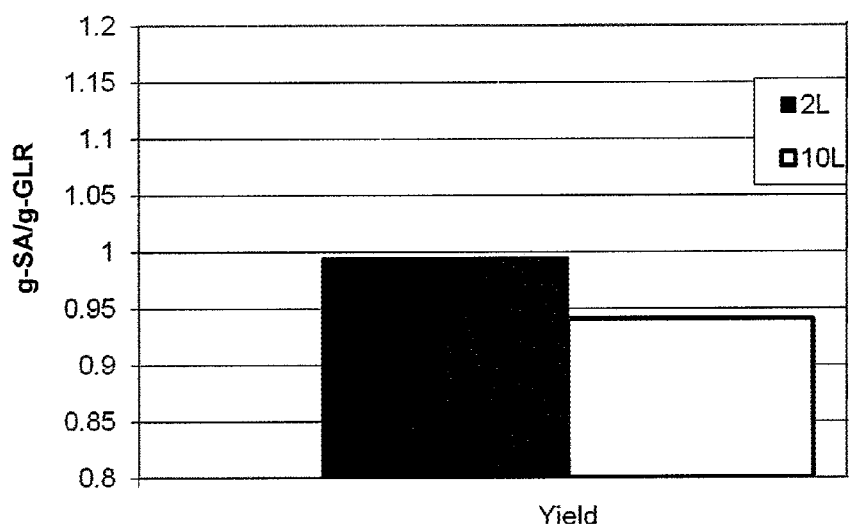

In FIG. 26 it can be seen that microorganisms and methods of the invention were able to convert most of the glycerol present into succinic acid. Incubation in the 10 L reactor achieved a yield of 0.94 grams of succinic acid per gram of glycerol present in the starting mixture, while incubation in the 2 L reactor achieved a yield of 0.99 grams of succinic acid per gram of initial glycerol.

FIG. 27 illustrates that the microorganisms and methods of the invention are able to achieve high final concentrations of succinic acid in both 2 L and 10 L cultures. While the final concentration achieved in the 10 L reactors was lower than that achieved in the 2 L reactors (indicating that future optimisation of this technique may remain valuable), both sets of conditions achieved final concentrations that compare favourably with values reported in the prior art.

The results of these studies thus illustrate that the microorganisms and methods of the invention are capable of generating high concentrations, and high yield, of succinic acid from both pure and crude glycerol sources. These results can be achieved in a range of reactors of different sizes, indicating that the methods are eminently suitable to "scale up" to industrially relevant levels, and that data produced in small experimental models can be extrapolated to larger applications.

FIGURE LEGENDS

Figure 2:
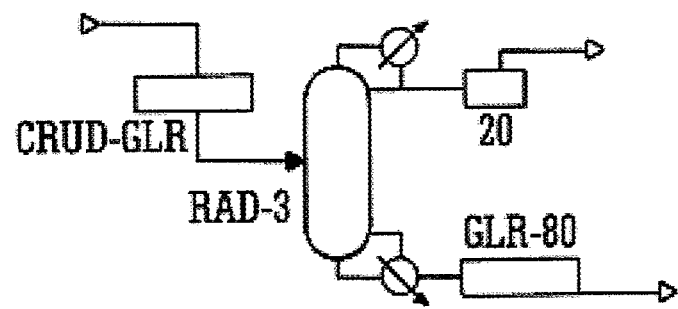
Figure 13:
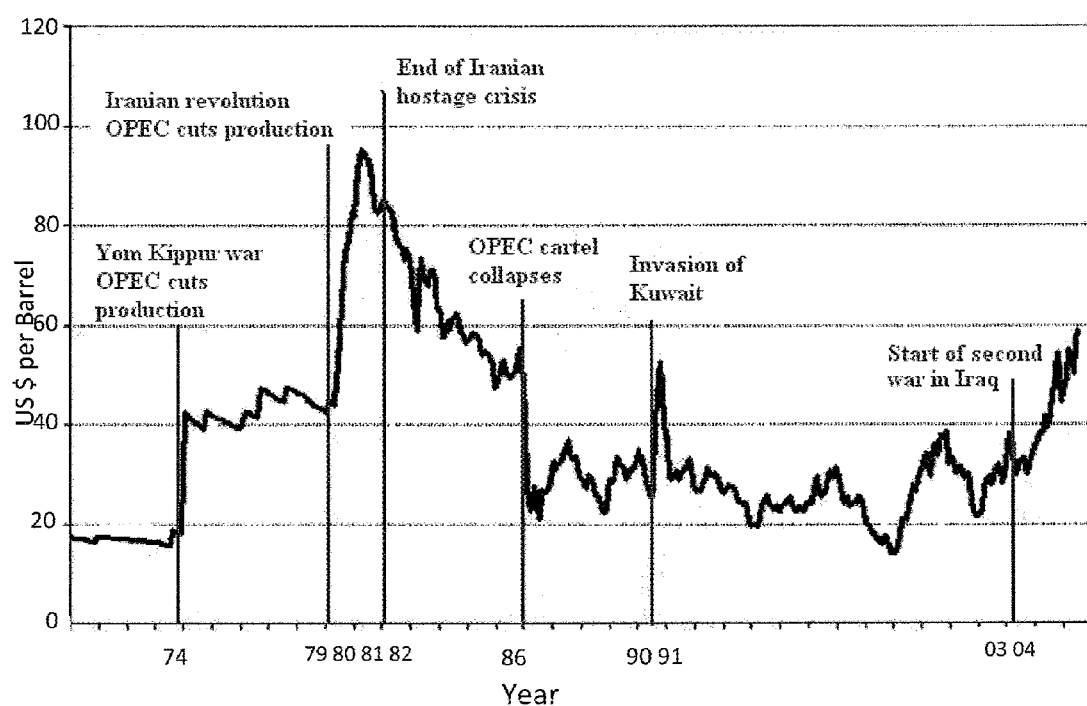
Figure 14:
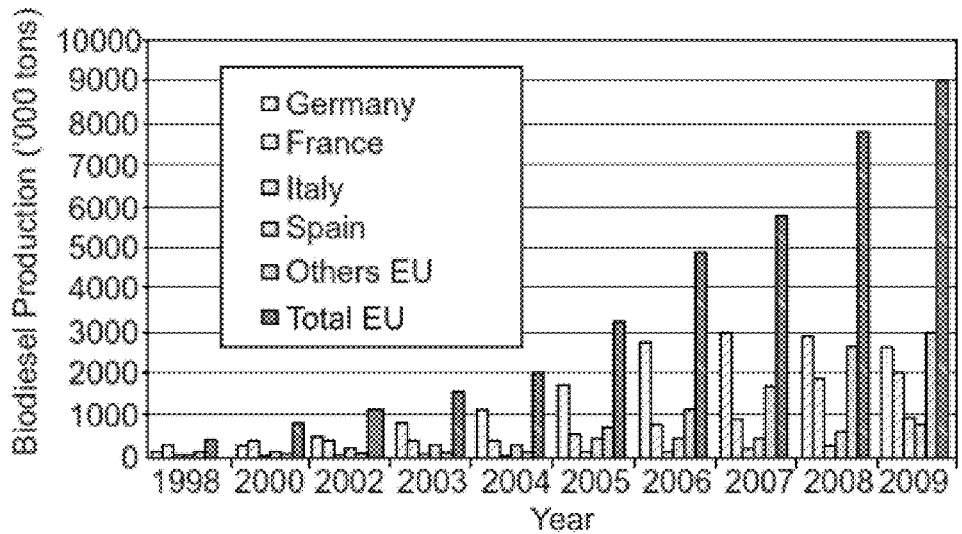
Figure 15:
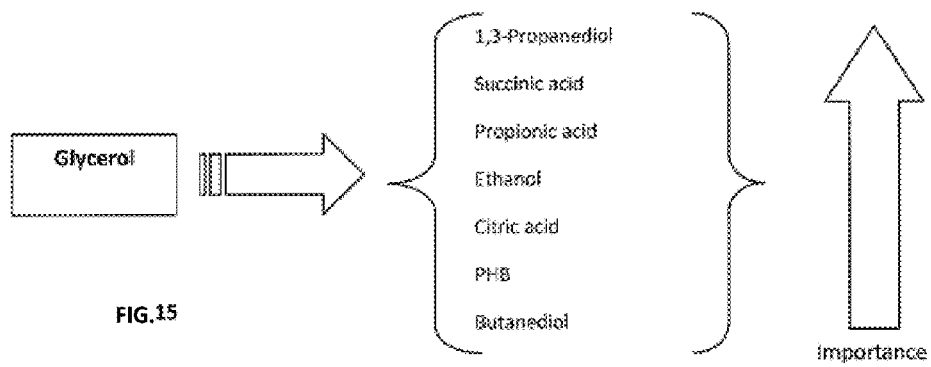
Figure 16:
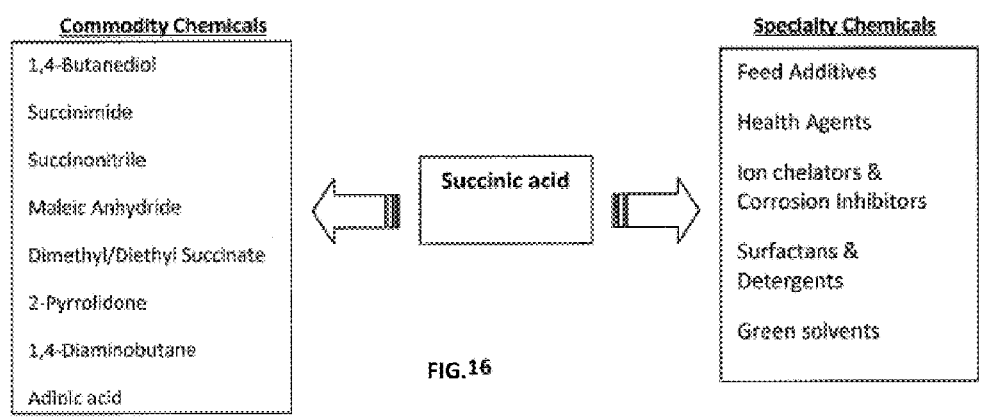

FIG. 1
Biodiesel production flowsheet diagram developed in Aspen Plus (Scenario 0)
FIG. 2
Distillation of crude glycerine to GLR 80% Scenario 1 (The same configuration with different column specifications works for GLR 95%—Scenario 2)
FIG. 3
Fermantation of crude glycerol to succinate and its recovery to succinic acid crystals: Scenario 3 (flowsheet developed in Aspen Plus)
FIG. 4
Distribution of the Bare Module Cost for Scenario 3.
FIG. 5
Distribution of the energy consumption for the succinate case (Scenario 3)
FIG. 6
NPV Results from the two-parameter search taking into account cycle times (kk1) and water flowrates (kk2)
FIG. 7
The NPV of the four schemes
FIG. 8
Profitability criteria for the four schemes
FIG. 9
NPV values versus time for all the examined schemes
FIG. 10
IRR Values for the four cases with respect to lifespan FIG. 11
FIG. 11
Sensitivity analysis on prices to plant's profitability
FIG. 12
Multi-objective optimisation for profits and emissions
FIG. 13
Diagram of petroleum oil price variations through the years [6]. Source: Federal Reserve Bank of St. Louis and Bureau of Labour Statistics in LEMIEUX (2006)
FIG. 14
Biodiesel Production in European Union countries in the last eleven years [8]. Source: European Board of Biodiesel, www.ebb-eu.org
FIG. 15
Bioconversion routes of glycerol to value added chemicals
FIG. 16
Succinic acid as a building block for the production of various chemicals [20,24]

FIG. 17

Typical fermentation profile in SARs: (A) production of cells (♦) and succinic acid (■) from glycerol (▲). (B) Formation of by-productd: formic (♦) and acetic (■) acid.

FIG. 18

HPLC chromatograms from: A) the RI detector and B) from the UV detector. Blue peaks are from a mixed standard solution while the red and grey lines are typical fermentation samples.

FIG. 19

Experimental and predicted values in the SARs with different initial conditions (3.7, 5.1, 7.2, 10.0, 21.5, 36.4 g-$GLR_0$/L).

FIG. 20

By-products profiles in SARs with different initial conditions (3.7, 5.1, 7.2, 10.0, 21.5, 36.4 g-$GLR_0$/L).

FIG. 21

Specific rates experimental results (symbols) and model predictions (solid lines) versus initial glycerol concentrations. (A) specific growth rate: $\mu$, (B) specific uptake rate: $q_s$ and (C) specific production rate: $q_p$

FIGS. 22A-22B

Simulated (solid lines) vs. experimental (symbols) results in bench-top reactors, using the kinetics from the experiments in SARs.

FIG. 23

Average values and standard deviations for the optimisation parameters from multiple optimisation runs

FIG. 24

Microbial growth of four SARs containing pure (PURE 1 and PURE 2) or crude (CRUDE 1 and CRUDE 2) glycerol

FIG. 25

Fermentation results for different systems and different glycerol sources.

FIG. 26

Yield values at the end of the fermentation cycle from 2 L and 10 L bioreactors

FIG. 27

Final succinic acid concentrations from 2 L and 10 L bioreactors

FIGS. 28A-28K

Table 1-Table11

REFERENCES 1.1. V. Smil, 2005, Energy at the crossroads: Global perspectives and uncertainties, MIT Press, Cambridge.
1.2. M. Jaccard, 2005, Sustainable fossil fuels: The unusual suspect in the quest for clean and enduring energy, Cambridge University Press, Cambridge.
1.3. Demirbas, 2008, Biodiesel: A Realistic Fuel Alternative for Diesel Engines, Springer-Verlag London Limited.
1.4. Rosch, J. Skarka, The European biofuels policy and sustainability, International Association for energy economics, third quarter 2009.
1.5. United States Environmental Protection Agency, Office of Transportation and Air Quality EPA-420-F-10-056, November 2010.
1.6. OECD-FAO Agricultural Outlook 2010-2019, http://www.agri-outlook.org/document/9/0,3746, en_36774715_36775671_45438665_1_1_1_1,00.html
1.7. European Board of Biodiesel, www.ebb-eu.org.
1.8. R. Kotrba, L. Geiver, E. Voegele, Global Biodiesel Production and Market Report, Biodiesel magazine, http://www.biodieselmagazine.com/article.jsp?article_id=4447&q=page=1.
1.9. S. Scott, M. Davey, J. Dennis, I. Horst, C. Howe, D. Lea-Smith, A. Smith Biodiesel from algae: challenges and prospects, Current Opinion in Biotechnology, 21 (2010) 277-286.
1.10. Y. Li, Z. Zhaob, F. Bai, High-density cultivation of oleaginous yeast *Rhodosporidium toruloides* Y4 in fed-batch culture, Enzyme and Microbial Technology, 41 (2007) 312-317.
1.11. T. Rice, Meals per gallon: The impact of industrial biofuels on people and global hunger, January 2010, ActionAid.
1.12. Carraretto, A. Macor, A. Mirandola, A. Stoppato, S. Tonon, Biodiesel as alternative fuel: Experimental analysis and energetic evaluations, Energy 29 (2004) 2195-2211.
1.13. Y. Zhang, M. Dube, D. McLean, M. Kates, Biodiesel production from waste cooking oil: 1. Process design and technological assessment, Bioresource technology, 89 (2003) 1-16.
1.14. Y. Zhang, M. Dube, D. McLean, M. Kates, Biodiesel production from waste cooking oil: 2. Economic assessment and sensitivity analysis, Bioresource Technology, 90 (2003) 229-240.
1.15. J. Marchetti, V. Miguel, A. Errazu, Techno-economic study of different alternatives for biodiesel production, Fuels Processing Technology, 89 (2008) 740-748.
1.16. Apostolakou, I. Kookos, C. Marazioti, K. Angelopoulos, Techno-economic analysis of a biodiesel production process from vegetable oils, Fuel Process. Technol., 90 (2009) 1023-1031.
1.17. Singhabhandhu, T. Tezuka, A perspective on incorporation of glycerin purification process in biodiesel plants using waste cooking oil as feedstock, Energy 35 (2010) 2493-2504.
1.18. West, D. Posarac, N. Ellis, Assessment of four biodiesel production processes using HYSYS. Plant, Bioresource Technology 99 (2008) 6587-6601.
1.19. M. Haas, A. McAloon, W. Yee, T. Foglia, A process model to estimate biodiesel production costs, Bioresource Technology 97 (2006) 671-678.
1.20. M. Binns, A. Vlysidis, C. Theodoropoulos, Assessment of economic and environmental cost-benefits of developed biorefinery schemes, in Advanced Oil Crop Biorefineries (RSC Green Chemistry) 2011.
1.21. J. Thompson, B. He, Characterization of crude glycerol from biodiesel production from multiple feedstocks, Appl. Eng. Agric., 22 (2006) 261-265.
1.22. Johnson, K. Takoni, The glycerine glut: Options for the value-added conversion of crude glycerol resulting from biodiesel production, Environ. Progr., 26 (2007) 338-348.
1.23. M. Pagliaro, M. Rossi, The future of glycerol: New uses of a versatile raw material, RSC Publishing, Cambridge, UK, 2008.
1.24. Vlysidis, M. Binns, C. Webb, C. Theodoropoulos, Glycerol utilization for the production of chemicals: conversion to succinic acid, a combined experimental and computational study, Biochem. Eng. J., 2010, submitted.
1.25. P. Lee, W. Lee, S. Lee, H. Chang, Succinic acid production with reduced by-product formation in the fermentation of *Anaerobiospirillum succiniciproducens* using glycerol as a carbon source, Biotechnol. Bioeng., 72 (2001) 41-48.
1.26. Y. Dharmadi, A. Murarka, R. Gonzalez, Anaerobic Fermentation of glycerol by *Escherichia coli*: a new platform for metabolic engineering, Biotechnol. Bioeng., 94 (2006) 821-829.

1.27. J. McKinlay, C. Vieille, J. Zeikus, Prospects for a bio-based succinate industry, Appl. Microbiol. Biotechnol. 76 (2007) 727-740.

1.28. Du., S. Lin, A. Koutinas, R. Wang, P. Dorado, C. Webb, A wheat biorefining strategy based on solid-state fermentation for fermentative production of succinic acid, Bioresour. Technol., 99 (2008) 8310-8315.

1.29. Z. Hua, P. Tan, X. Yan, D. Lou, Life cycle energy, environment and economic assessment of soybean-based biodiesel as an alternative automotive fuel in China, Energy 33 (2008) 1654-1658.

1.30. Iliopoulos, S. Rozakis, Environmental cost-effectiveness of biodiesel production in Greece: Current policies and alternative scenarios, Energy Policy 38 (2010) 1067-1078.

1.31. Azapagic, R. Clift, The application of life cycle assessment to process optimisation, Computers and Chemical Engineering, 23 (1999) 1509-1526.

1.32. K. Komers, F. Skopal, R. Stloukal, J. Machek, Kinetics and mechanism of the KOH—catalysed methanolysis of rapeseed oil for biodiesel production, European journal of lipid science and technology, 104 (2002) 728-737.

1.33. Rapeseed varieties SAC (2008). Oilseed Rape. http://www.sac.ac.uk/mainrep/pdfs/osr2008northuk.pdfaccessed 14/7/2009.

1.34. Centre technique interprofessionnel des oleagineux metropolitains, www.cetiom.fr, Personal communication.

1.35. CREOL, http://www.creol.fr, Personal communication.

1.36. Desmet Ballestra, http://www.desmetballestra.com/, Personal communication.

1.37. R. Harrison, P. Todd, S. Rudge, D. Petrides, Bioseparations science and engineering, Oxford University Press, Inc., New York, 2003.

1.38. Q. Li, D. Wang, Y. Wu, W. Li, Y. Zhang, J. Xing, et al. One step recovery of succinic acid from fermentation broths by crystallization, Separation and purification technology, 72 (2010) 294-300.

1.39. R. Turton, C. Bailie, B. Whiting, A. Shaeiwitz, Analysis, Synthesis and Design of Chemical Processes, 2009, Third edition, Pearson Education, Inc.

1.40. Chemical Engineering, www.che.com, May 2009.

1.41. S. Kirkpatrick, D. Gelatt, P. Vecchi, Optimisation by simulated annealing, Science, 220 (1983) 671-680.

1.42. Global Emission Model for Integrated Systems (GEMIS) database, http://www.oeko.de/service/gemis/en/, accessed 30/06/2009.

1.43. FERA, The Food and Environment Research Agency, (2009). Personal Communications.

1.44. The European Energy Exchange http://www.eex.com/en/Market%20Data/Trading%20Data/Emission%20Rights/EU%20Emission%20Allowances%20%7C%20Spot.

1.45. ICIS, http://www.icis.com/home/default.aspx.

1.46. Agricommodity prices, www.Agricommodityprices.com, accessed 14/12/2009.

1.47. H. Song, S. Lee, Production of succinic acid by bacterial fermentation, Enzyme and Microbial Technology, 39 (2006) 352-361.

1.48. Food and Agricultural Organisation of the United Nations, FAO statistics, http://faostat.fao.org/default.aspx.

1.49. P. Taylor, Royal society of chemistry, Biosuccinic acid ready for take off?, 21 Jan. 2010, http://www.rsc.org/chemistryworld/News/2010/January/21011003.asp.

2.1. Directive 2003/30/EC of the European Parliament and of the council of May 2003 on the promotion of the use of biofuels or other renewable fuels for transport, Official Journal of the European Union.

2.2. M. Kojima, T. Johnson, Potential for Biofuels for transport in developing countries, ESMAP, Washington, D.C., 2005.

2.3. M. Carriquiry, U.S. Biodiesel production: Recent developments and prospects, Iowa Ag. Review, 13 (2007) 8-11.

2.4. http://www.biodiesel.org/, the official site of the national biodiesel board, (last time assessed 20 Nov. 2009).

2.5. D. Bajpai, V. K. Tyagi, Biodiesel: source, production, composition, properties and its benefits, J. Oleo Sci., 55 (2006) 487-502.

2.6. (FIG. 1) Source: Federal Reserve Bank of St. Louis, and Bureau of Labor Statistics in LEMIEUX (2006).

2.7. Worldwatch Institute, Biofuels for transportation: global potential and implications for sustainable energy and agriculture, Earthscan, London, UK, 2007.

2.8. European Board of Biodiesel, www.ebb-eu.org, (last time assessed 16 Nov. 2010).

2.9. J. C. Thompson, B. B. He, Characterization of crude glycerol from biodiesel production from multiple feedstocks, Appl. Eng. Agric., 22 (2006) 261-265.

2.10. D. T. Johnson, K. A. Takoni, The glycerine glut: Options for the value-added conversion of crude glycerol resulting from biodiesel production, Environ. Progr., 26 (2007) 338-348.

2.11. M. Pagliaro, M. Rossi, The future of glycerol: New uses of a versatile raw material, RSC Publishing, Cambridge, UK 2008 (chapter 10).

2.12. G. Graff, Glycerin glut sends prices plummeting, Purchasing, Jun. 15, 2006, http://www.purchasing.com/article/print/213801-Glycerin_glut_sends_prices_plummeting.php, (last time assessed 20 Nov. 2009).

2.13. E. H. Himmi, A. Bories, F. Barbirato, Nutrient requirements for glycerol conversion to 1,3-propanediol by *Clostridium butyricum*, Bioresour. Technol., 67 (1999) 123-128.

2.14. T. Homann, C. Tag, H. Biebl, W. D. Deckwer, B. Schink, Fermentation of glycerol to 1,3-propanediol by *Klebsiella* and *Citrobacter* strains, Appl. Microbiol. Biotechnol., 33 (1990) 121-126.

2.15. P. C. Lee, W. G. Lee, S. Y. Lee, H. N. Chang, Succinic acid production with reduced by-product formation in the fermentation of *Anaerobiospirillum succiniciproducens* using glycerol as a carbon source, Biotechnol. Bioeng., 72 (2001) 41-48.

2.16. Y. Dharmadi, A. Murarka, R. Gonzalez, Anaerobic Fermentation of glycerol by *Escherichia coli*: a new platform for metabolic engineering, Biotechnol. Bioeng., 94 (2006) 821-829.

2.17. E. H. Himmi, A. Bories, A. Boussaid, L. Hassani, Propionic acid fermentation of glycerol and glucose by *Propionibacterium acidipropionici* and *Propionibacterium freudenreichii* ssp. shermanii, Appl. Microbiol. Biotechnol., 53 (2000) 435-440.

2.18. S. Papanikolaou, G. Aggelis, Modelling aspects of the biotechnological valorisation of raw glycerol: production of citric acid by *Yarrowia lipolytica* and 1,3-propanediol by *Clostridium butyricum*, J. Chem. Technol. Biotechnol., 78 (2003) 542-547.

2.19. T. Werpy, G. Petersen, Top Value Added Chemicals from Biomass Volume I—Results of Screening for Potential Candidates from Sugars and Synthesis Gas, US Department of energy, 2004.

2.20. J. G. Zeikus, M. K. Jain, P. Elankovan, Biotechnology of succinic acid production and markets for derived industrial products, Appl. Microbiol. Biotechnol., 51 (1999) 545-552.
2.21. M. V. Guettler, D. Rumler, M. K. Jain, *Actinobacillus succinogenes* sp. nov., a novel succinic-acid-producing strain from the bovine rumen, Int. J. System. Bacteriol., 49 (1999) 207-216.
2.22. J. B. McKinlay, J. G. Zeikus, C. Vieille, Insights into *Actinobacillus succinogenes* fermentative metabolism in a chemically defined growth medium, Appl. Environ. Microbiol., 71 (2005) 6651-6656.
2.23. C. Du., S. K. C. Lin, A. Koutinas, R. Wang, P. Dorado, C. Webb, A wheat biorefining strategy based on solid-state fermentation for fermentative production of succinic acid, Bioresour. Technol., 99 (2008) 8310-8315.
2.24. J. B. McKinlay, C. Vieille, J. G. Zeikus, Prospects for a bio-based succinate industry, Appl. Microbiol. Biotechnol. 76 (2007) 727-740.
2.25. E. Scholten, D. Dagele, Succinic acid production by a newly isolated bacterium, Biotechnol. Lett., 30 (2008) 2143-2146.
2.26. M. V. Guettler, J. K. Mahendra, S. K. Bhupendra, Process for making succinic acid, microorganisms for use in the process and methods of obtaining the microorganisms, U.S. Pat. No. 5,723,322, 1998.
2.27. J. C. Van Den Heuvel, H. H. Beeftink, Kinetic effects of simultaneous inhibition by substrate and product, Biotechnol. Bioeng., 31 (1988) 718-724.
2.28. J. F. Andrews, A mathematical model for the continuous culture of microorganisms utilizing inhibitory substrates, Biotechnol. Bioeng., 10 (1968) 707-723.
2.29. O. Levenspiel, The monod equation: a revisit and a generalization to product inhibition situations, Biotechnol. Bioeng., 22 (1980) 1671-1687.
2.30. F. Monot, J. M. Engasser, H. Petitdemange, Influence of pH and undissociated butyric acid on the production of acetone and butanol in batch cultures of *Clostridium acetobutylicum*, Appl. Microbiol. Biotechnol., 19 (1984) 422-426.
2.31. R. Luedeking, E. L. Piret, A kinetic study of the lactic acid fermentation. Batch process at controlled pH, J. Biochem. Microbiol. Technol. Eng., 1 (1959) 393-412.
2.32. H. Song, S. H. Jang, J. M. Park, S. Y. Lee, Modeling of batch fermentation kinetics for succinic acid production by *Mannheimia succiniciproducens*, Biochem. Eng. J., 40 (2008) 107-115.
2.33. A. A. Koutinas, R. Wang, I. K. Kookos, C. Webb, Kinetic parameters of *Aspergillus awamori* in submerged cultivations on whole wheat flour under oxygen limiting conditions, Biochem. Eng. J., 16 (2003) 23-34.
2.34. A. A. Koutinas, N. Arifeen, R. Wang, C. Webb, Cereal-based biorefinery development: Integrated enzyme production for cereal flour hydrolysis, Biotechnol. Bioeng., 97 (2007) 61-72.
2.35. S. K. C. Lin, C. Du, A. Koutinas, R. Wang, C. Webb, Substrate and product inhibition kinetics in succinic acid production by *Actinobacillus succinogenes*, Biochem. Eng. J., 41 (2008) 128-135.
2.36. M. J. Van der Wert, M. V. Guettler, M. K. Jain, J. G. Zeikus, Environmental and physiological factors affecting the succinate product ratio during carbohydrate fermentation by *Actinobacillus* sp.130Z, Arch. Microbiol., 167 (1997) 332-342.
2.37. N. S. Samuelov, R. Lamed, S. Lowe, J. G. Zeikus, Influence of $CO_2$—$HCO_3^-$ levels and pH on growth, succinate production, and enzyme activities of *Anaerobiospirillum succiniciproducens*, Appl. Environ. Microbiol., 57 (1991) 3013-3019.
2.38. Y. P. Liu, P. Zheng, Z. H. Sun, Y. Ni, J. J. Dong, P. Wei, Strategies of pH control and glucose-fed batch fermentation for production of succinic acid by *Actinobacillus succinogenes* CGMCC1593, J. Chem. Technol. Biotechnol., 83 (2008) 722-729.
2.39. H. Biebl, S. Marten, H. Hippe, W. D. Deckwer, Glycerol conversion to 1,3-propanediol by newly isolated clostridia, Appl. Microbiol. Biotechnol., 36 (1992) 592-597.
2.40. H. Song, J. W. Lee, S. Choi, J. K. You, W. H. Hong, S. Y. Lee, Effects of dissolved $CO_2$ levels on the growth of *Mannheimia succiniciproducens* and succinic acid production, Biotechnol. Bioeng., 98 (2007) 1296-1304.

The invention claimed is:
1. A method of generating an *Actinobacillus succinogenes* bacterium with improved ability to convert glycerol to succinic acid, the method comprising:
   a) combining a starter strain of *Actinobacillus succinogenes* with ability to convert glycerol to succinic acid and a medium containing an initial concentration of between 10 g/L and 60 g/L glycerol to produce a fermentation mixture;
   b) allowing fermentation to occur such that succinic acid is produced;
   c) assaying for an indication of glycerol metabolism; and
   d) generating the *Actinobacillus succinogenes* bacterium with improved ability to convert glycerol to succinic acid relative to the starter strain of *Actinobacillus succinogenes*
   wherein the *Actinobacillus succinogenes* starter strain corresponds to the strain deposited as American Type Culture Collection Number 55618 (ATCC No. 55618).
2. A method according to claim 1, further comprising repeating steps a) and b) and/or further comprising repeating step c).
3. A method according to claim 1, comprising between 4 and 19 repetitions of steps a) and b).
4. A method according to claim 1, wherein the assay for an indication of glycerol metabolism is a cell growth assay.
5. A method according to claim 1, wherein the assay for an indication of glycerol metabolism is an assay for production of succinic acid.
6. A method according to claim 1, wherein the fermentation mixture comprises glycerol at an initial concentration of between 10 g/L and 25 g/L.
7. A method according to claim 1, wherein a final concentration of 20 g/L or more of succinic acid is produced.
8. A method according to claim 1, wherein the succinic acid is produced at a yield of 0.7 or more units of succinic acid produced per unit of glycerol.
9. A method of producing succinic acid from glycerol, the method comprising:
   a) mixing an *Actinobacillus succinogenes* bacterium with improved ability to convert glycerol to succinic acid produced by the method of claim 1 and a medium comprising an initial concentration of between 10 g/L and 60 g/L glycerol to produce a fermentation mixture; and
   b) incubating the fermentation mixture, under conditions that promote fermentation to produce succinic acid, until succinic acid is produced.
10. A method according to claim 9, wherein the medium comprises crude glycerol.

11. A method according to claim 9, wherein the initial concentrations of carbon, nitrogen and phosphorous within the fermentation mixture are in the region of:
C: 2-20 g/L
N: 2.5-5 g/L
P: 0.3-0.5 g/L.

12. A method according to claim 9, wherein the fermentation mixture comprises between 5 g/L and 10 g/L of a yeast extract.

13. A method according to claim 9, wherein the fermentation mixture comprises glycerol at an initial concentration of between 10 g/L and 25 g/L.

14. A method according to claim 9, wherein a final concentration of 20 g/L or more of succinic acid is produced.

15. A method according to claim 9, wherein the succinic acid is produced at a yield of 0.7 or more units of succinic acid produced per unit of glycerol.

16. A method of producing succinic acid from glycerol, the method comprising:
a) mixing an *Actinobacillus succinogenes* bacterium with improved ability to convert glycerol to succinic acid produced by the method of claim 1 and a medium comprising glycerol to produce a fermentation mixture; and
b) incubating the fermentation mixture, under conditions that promote fermentation to produce succinic acid, until a final concentration of 20 g/L or more of succinic acid is produced wherein the *Actinobacillus succinogenes* starter strain corresponds to the strain deposited as American Type Culture Collection Number 55618 (ATCC No. 55618).

17. A method according to claim 16, wherein the final concentration of succinic acid is between 20 g/L-32 g/L.

18. A method of producing succinic acid from glycerol, the method comprising:
a) mixing an *Actinobacillus succinogenes* bacterium with improved ability to convert glycerol to succinic acid produced by the method of claim 1 and a medium comprising glycerol to produce a fermentation mixture; and
b) incubating the fermentation mixture, under conditions that promote fermentation to produce succinic acid at a yield of 0.7 or more units of succinic acid produced per unit of glycerol,
wherein the *Actinobacillus succinogenes* starter strain corresponds to the strain deposited as American Type Culture Collection Number 55618 (ATCC No. 55618).

19. A method according to claim 18, wherein the yield is between 0.7-1.2.

* * * * *